US007001727B2

(12) United States Patent
Ellman et al.

(10) Patent No.: US 7,001,727 B2
(45) Date of Patent: Feb. 21, 2006

(54) PHARMACOPHORE RECOMBINATION FOR THE IDENTIFICATION OF SMALL MOLECULE DRUG LEAD COMPOUNDS

(75) Inventors: Jonathan A. Ellman, Oakland, CA (US); Ingrid Choong, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/670,607

(22) Filed: Sep. 26, 2003

(65) Prior Publication Data
US 2004/0132100 A1    Jul. 8, 2004

Related U.S. Application Data

(60) Division of application No. 10/029,304, filed on Dec. 28, 2001, which is a continuation of application No. 09/277,461, filed on Mar. 26, 1999, now Pat. No. 6,344,334, which is a continuation-in-part of application No. 09/049,754, filed on Mar. 27, 1998, now Pat. No. 6,344,330.

(51) Int. Cl.
 *C12Q 1/68* (2006.01)
(52) U.S. Cl. ............................. 435/6; 435/4; 435/7.1
(58) Field of Classification Search .................. 435/4, 435/6, 7.1
 See application file for complete search history.

(56) References Cited

U.S. PATENT DOCUMENTS

| | | | |
|---|---|---|---|
| 4,727,022 A | 2/1988 | Skold et al. | |
| 4,766,133 A * | 8/1988 | Fischli et al. ............... | 514/338 |
| 5,362,859 A | 11/1994 | Zale | |
| 5,422,281 A | 6/1995 | Harris et al. | |
| 5,491,169 A | 2/1996 | Roques et al. | |
| 5,512,435 A | 4/1996 | Renschler et al. | |
| 5,543,507 A | 8/1996 | Cook et al. | |
| 5,658,727 A | 8/1997 | Barbas et al. | |
| 5,683,867 A | 11/1997 | Biesecker et al. | |
| 5,698,401 A | 12/1997 | Fesik et al. | |
| 6,335,155 B1 | 1/2002 | Wells et al. | |
| 6,552,060 B1 * | 4/2003 | Kirkpatrick ................. | 514/398 |

FOREIGN PATENT DOCUMENTS

| | | |
|---|---|---|
| EP | 0 523 978 A | 1/1993 |
| WO | WO 93/18052 | 9/1993 |
| WO | WO 96/33416 | 10/1996 |
| WO | WO 97/18469 | 5/1997 |
| WO | WO 98/11436 | 3/1998 |
| WO | WO 98/48264 | 10/1998 |

OTHER PUBLICATIONS

Das, K. C.; White, C. W. "Detection of thioredoxin in human serum and biological samples using a sensitive sandwich ELISA with digoxigenin-labeled antibody" Journal of Immunological Methods Feb. 1, 1998, 211, 9-20.*
Shuker et al., Science 274-:1531-1534 (1996).
Singh et al., J. Am. Chem. Soc. 118:1669-1676 (1996).
Weber et al., Agnew. Chem. Int. Ed. Engl. 34:2280-2282 (1995).
Huc et al., Proc. Natl. Acad. Sci. USA: 94:2106-2110 (1997).
Holland, Sci. Amer. USA 66-72 (1997).
Rowan, et al., Angew. Chem. Int. Ed. Engl.35:2143-2145.
Rowan, et al., J. Am. Chem. Soc. 119:2578-2579 (1997).
Hajduk, et al., Sci. 278:497-498 (1997).
Rose, J. Amer. Chem. Soc. 116:30-33 (1994).
Shao et al., Amer. Chem. Soc. 117:3893-3899 (1995).
Jencks, Proc. Natl. Acad. Sci, 78:4046-4050 (1981).
Olejniczak et al., J. of Am. Chem. Soc, 119:5828-5832 (1997).
Nakamura et al., Biochemistry 24:1364-1376 (1985).
Hajduk, et al., J. Am. Chem. Soc. 119:5818-5827 (1997).
Dolle et al., J. of Combinatorial Chem. 1:229-382 (1999).
Puius et al. Proc. Natl. Acad. Sci. 94:13420-13425 (1997).
Hajduk et al., J. Am. Chem. Soc. 119:5818-5827 (1997).
Eliseev Drug Discovery and Development 1:106-115 (1998).
Jindal, et al., Spectrum Drug Discovery and Design, 20:1-15 (1998).
Baldwin, et al., J. Am. Chem. Soc., 117:5588-5589 (1995).
Gilbertson et al., Tetrahedron Letters 37:6475-6478 (1996).
Pfistermueller, et al., FEBS Letters 39:14-20 (1996).
Godfrey, et al., J. Exp. Med. 80:757-762 (1994).
Boger et al., Solution-Phase Combinatorial Synthesis via the Olefin Metathesis Reaction, Bioorg. Med. Chem. Lett., vol. 7, No. 4, pp. 463-468 (1997).
Gordon et al., Applications of Combinatorial Techniques to Drug Discovery, 2. Combinatorial Organic Synthesis, Library Screening Strategies and Future Directions, J. Med. Chem., vol. 37, No., 10, pp. 1885-1401 (1994).
Sigal et al. Polyacrylamides Bearing Pendant a-Sialoside Groups Strongly Inhibit Agglutination of Erythrocytes by Influenza Virus . . . J. Am. Chem. Soc. vol. 118, No. 16, pp. 3789-3400. (1996).

(Continued)

Primary Examiner—Andrew Wang
Assistant Examiner—Jon D. Epperson
(74) Attorney, Agent, or Firm—Foley & Lardner LLP

(57) ABSTRACT

A library of candidate target binding fragments (CTBF's) each CTBF being a small organic molecule and having a linkable functional group (LFG) or blocked form thereof (BLFG), wherein the LFG or BLFG contains a linking group (LG), the LG being a disulfide group.

22 Claims, 9 Drawing Sheets

OTHER PUBLICATIONS

Zhao et al. Coumarin-Based Inhibitors of HIV Integrase, J. Med. Chem., vol. 40, No. 2, pp. 242-249, (1997).

Hadjuk et al., One-Dimensional Relation and Diffusion Edited NMR Methods for Screening Compounds that Bind to Macromolecules, J. am. Chem. Soc., vol. 119, No. 50, pp. 12257-12261, (1997).

Keyes et al., Correlation of Anti-HIV Potency with Lipophilicity in a Series of Cosalane Analogs . . . J. Med. Chem., vol. 39, No. 2, pp. 508-514, (1996).

Zhao et al., Arylamide Inhibitors of HIV-1 Integrase, J. Med. Chem. 40, pp. 1186-1194 (1997).

Konings, D.A.M. et al., "Deconvolution of Combinatorial Libraries for Drug Discovery: Theoretical Comparison of Pooling Strategies" J, Med. Chem. 1996, 39, 2710-2719.

Hioki, H. and Still, W.C., "Chemical evolution: A model system that selects and amplifies a receptor for the tripeptide (D) Pro(L) Val (D) Val," Journal of Organic Chemistry, vol. 63, No. 4, Feb. 20, 1998, pp. 904-905, published on Web Jan. 22, 1998.

Janda, K. Tagged versus Untagged Libraries: Methods for the Generation and Screening of Combinatorial Chemical Libraries, Nov. 1994, Proc. Natl. Acad. Sci. USA, vol. 91, pp. 10779-10785.

Nicolau, K.C, "Handbook of Combinatorial Chemistry" Weinheim Germany: Wiley-VCH 2002, vol. 1, p. v-xxv.

Nazarpack-Kandlousy, N. et al, "Synthesis and Characterization of a Mixture-Based Library of Oxime Ethers Based on a Common Aromatic Scaffold," Journal of Combinatorial Chemistry, 1999, (3), 199-206.

Tuchscherer, G. "Template Assembled Synthetic Proteins: Condensation of a Multifunctional Peptide to a Topological Template via Chemoselective Ligation ," Tetrahedron Letters, vol. 34, No. 52, pp. 8419-8422; 1993; Great Britain.

Silverman, Richard B., The Organic Chemistry of Drug Design and Drug Action, New York : Academic Press, Inc. 1992, pp. 19-23, especially Table 2.2.

* cited by examiner

Chromones

Phenols

Furans

Phenoxides

Diverse n= 2-5

+

TARGET BINDING FRAGMENT ASSEMBLY

PHARMACOPHORE RECOMBINATION FOR THE IDENTIFICATION OF SMALL MOLECULE DRUG LEAD COMPOUNDS

This invention was made with Government support under Contract No. R01 GM50353 awarded by the National Institutes of Health. The Government has certain rights to this invention.

FIELD OF THE INVENTION

The present invention is directed to novel methods for identifying small molecule drug lead compounds.

BACKGROUND OF THE INVENTION

In response to the ever increasing demand for novel compounds useful in the effective treatment of various maladies, the medical research community has developed a number of different strategies for discovering and optimizing new therapeutic drugs. For the most part, these strategies are dependent upon molecular techniques that allow the identification of tightly binding ligands for a given biological target molecule. Once identified, these ligands may then carry out their therapeutic functions by activating, inhibiting or otherwise altering the activity of the molecular target to which they bind.

In one such strategy, new therapeutic drugs are identified by screening combinatorial libraries of synthetic small molecule compounds, determining which compound(s) have the highest probability of providing an effective therapeutic and then optimizing the therapeutic properties of the identified small molecule compound(s) by synthesizing structurally related analogs and analyzing them for binding to the target molecule (Gallop et al., *J. Med. Chem.* 37:1233–1251 (1994), Gordon et al., *J. Med. Chem.* 37:1385–1401 (1994), Czarnik and Ellman, *Acc. Chem. Res.* 29:112–170 (1996), Thompson and Ellman, *Chem. Rev.* 96:555–600 (1996) and Balkenhohl et al., *Angew. Chem. Int. Ed.* 35:2288–2337 (1996)). However, this process is not only time consuming and costly, it often does not provide for the successful identification of a small molecule compound having sufficient therapeutic potency for the desired application. For example, while the preparation and evaluation of combinatorial libraries of small molecules has proven somewhat useful for new drug discovery, the identification of small molecules for difficult molecular targets (e.g., such as those useful for blocking or otherwise taking part in protein-protein interactions) has not been particularly effective (Brown, *Molecular Diversity* 2:217–222 (1996)).

One issue that limits the success of combinatorial library approaches is that it is possible to synthesize only a very small fraction of the possible number of small molecules. For example, greater than $10^{60}$ different small molecules having valid chemical structures and molecular weights under 600 daltons can be envisioned. However, even the most ambitious of small molecule combinatorial library efforts have been able to generate libraries of only tens to hundreds of millions of different compounds for testing. Therefore, combinatorial technology allows one to test only a very small subset of the possible small molecules, thereby resulting in a high probability that the most potent small molecule compounds will be missed. Thus, suitable small molecule compounds having the required availability, activity or chemical and/or structural properties often cannot be found. Moreover, even when such small molecule compounds are available, optimization of those compounds to identify an effective therapeutic often requires the synthesis of an extremely large number of structural analogs and/or prior knowledge of the structure of the molecular target for that compound. Furthermore, screening large combinatorial libraries of potential binding compounds to identify a lead compound for optimization can be difficult and time-consuming because each and every member of the library must be tested. It is evident, therefore, that novel methods for rapidly and efficiently identifying new small molecule drug leads are needed.

Living organisms evolve through a process that includes both (1) genetic recombination, where sexual reproduction acts to mix and recombine the attributes of the parent organisms to provide progeny having attributes of both parents, and (2) natural selection, where only those progeny that are sufficiently "fit" are capable of passing their attributes on to the next generation. Approaches that closely model the process by which organism evolve have previously been reported for identifying small molecules that bind to receptors and enzymes (Weber et al., *Angew. Chem. Int. Ed. Engl.* 34:2280–2282 (1995) and Singh et al., *J. Am. Chem Soc.* 118: 1669–1676 (1996)). These approaches are based upon the mathematical method termed "genetic algorithms" (Holland, *Sci. Am.* 66–72 (1992)). Using genetic algorithms, a population of different compounds is screened to identify the compounds that bind to the receptor or enzyme (i.e., the "fittest" compounds). A population of progeny compounds is then prepared by recombining the building blocks that were used to prepare the "fittest" compounds. A screen is then performed to identify the compounds that bind to the target with the highest affinity, which are made up of the optimal building block combinations.

However, because the building blocks employed in the genetic algorithm approach are not preselected, one of two techniques are used to identify tight binding ligands: (1) extremely large populations of compounds must be screened and recombined, or (2) multiple rounds of screening and recombination are performed on relatively small populations where additional building blocks are gradually introduced through a process that is analogous to genetic mutation. In this second approach, many rounds of selection, recombination and building block introduction are required to identify the optimal building block combinations in analogy to the many rounds of selection, reproduction and mutation that are required in the evolution of living organisms. Thus, the use of genetic algorithms is currently limited because of the large amount of time required for compound preparation and screening, wherein the goal of new drug discovery is to identify a potent compound as quickly as possible.

Another recently reported approach for identifying high affinity ligands for molecular targets of interest is by determining structure-activity relationships from nuclear magnetic resonance analysis, i.e., "SAR by NMR" (Shuker et al., *Science* 274:1531–1534 (1996) and U.S. Pat. No. 5,698,401 by Fesik et al.). In this approach, the physical structure of a target protein is determined by NMR and then small molecule building blocks are identified that bind to the protein at nearby points on the protein surface. Adjacently binding small molecules are then coupled together with a linker in order to obtain compounds that bind to the target protein with higher affinity than the unlinked compounds alone. Thus, by having available the NMR structure of the target protein, the lengths of linkers for coupling two adjacently binding small molecules can be determined and small molecule ligands can be rationally designed. This approach has been useful for identifying compounds that bind to FK506 binding protein with a $K_d$=20 nM (Shuker et al., supra) and to stromelysin with a $K_d$=15 nM (Hajduk et al., *J. Am. Chem. Soc.* 119:5818–5827 (1997) and Hajduk et al., *J. Am. Chem. Soc.* 119:5828–5832 (1997)).

However, while the SAR by NMR method is powerful, it also has serious limitations. For example, the approach requires huge amounts of target protein (>200 mg) and this protein typically must be $^{15}$N-labeled so that it is useful for NMR studies. Moreover, the SAR by NMR approach usually requires that the target protein be soluble to >0.3 mM and have a molecular weight less than about 25–30 kDa. Additionally, the structure of the target protein is first resolved by NMR, a process which often can require a 6 to 12 month time commitment.

From the above, it is evident that there is a need for novel techniques useful for rapidly and efficiently identifying small molecule drug lead compounds that are capable of binding with high affinity to a molecular target of interest. We herein describe for the first time a method which is based upon pharmacophore recombination, wherein a population of small molecule pharmacophores are "pre-selected" for the ability to bind to a molecular target and wherein the small molecule pharmacophores that bind with the highest affinity are then chemically linked in various combinations to provide a library of potential high affinity binding ligands. The library of potential binding ligands is then screened using a simple functional assay for the presence of one or more compounds that bind to the target molecule with very high affinity.

SUMMARY OF THE INVENTION

Applicants herein describe a molecular approach for rapidly and efficiently identifying small molecule ligands that are capable of binding to a target biological molecule with high affinity, wherein ligand compounds identified by the method are useful as new small molecule drug lead compounds. The herein described methods allow a library of only the most favorable compounds to be assayed for binding to a target biological molecule without the need for screening all possible small molecule compounds and combinations thereof for binding to the target as is required in standard combinatorial library approaches. More specifically, a library of candidate target binding fragments is assembled and subjected to a first screen or "pre-screened" to identify a subset of that library that bind to a target biological molecule with or below a certain dissociation constant. Those candidate target binding fragments identified during this "pre-screening" step as being capable of binding to the target biological molecule are then coupled or cross-linked in a variety of combinations using one or more linker elements to provide a library of potential high affinity binding ligands or candidate cross-linked target binding fragments, whose building blocks represent the small candidate target binding fragments having the highest affinity for the target biological molecule as identified in the "pre-screening" step. The library of potential ligands or candidate cross-linked target binding fragments for binding to the target biological molecule is then screened a second time to identify those members that exhibit the lowest dissociation constant for binding to the target biological molecule. Because the library of candidate target binding fragment building blocks is initially "pre-screened" to select for a much smaller set of the most favorable building blocks, the most productive building block and cross-linker combinations can be identified without the laborious task of screening all possible combinations of all building blocks coupled together by a set of linkers. The process of identifying high affinity drug lead compounds is therefore, greatly expedited.

With regard to the above, one embodiment of the present invention is directed to a method for identifying drug lead compounds that bind to a biological target molecule of interest, wherein the method comprises the steps of:

(a) Assembling a library of candidate target binding fragments (CTBF) capable of being chemically cross-linked by a cross-linker element to provide candidate cross-linked target binding fragments for binding to the target biological molecule;

(b) screening the library of candidate target binding fragments to identify at least first and second candidate target binding fragments which bind to the target biological molecule;

(c) chemically cross-linking the at least first and second candidate target binding fragments or structurally related analogs thereof with a cross-linker element to provide a library of candidate cross-linked target binding fragments for binding to the target biological molecule; and (d) screening the library obtained in (c) to identify a drug lead compound that binds to the target biological molecule.

In various preferred embodiments, the library of candidate target binding fragments may comprise compounds of less than 500 daltons, may comprise simple aldehydes, amines, amides, carbamates, ureidos, sulfonamides, alcohols, carboxylic acids, thiols, aryl halides, alkynes, alkynes, ketones, ethers and/or oximes and/or may bind to the target biological molecule with a $K_d$ of 10 mM or lower. In a particularly preferred embodiment, the library or candidate target binding fragments may comprise oxime compounds, wherein the structurally related aldehyde analogs of those oxime compounds are capable of being chemically cross-linked via an O,O'-diaminoalkanediol cross-linker. Target biological molecules that find use in the described methods include, for example, proteins, nucleic acids and saccharides, preferably proteins. Preferred TBM's include human or human pathogen proteins, especially enzymes, human hormones, human receptors and fragments thereof. These TBM's may all contain atoms of naturally occuring isotopic abundance.

In other preferred embodiments, the library of candidate cross-linked target binding fragments comprises candidate cross-linked target binding fragments of less than about 1000 daltons, that may be homo- or heterodimeric having a $K_d$ for the TBM of from about 500 μM to about 500 nM or lower.

Another embodiment of the present invention is directed to a method for inhibiting the interaction between first and second biological molecules, wherein the method comprises the step of contacting a system comprising both the first and second biological molecules with a binding inhibitory amount of a candidate cross-linked target binding fragment identified by the above described method, wherein the candidate cross-linked target binding fragment binds to one of the first or second biological molecules and inhibits their ability to interact.

A further embodiment of the present invention is directed to a drug lead compound made by the the method described herein, where the compound is represented by the formula:

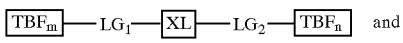 and

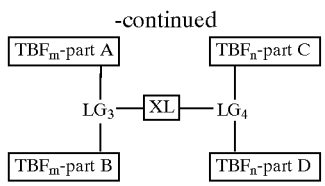

where

TBF$_m$ represents a first TBF selected from step (d);

TBF$_n$ represents a second TBF selected from step (d);

TBF$_m$-part A and B represent TBF$_m$ from step (d) where each fragment is bonded to a single atom in LG$_3$;

TBF$_n$-part C and D represent TBF$_n$ from step (d) where each fragment is bonded to a single atom in LG$_4$;

XL represents a cross-linker of the formula —(C$_0$–C$_2$-alkyl-L$^1$-L$^2$-L$^3$-L$^4$-L$^5$-C$_0$–C$_2$-alkyl)-;

LG$_1$ and LG$_2$ are linking groups independently selected from the group —C(R$_a$)=N—O—, —O—N=C(R$_a$)—, —CH$_2$—N(R$_a$)—, —N(R$_a$)—CH$_2$—, —C(=O)—N(R$_a$)—, —N(R$_a$)—C(=O)—, —N(R$_a$)—C(=O)—O—, —O—C(=O)—N(R$_b$)—, —N(R$_b$)—C(=O)—N(R$_b$)—, —N(R$_b$)—C(=O)—N(R$_b$)—, —SO$_2$—N(R$_a$)— and —N(R$_a$)—SO$_2$—;

LG$_3$ and LG$_4$ are linking groups independently selected from the group >C=N—O—, —O—N=C<, —CH$_2$—N<, >N—CH$_2$—, —C(=O)—N<, >N—C(=O)—, >N—C(=O)—O—, —O—C(=O)—N<, >N—C(=O)—N(R$_b$)—, —N(R$_a$)—C(=O)—N<, —SO$_2$—N< and >N—SO$_2$—, where < and > represent two bonds linking CTBF-part A, B, C, or D to the single N or C atom in LG$_3$ or LG$_4$;

R$_a$ and R$_b$ are independently selected from the group hydrogen, C$_1$–C$_{10}$-alkyl, C$_0$–C$_{10}$-alkyl-C$_6$–C$_{10}$-aryl, C$_6$–C$_{10}$-aryl-C$_0$–C$_{10}$-alkyl, C$_0$–C$_{10}$-alkyl-heterocycle-C$_0$–C$_{10}$-alkyl, C$_1$–C$_6$-alkyl-NH—C$_1$–C$_6$-alkyl, C$_0$–C$_{10}$-alkyl-O—C$_0$–C$_{10}$-alkyl, C$_0$–C$_{10}$alkyl-C(=O)—C$_0$–C$_{10}$-alkyl, C$_0$–C$_{10}$-alkyl-NH—C(=O)—C$_0$–C$_{10}$-alkyl, C$_0$–C$_{10}$-alkyl-O—C(=O)—C$_0$–C$_{10}$-alkyl, where any alkyl, aryl or heterocycle is optionally substituted with C$_1$–C$_{10}$-alkyl, C$_1$–C$_{10}$-alkoxy, C$_6$–C$_{10}$-aryl, C$_6$–C$_{10}$-aryloxy, halo (F, Cl, Br, I), hydroxy, carboxy, amino, nitro and S(O)$_{0-3}$;

TBF$_m$, TBF$_n$, TBF$_m$-part A, TBF$_m$-part B, TBF$_n$-part C and TBF$_n$-part D are each independently represented by formula I -A-(Cycle 1)-B-(Cycle 2)-E  (I)

Where

Cycle 1 and Cycle 2 are independently present or absent and are selected from a mono-, bi-, or tricyclic saturated, unsaturated, or aromatic ring, each ring having 5, 6 or 7 atoms in the ring where the ring atoms are carbon or from 1–4 heteroatoms selected from; nitrogen, oxygen, and sulfur, and where any sulfur ring atom may optionally be oxidized and any carbon ring atom may form a double bond with O, NR$''$ and CR$^1$R$^{1'}$, each ring nitrogen may be substituted with R$''$ and any ring carbon may be substituted with R$^d$;

A and B are independently selected from

—L$^3$—L$^2$—L$^1$—,

—L$^4$—L$^3$—L$^2$—L$^1$— and

—L$^5$—L$^4$—L$^3$—L$^2$—L$^1$—, where:

L$^1$ is absent or may be selected from oxo (O), S(O)$_s$, C(=O), C(=N—R$''$), C(=CR$^1$R$^{1'}$), C(R$^1$R$^{1'}$), C(R$^1$), C, het, N(R$''$) or N;

L$^2$ is absent or may be selected from oxo (O), S(O)$_s$, C(=O), C(=N—R$''$), C(=CR$^2$R$^{2'}$), C(R$^2$R$^{2'}$), C(R$^2$), C, het, N(R$''$) or N;

L$^3$ is absent or may be selected from oxo (O), S(O)$_s$, C(=O), C(=N—R$''$), C(=CR$^3$R$^{3'}$), C(R$^3$R$^{3'}$) C(R$^3$), C, het, N(R$''$) or N;

L$^4$ is absent or may be selected from oxo (O), S(O)$_s$, C(=O), C(=N—R$''$), C(=CR$^4$R$^{4'}$), C(R$^4$R$^{4'}$), C(R$^4$), C, NR$''$ or N; and L$^5$ is absent or may be selected from oxo (O), S(O)$_s$, C(=O), C(=N—R$''$), C(R$^5$R$^{5'}$), C(=CR$^5$R$^{5'}$), C(R$^5$), C, NR$''$ or N;

R$^1$, R$^{1'}$, R$^2$, R$^{2'}$, R$^3$, R$^{3'}$, R$^4$, R$^{4'}$, R$^5$ and R$^{5'}$ each are independently selected from R$^a$, R$^{a'}$, R$^c$ and U-Q-V—W; where s is 0–2

Optionally, each R$^1$–R$^5$ or NR$''$ together with any other R$^1$–R$^5$ or NR$''$ may form a mono-, bi-, or tricyclic saturated, unsaturated, or aromatic ring, each ring being a homo- or heterocycle having 5, 6 or 7 atoms in the ring, optionally each ring containing 1–4 heteroatoms selected from N, O and S where any ring carbon or sulfur atom may optionally be oxidized, each ring nitrogen optionally substituted with R$''$ and each ring carbon optionally substituted with R$^d$;

E is -L$^1$-L$^2$-L$^3$-R$^a$;

R$^a$ is selected from the group; hydrogen, halo(F, Cl, Br, I), halo(F, Cl, Br, I)—C$_1$–C$_{11}$alkyl, halo(F, Cl, Br, I)—C$_1$–C$_{11}$alkoxy, hydroxy-C$_1$–C$_{11}$alkyl, cyano, isocyanate, carboxy-C$_0$–C$_{11}$alkyl, amino, C$_0$–C$_{11}$alkyl-amino-(C$_1$–C$_8$alkyl), C$_0$–C$_{11}$alkyl-amino-di-(C$_1$–C$_8$alkyl), aminocarbonyl, C$_1$–C$_{11}$alkylcarbonylamino, carboxamido, carbamoyl, carbamoyloxy, formyl, formyloxy, azido, nitro, hydrazide, hydroxamic acid, imidazoyl, ureido, thioureido, thiocyanato, hydroxy, C$_1$–C$_6$alkoxy, mercapto, sulfonamido, het, phenoxy, phenyl, benzyl, benzyloxy, benzamido, tosyl, morpholino, morpholinyl, piperazinyl, piperidinyl, pyrrolinyl, imidazolyl and indolyl;

R$^{a'}$ is selected from the group of C$_0$–C$_{10}$alkyl-Q-C$_0$–C$_6$alkyl, C$_0$–C$_{10}$alkenyl-Q-C$_0$–C$_6$alkyl, C$_0$–C$_{10}$alkynyl-Q-C$_0$–C$_6$alkyl, C$_3$–C$_{11}$cycloalkyl-Q-C$_0$–C$_6$alkyl, C$_3$–C$_{10}$cycloalkeny-Q-C$_0$–C$_6$alkyl, C$_1$–C$_6$alkyl-C$_6$–C$_{12}$aryl-Q-C$_0$–C$_6$alkyl, C$_6$–C$_{10}$aryl-C$_1$–C$_6$alkyl-C$_0$–C$_6$alkyl, C$_0$–C$_6$alkyl-het-Q-C$_0$–C$_6$alkyl, C$_0$–C$_6$alkyl-Q-het-C$_0$—C$_6$alkyl, het-C$_0$–C$_6$alkyl-Q-C$_0$–C$_6$alkyl, C$_0$–C$_6$alkyl-Q-C$_6$–C$_{12}$aryl and Q-C$_1$–C$_6$alky, where any aryl or het is optionally substituted with 1–3 R$^d$ and any alkyl, alkenyl or alkynyl is optionally substituted with 1–3 R$^a$;

R$^a$ and R$^{a'}$ may join to form a 3–7 member homocyclic ring substituted with 1–3 R$^a$;

R$^c$ is selected from hydrogen and substituted or unsubstituted; amino, O—C$_1$–C$_8$alkyl, amino-(C$_1$–C$_8$alkyl), amino-di-(C$_1$–C$_8$alkyl), C$_1$–C$_{10}$alkyl, C$_2$–C$_{10}$alkenyl, C$_2$–C$_{10}$alkynyl, C$_3$–C$_{11}$cycoalkyl, C$_3$–C$_{10}$cycloalkenyl, C$_1$–C$_6$alkyl-C$_6$–C$_{12}$aryl, C$_6$–C$_{10}$aryl-C$_1$–C$_6$alkyl, C$_1$–C$_6$alkyl-het, het-C$_1$–C$_6$alkyl, C$_6$–C$_{12}$aryl and het, where the substitutes on any alkyl, alkenyl or alkynyl are 1–3 R$^a$ and the substituents on any aryl or het are 1–3 R$^d$;

R$^d$ is selected from R$^h$ and R$^p$;

R$^h$ is selected from the group OH, OCF$_3$, OR$^c$, SR$^m$, halo(F, Cl, Br, I), CN, isocyanate, NO$_2$, CF$_3$, C$_0$–C$_6$alkyl NR$''$R$^{n'}$, C$_0$–C$_6$alkyl-C(=O)—NR$''$R$^{n'}$, C$_0$–C$_6$alkyl-C(=)—R$^a$, C$_1$–C$_8$alkyl, C$_1$–C$_8$alkoxy, C$_2$–C$_8$alkenyl, C$_2$–C$_8$alkynyl, C$_3$–C$_6$cycloalkyl, C$_3$–C$_6$cycloalkenyl, $C_1-C_6$alkyl-phenyl, phenyl-$C_1-C_6$alkyl, $C_1-C_6$alkyloxycarbonylamino, $C_1-C_6$alkyloxycarbonyl-$C_0-C_6$alkyl, phenyl-$C_0-C_6$alkyloxy, $C_1-C_6$alkyl-het, het-$C_1-C_6$alkyl, $SO_2$-het, O—$C_6-C_{12}$aryl, $SO_2$—$C_6-C_{12}$aryl, $SO_2$—$C_1-C_6$alkyl and het, where any alkyl, alkenyl or alkynyl may optional be substituted with 1–3 groups selected from OH, halo(F, Cl, Br, I), nitro, amino and aminocarbonyl, where the substituents on any aryl or het are 1–2 hydroxy, halo(F, Cl, Br, I), $CF_3$, $C_1-C_6$alkyl, $C_1-C_6$alkoxy, nitro and amino;

$R^m$ is selected from hydrogen, S—$C_1-C_6$alkyl, C(=O)—$C_1-C_6$alkyl, C(=O)—NR″R$^{n'}$, $C_1-C_6$alkyl, halo(F, Cl, Br, I)—$C_1-C_6$alkyl, benzyl and phenyl;

$R^n$ is selected from the group $R^c$, OH, $OCF_3$ $OR^o$, CN, isocyanate, NH—C(=O)—O—$R^c$, NH—C(=O)—$R^c$, NH—C(=O)—NHR$^c$, NH—$SO_2$—$R^s$, NH—$SO_2$—NH—C(=O)—$R^c$, NH—C(=O)—NH—$SO_2$—$R^s$, C(=O)—O—$R^o$, C(=O)—$R^c$, C(=O)—NHR$^c$, C(=O)—NH—C(=O)—O—$R^o$, C(=O)—NH—C(=O)—$R^c$, C(=O)—NH—$SO_2$—$R^s$, C(=O)—NH—NHR$^c$, $SO_2$—$R^s$, $SO_2$—O—$R^o$, $SO_2$—N(R$^c$)$_2$, $SO_2$—NH—C(=O)—O—$R^o$, $SO^2$—NH—C(=O)—O—$R^o$ and $SO_2$—NH—C(=O)—$R^c$;

$R^o$ is selected from hydrogen and substituted or unsubstituted $C_1-C_6$alkyl, $C_0-C_6$alkyl-$C_6-C_{10}$aryl, $C_1-C_6$alkylcarbonyl, $C_2-C_6$alkenyl, $C_2-C_6$alkynyl, $C_3-C_8$cycloalkyl and benzoyl, where the substitutes on any alkyl are 1–3 $R^a$ and the substituents on any aryl are 1–3 $R^p$;

$R^p$ is selected from the group; OH, COOH, COH, $NH_2$, $C_0-C_6$ alkyl, halo(F, Cl, Br, I), CN, isocyanate, $OR^o$, $SR^m$, $SOR^o$, $NO_2$, $CF_3$, $R^c$, NR″R$^n$, N(R″)—C(=O)—O—$R^o$, N(R″)—C(=O)—$R^c$, $SO_2$—$R^s$, $C_0-C_6$alkyl-$SO_2$—$R^s$, $C_0-C_6$alkyl-$SO_2$—NR″R$^{n'}$, C(=O)—$R^c$, O—C(=O)—$R^c$, C(=O)—O—$R^o$ and C(=O)—NR″R$^{n'}$, where the substitutes on any alkyl, alkenyl or alkynyl are 1–3 $R^a$ and the substituents on any aryl or het are 1–3 $R^d$;

$R^s$ is a substituted or unsubstituted group selected from; $C_1-C_8$alkyl, $C_2-C_8$alkenyl, $C_2-C_8$alkynyl, $C_3-C_8$cycloalkyl, $C_3-C_6$cycloalkenyl, $C_0-C_6$alkyl-$C_6-C_{10}$aryl, $C_6-C_{10}$aryl-$C_0-C_6$alkyl, $C_0-C_6$alkyl-het and het-$C_0-C_6$alkyl, where the substitutes on any alkyl, alkenyl or alkynyl are 1–3 $R^a$ and the substituents on any aryl or het are 1–3 $R^d$;

het is any mono-, bi-, or tricyclic saturated, unsaturated, or aromatic ring where at least one ring is a 5-, 6- or 7-membered ring containing from one to four heteroatoms selected from the group nitrogen, oxygen, and sulfur, the 5-membered ring having from 0 to 2 double bonds and the 6- or 7-membered ring having from 0 to 3 double bonds and where any carbon or sulfur atoms in the ring may optionally be oxidized, and where any nitrogen heteroatom may optionally be quaternized and where any ring may contain from 0–3 $R^d$;

U is an optionally substituted bivalent radical selected from the group; $C_1-C_6$alkyl, $C_0-C_6$alkyl-Q, $C_2-C_6$alkenyl-Q, and $C_2-C_6$alkynyl-Q, where the substituits on any alkyl, alkenyl or alkynyl are 1–3 $R^a$;

Q is absent or is selected from the group; —O—, —S(O)$_s$—, —$SO_2$—N(R″)—, —N(R″)—, —N(R″)—C(=O)—, —N(R″)—C(=O)—O—, —N(R″)—$SO_2$—, —C(=O)—, —C(=O)—O—, -het-, —C(=O)—N(R″)—, —PO(OR$^c$)O— and —P(O)O—, where s is 0–2 and the heterocyclic ring is substituted with 0–3 $R^h$;

V is absent or is an optionally substituted bivalent group selected from $C_1-C_6$alkyl, $C_3-C_8$cycloalkyl, $C_0-C_6$alkyl-$C_6-C_{10}$aryl, and $C_0-C_6$alky-het, where the substitutes on any alkyl are 1–3 $R^a$ and the substituents on any aryl or het are 1–3 $R^d$;

W is selected from the group; hydrogen, —OR$^o$, SR$^m$, —NR″R$^{n'}$, —NH—C(=O)—O—R$^o$, NH—C(=O)—NR″R$^{n'}$, —NH—C(=O)—R$^c$, —NH—$SO_2$—R$^s$, —NH—$SO_2$—NR″R$^{n'}$, —NH—$SO_2$—NH—C(=O)—R$^c$, —NH—C(=O)—NH—$SO_2$—R$^s$, —C(=O)—NH—C(=O)—O—R$^o$, —C(=O)—NH—C(=O)—R$^c$, —C(=O)—NH—C(=O)—NR″R$^{n'}$, —C(=O)—NH—$SO_2$—R$^s$, —C(=O)—NH—$SO_2$—NR″R$^n$, C(=S)—NR″R$^{n'}$, —$SO_2$—R$^s$, —$SO_2$—O—R$^o$, —$SO_2$—NR″R$^{n'}$, —$SO_2$—NH—C(=O)—O—R$^c$, —$SO_2$—NH—C(=O)—NR″R$^{n'}$, —$SO_2$—NH—C(=O)—R$^c$, —O—C(=O)—NR″R$^{n'}$, —O—C(=O)—R$^c$, —O—C(=O)—NH—C(=O)—R$^c$, —O—C(=O)—NH—$SO_2$—R$^s$ and —O—$SO_2$—R$^s$;

Optionally, TBF$_m$-part A together with TBF$_m$-part B and TBF$_m$-part C together with TBF$_n$-part D may independently form Cycle 1 substituted with -B-(Cycle 2)-E.

A drug lead precursor or intermediate of this invention is represented by $C_0$-$C_2$-alkyl-$L^1$-$L^2$-$L^3$-$L^4$-$L^5 C_0$-$C_2$-alkyl where $L^1$ through $L^5$ are defined above. Additional embodiments of the present invention will become evident to the ordinarily skilled artisan upon a review of the present specification.

DETAILED DESCRIPTION OF THE INVENTION

I. General Description

Figure 1:
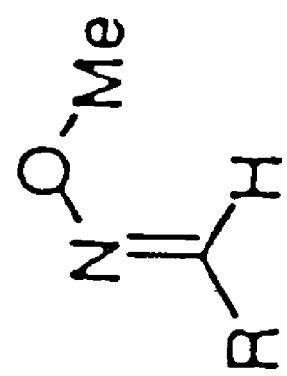
FIG. 1 shows a synthetic reaction wherein an aldehyde is reacted with O-methyl hydroxylamine to produce an O-methyl oxime compound.
Figure 1:
Figure 1:
Figure 1:
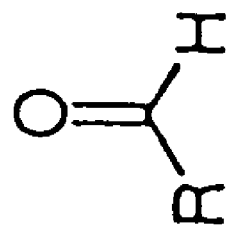

The present invention provides a rapid and efficient method for identifying small molecule candidate target binding fragments or ligands that are capable of binding with high affinity to target biological molecules (TBM) of interest. The compounds identified by the subject method find use, for example, as drug lead compounds for the development of novel therapeutic drugs. The subject method involves the assembly of a library of small organic candidate target binding fragments which are capable of being chemically cross-linked via a linker element. The library of organic candidate target binding fragments may be "pre-screened" in order to identify members of the library that are capable of binding to a target biological molecule. At least a portion of the small organic candidate target binding fragments identified during the "pre-screen" as being capable of binding to the target are then chemically cross-linked to one another in various combinations to provide a library of potential or candidate cross-linked target binding fragments for binding to the target biological molecule. The library of candidate cross-linked target binding fragments having potential to be high affinity antagonists (or agonists) are then screened to identify drug lead compounds that bind to the target biological molecule with high affinity. The step of "pre-screening" the library of small organic candidate target binding fragments to identify those that are capable of binding to the target allows one to limit the library of potential binding ligands to only those that are comprised of the most favorable organic candidate target binding fragment building blocks, thereby decreasing the required complexity of the library of potential ligands while increasing the probability of identifying a molecule exhibiting high binding affinity for the biological target molecule.

One embodiment of the present invention is directed to a method for identifying a drug lead compound that binds to a target biological molecule of interest. The subject method involves assembling a library of organic candidate target binding fragment(s) that are capable of being chemically cross-linked via a chemically compatible cross-linker to provide candidate cross-linked target binding fragment(s) for binding to the target biological molecule. In this regard, the phrase "assembling a library of organic candidate target binding fragments" is to be construed broadly and is intended to encompass all means by which one may obtain a library comprising two or more organic compounds which include, for example, obtaining such compounds from a commercial or non-commercial source, synthesizing such compounds using standard chemical synthesis technology or combinatorial synthesis technology (see Gallop et al. (1994), supra, Gordon et al. (1994), supra, Czarnik and Ellman (1996), supra, Thompson and Ellman (1996), supra and Balkenhohl et al. (1996) supra) and obtaining such compounds as degradation products from larger precursor compounds, e.g. known therapeutic drugs, large chemical molecules, and the like.

The candidate target binding fragments (CTBF) and are, for the most part, small water soluble organic molecules that have one or more chemically reactive functionalities, referred to as linkable (or linkage) functional groups (LFG) (or sites that may be readily converted to a chemically reactive functionality using standard technology (BLFG)) that provide a site for coupling to another compound or candidate target binding fragment via a chemically compatible cross-linker. Thus, the candidate target binding fragments of the present invention are capable of being chemically coupled to one another via a cross-linker to provide candidate cross-linked target binding fragments for binding to the target biological molecule, meaning that the candidate target binding fragment compounds have a reactive functionality, or a site that can be readily chemically converted to a reactive functionality, where a chemically compatible cross-linker may covalently attach thereto, thereby allowing multimerization of the candidate target binding fragments through the cross-linker. "Ligands", "candidate ligands" or "candidate cross-linked target binding fragments for binding to a "target biological molecule" for purposes herein are compounds that are obtained from reacting two or more organic compounds, which may be the same or different, preferably different, with one or more cross-linker so as to produce a molecule comprising two or more target binding fragments and one or more cross-linker. Such ligands are referred to herein as candidate cross-linked target binding fragments (CXL-TBF).

Candidate target binding fragments having the linkage functional group modified or blocked so that it contains substantially the same linking group as is found in the candidate cross-linked binding fragments are sometimes referred to as monomers. Monomers or monomeric compounds that find use in the present invention include, for example, aldehydes, ketones, oximes, such as O-alkyl oximes, preferably O-methyl oximes, hydrazones, semicarbazones, carbazides, primary amines, secondary amines, such as N-methylamines, tertiary amines, such as N,N-dimethylamines, N-substituted hydrazones, hydrazides, alcohols, ethers, thiols, thioethers, thioesters, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, and aziridines, and the like, all of which have chemically reactive functionalities (or are directly prepared from precursor compounds that have chemically reactive functionalities) capable of linking, either directly or indirectly, to a cross-linker. In fact, virtually any small organic molecule that is capable of being chemically coupled to another small organic molecule may find use in the present invention with the proviso that it is sufficiently soluble in aqueous solutions to be tested for its ability to bind to a target biological molecule.

The above described monomers or candidate target binding fragments will serve as the individual building blocks for candidate cross-linked binding fragments prepared therefrom. Candidate target binding fragments that find use herein will generally be less than about 2000 daltons in size, usually less than about 1500 daltons in size, more usually less than about 750 daltons in size, preferably less than about 500 daltons in size, often less than about 250 daltons in size and more often less than about 200 daltons in size, although organic molecules larger than 2000 daltons in size will also find use herein. Candidate target binding fragments that find use may be employed in the herein described method as originally obtained from a commercial or non-commercial source (for example, a large number of small organic chemical compounds that serve as candidate target binding fragments are readily obtainable from commercial suppliers such as Aldrich Chemical Co., Milwaukee, Wis. and Sigma Chemical Co., St. Louis, Mo.) or may be obtained by chemical synthesis. Examples of the latter include the preparation of a library of organic oxime compounds from a single step condensation of commercially available aldehydes with O-alkyl hydroxylamine as described in Example I below and the preparation of a library of N,N-dimethylamine candidate cross-linked target binding fragments from the reductive amination of commercially available aldehydes and dimethylamine using support-bound triacetoxyborohydride as described in Example II below and by Kaldor et al., *Tetrahedron Lett.* 37:7193–7196 (1996).

Libraries of candidate target binding fragments or candidate cross-linked target binding fragments which find use herein will generally comprise at least 2 organic compounds, often at least about 25 different organic compounds, more often at least about 100 different organic compounds, usually at least about 500 different organic compounds, more usually at least about 1000 different organic compounds, preferably at least about 2500 different organic compounds, more preferably at least about 5000 different organic compounds and most preferably at least about 10,000 or more different organic compounds. Libraries may be selected or constructed such that each individual molecule of the library may be spatially separated from the other molecules of the library (e.g., each member of the library is present in a separate microtiter well) or two or more members of the library may be combined if methods for deconvolution are readily available. The methods by which the library of organic compounds are prepared will not be critical to the invention.

Once assembled, a library of organic candidate target binding fragments will be screened using one of any number of different known assays for the purpose of identifying candidate cross-linked target binding fragments that are capable of binding to a target biolocical molecule of interest. "Biological target molecules", "target biological molecules", "target biomolecules", "molecular targets", "biological targets", and other grammatical equivalents refer to target biological molecules (TBM) that are available (either commercially, recombinantly, synthetically or otherwise) in sufficient quantities for use in in vitro binding assays and for which there is some interest for identifying a high affinity binding partner. For the most part, target biological molecules are proteins, including human proteins or human pathogen proteins that may be associated with a human disease condition, such as cell surface and soluble receptor proteins, such as lymphocyte cell surface receptors, enzymes, such as proteases, clotting factors, serine/threonine kinases and dephosphorylases, tyrosine kinases and dephosphorylases, bacterial enzymes, fungal enzymes and viral enzymes, signal transduction molecules, transcription factors, proteins associated with DNA and/or RNA synthesis or degradation, immunoglobulins, hormones, receptors for various cytokines including, for example, erythropoietin/EPO, granulocyte colony stimulating receptor, granulocyte macrophage colony stimulating receptor, thrombopoietin (TPO), IL-1, IL-2, IL-3, IL-4, IL-5, IL-6, IL-10, IL-11, IL-12, growth hormone, prolactin, human placental lactogen (LPL), CNTF, octostatin, various chemokines and their receptors such as RANTES, MIPI-α, IL-8, various ligands and receptors for tyrosine kinases such as insulin, insulin-like growth factor 1 (IGF-1), epidermal growth factor (EGF), heregulin-α and heregulin-β, vascular endothelial growth factor (VEGF), placental growth factor (PLGF), tissue growth factors (TGF-α and TGF-β), other hormones and receptors such as bone morphogenic factors, folical stimulating hormone (FSH), and leutinizing hormone (LH), tissue necrosis factor (TNF), apoptosis factor-1 and -2 (AP-1 and AP-2), and proteins and receptors that share 20% or more sequence identity to these, and the like, nucleic acids, including both DNA and RNA, saccharide complexes, and the like.

For the step(s) of screening libraries of candidate target binding fragments or candidate cross-linked target binding fragments for members having the ability to bind to a target biological molecule of interest, a simple ELISA assay may be used to (a) identify member(s) of the library that are capable of binding to the target, and (b) determine the approximate Kd with which the library member(s) bind to the molecular target. While ELISA assays are preferred for screening libraries of organic compounds, virtually any in vitro assay that allows one to detect binding of the target biological molecule by an organic compound may be employed for screening the library, wherein such assays include ELISA, other sandwich-type binding assays, binding assays which employ labeled molecules such as radioactively or fluorescently labeled molecules, fluorescence depolarization, calorimetry, protein denaturation, resistance to proteolysis, gel filtration, equilibrium dialysis, surface plasmin resonance, X-ray crystallography, and the like. Such assays either measure the ability of library members to bind directly to the target biological molecule or are competition binding assays designed to measure the ability of library members to inhibit the interaction between the target biological molecule and another molecule that binds to the target biological molecule. Any of the above assays may be employed to screen libraries of candidate compounds to identify those that bind to a target biological molecule.

For the step of screening a library of candidate compounds to identify those that bind to a target biological molecule, it will be well within the skill level in the art to determine the concentration of the library members to be employed in the binding assay. For the most part, the screening assays will employ concentrations of candidate compounds ranging from about 0.01 to 10 mM, preferably from about 0.05 to 5 mM.

The step of pre-screening a library of candidate target binding fragments to identify those that bind to a target biological molecule allows one to identify and isolate only those members of the library that have some binding affinity for the target. As such, in contrast to standard combinatorial library approaches, the small organic building blocks are "pre-screened" to select a smaller set of compounds that have some binding affinity for the target. Thus, the most productive organic compound building blocks can be identified for incorporation into the potential high affinity candidate cross-linked target binding fragments that are prepared therefrom, without having to screen all possible combinations of all of the initial candidate target binding fragment building blocks. Generally, the candidate target binding fragment library members selected as building blocks for subsequently prepared candidate cross-linked target binding fragments are those that have the highest affinity for binding to the target biological molecule. For the most part, candidate target binding fragments chosen as building blocks for incorporation into the subsequently prepared candidate cross-linked target binding fragments are those that bind to the target biological molecule with a $K_d$ of about 10 mM or less, usually about 5 mM or less, more usually about 1 mM or less, preferably about 500 μM or less, more preferably about 100 μM or less and most preferably about 50 μM or less. However, for some applications, one or more of the candidate target binding fragment(s) chosen for incorporation into the subsequently prepared candidate cross-linked target binding fragments may have an individual $K_d$ for the target biological molecule of greater than 10 mM.

Once candidate target binding fragments that bind to a target biological molecule with some desired degree of affinity are identified, at least a portion of those compounds (or structurally related analogs thereof) are chemically coupled via a cross-linker to provide a library of candidate cross-linked target binding fragments for binding to the target biological molecule, wherein those candidate crosslinked target binding fragments comprise at least one candidate target binding fragment reacted or linked with a cross-linker. Usually two or more candidate target binding fragments (or structurally related analogs thereof) linked by a cross-linker are combined and in some cases these two fragments are the same. The two (or more) candidate target binding fragments (or structurally related analogs thereof) incorporated into a candidate cross-linked target binding fragment may be the same (i.e., to provide a homodimer or homomultimer) or different (i.e., to provide a heterodimer or heteromultimer). Most commonly, the two candidate target binding fragments in the candidate cross-linked target binding fragment are different.

By "structurally related analog", "analog" and the like, is meant a fragment compound that has the same chemical structure as a fragment identified as being capable of binding to the target biological molecule except that the analog has a different chemically reactive functionality or linkage functional group(LFG) for binding to the cross-linker than does the fragment that was identified as being capable of binding to the target biological molecule in the first or pre-screen. The analog may also optionally possess or lack one or more substituents that are either lacking or present, respectively, on the fragments identified in the pre-screening provided that the presence or absence of those substituents does not substantially alter the compounds ability to bind to the target. As such, while one may pre-screen a library of, for example, candidate oxime compounds to identify candidate oxime fragments that bind to the target biological molecule, one can chemically couple not the actual oxime compounds identified in the "pre-screening" but rather aldehydes having that same chemical structures as the oximes identified in the screen (but which have an aldehyde reactive functionality rather than an oxime reactive functionality). The present invention, therefore, encompasses not only chemical coupling of the actual compounds identified in the initial "pre-screening step" (e.g., aldehydes are pre-screened and also subsequently linked), but also the chemical coupling of structurally related analogs of those compounds (e.g., oximes are pre-screened but the analogous aldehydes are linked).

As described above, candidate target binding fragment will comprise a chemically reactive functionality or linkage functional group (LFG) (or a site that can be converted to a chemically reactive functionality (BLFG)) to which a cross-linker may be covalently bound, thereby providing a means for cross-linking two or more candidate target binding fragments having a LFG ( or analog or blocked form thereof) to provide a candidate cross-linked target binding fragment. Therefore, cross-linkers that find use herein will be multifunctional, preferably bifunctional, cross-linking molecules that can function to covalently bond at least two fragment compounds together via their reactive functionalities or LFG's. Linkers or cross-linkers (XL) will have at least one, two or more and preferably only two, chemically crossreactive functional groups (CFG) on the cross-linker (XL). The chemically cross- reactive functional groups that are available for bonding to two or more candidate target binding fragments, wherein those functional groups may appear anywhere on the cross-linker, preferably at each end of the cross-linker and wherein those chemically crossreactive functional groups may be the same or different depending upon whether the candidate target binding fragment is to be linked have the same or different chemically cross-reactive functional groups. Cross-linkers that find use herein may be substituted or unsubstituted straight-chain or branched alkyl, aryl, alkaryl, heteroaryl, heterocycle and the like. Preferably straight chain alkyl will generally be at least one methylene in length, more generally from 2 to 8 methylenes in length, and optionally as many as about 12 or more methylenes or the equivalent in length. Cross-linkers may include atoms or groups to increase or improve solubility of the library members, such as oxygen atoms interspersed between methylene groups creating ether or polyether linkers. Cross-linkers will generally comprise alkyl groups either saturated or unsaturated, and therefore, may comprise alkanes, alkenes or alkynes. Heteroatoms including nitrogen, sulfur, oxygen, and the like may also be appended to the alkyl to form groups such as; alkoxyl, hydroxyalkyl or hydroxy groups. Other cross-linking groups such as aryl, especially phenylene or substituted phenylene linkers are suitably employed. Usually cross-linker elements will be of varying lengths, thereby providing a means for optimizing the binding properties of a cross-linked target binding fragment prepared therefrom.

In particularly preferred embodiments, cross-linkers may be O,O'-diamino-alkanediol compounds, preferably O,O'-diamino-$C_1$–$C_8$alkanediol, which are useful for chemically coupling aldehyde organic compounds, or any of a variety of different diamine compounds, which are useful for chemically coupling aldehyde containing compounds.

Various chemistries may be employed for chemically coupling candidate target binding fragments via a crosslinker to provide candidate cross-linked target binding fragments for binding to a target biological molecule. For example, many well known chemistries that can be employed for chemically coupling candidate target binding fragments(s) via a linker to form candidate cross-linked target binding fragments include, for example, reductive aminations between aldehydes and ketones and amines (March, *Advanced Organic Chemistry*, John Wiley & Sons, New York, 4th edition, 1992, pp.898–900), alternative methods for preparing amines (March et al., supra, p.1276), reactions between aldehydes and ketones and hydrazine derivatives to give hydrazones and hydrazone derivatives such as semicarbazones (March et al., supra, pp.904–906), amide bond formation (March et al., supra, p.1275), formation of ureas (March et al., supra, p.1299), formation of thiocarbamates (March et al., supra, p.892), formation of carbamates (March et al., supra, p.1280), formation of sulfonamides (March et al., supra, p.1296), formation of thioethers (March et al., supra, p.1297), formation of disulfides (March et al., supra, p.1284), formation of ethers (March et al., supra, p.1285), formation of esters (March et al., supra, p.1281), additions to epoxides (March et al., supra, p.368), additions to aziridines (March et al., supra, p.368), formation of acetals and ketals (March et al., supra, p.1269), formation of carbonates (March et al., supra, p.392), formation of enamines (March et al., supra, p.1284), metathesis of alkenes (March et al., supra, pp.1146–1148 and Grubbs et al., *Acc. Chem. Res.* 28:446–452 (1995)), transition metal-catalyzed couplings of aryl halides and sulfonates with alkenes and acetylenes (e.g., Heck reactions) (March et al., supra, pp.717–178), the reaction of aryl halides and sulfonates with organometallic reagents (March et al., supra, p.662), such as organoboron (Miyaura et al., *Chem. Rev.*, 95:2457 (1995)), organotin, and organozinc reagents, formation of oxazolidines (Ede et al., *Tetrahedron Letts.* 38:7119–7122 (1997)), formation of thiazolidines (Patek et al., *Tetrahedron Letts.* 36:2227–2230 (1995)), amines linked through amidine groups by coupling amines through imidoesters (Davies et al., *Canadian J. Biochem.* 50:416–422 (1972)), and the like.

The step of chemically cross-linking, via a cross-linker, at least a portion of the candidate target binding fragments identified as described above as being capable of binding to the target biological molecule or structurally related analogs thereof provides a library of candidate cross-linked target binding fragments for binding to the target molecule that comprise at least two of the candidate target binding fragments or analogs thereof and the cross-linker. As previously stated the candidate target binding fragments incorporated into candidate cross-linked target binding fragments may be the same, thereby providing a homomultimer, or different, thereby providing a heteromultimer, and libraries of candidate cross-linked target binding fragments generally comprise both homo- and hetero-multimers. Candidate cross-linked target binding fragments for binding to the target molecule are preferably dimeric, however, candidate cross-linked target binding fragments that find use may also be trimeric, tetrameric, and the like, those compounds being obtained by employing cross-linkers having more than two chemically cross-reactive functional groups for cross-linking purposes. Candidate cross-linked target binding fragments for binding to a target biological molecule that find use herein will generally be less than about 1000 daltons in size and often less than about 750 daltons in size.

Libraries of candidate cross-linked target binding fragments for binding to the target biological molecule will generally comprise at least 1 candidate cross-linked target binding fragment, usually at least about 20 different candidates, more usually at least about 100 different candidates, preferably at least about 200 different candidates, more preferably at least about 500 different candidates, most preferably at least 1,000 different candidates and often 10,000 or more. Libraries of candidate cross-linked target binding fragments may be constructed such that each individual molecule of the library may be spatially separated from the other molecules of the library (e.g., each member of the library is in a separate microtiter well) or two or more members of the library may be physically combined if methods for deconvolution are readily available.

Once obtained, libraries of candidate cross-linked target binding fragments for binding to the target biological molecule will be screened for the purpose of identifying a member(s) of the library that is/are capable of binding to the target biological molecule with high affinity. For such purposes, any of the above described screening assays can be employed, wherein preferably a biological assay such as an ELISA assay is employed.

For the step of screening a library of candidate cross-linked target binding fragments to identify one or more that bind to a target biological molecule, it will be well within the skill level in the art to determine the concentration of the compounds to be employed in the binding assay. We have herein found that candidate cross-linked target binding fragments generated by chemically coupling organic compounds that bind to a target biological molecule often exhibit surprisingly high binding affinities for the target. For the most part, candidate cross-linked target binding fragments that serve as potential drug lead compounds or may have therapeutic efficacy on their own bind to the target biological molecules with a $K_d$ of about 500 nM or less, usually about 100 nM or less, more usually about 50 nM or less. However, for various applications, one or more drug lead compound(s) having an individual $K_d$ for the target biological molecule of greater than 500 nM may also find use.

Another embodiment of the present invention is directed to a method for inhibiting the interaction between first and second biological molecules which bind to each other, wherein the method comprises contacting a system comprising those molecules with a binding inhibitory amount of a candidate cross-linked target binding fragment or drug lead compound identified by the method described above, wherein the drug lead compound or cross-linked target binding fragment binds to the first biological molecule and inhibits its ability to bind to the second biological molecule. For the most part, the first and second biological molecules will be proteins, nucleic acids, saccharide complexes, and the like, preferably at least one being a protein, more preferably both being proteins. In particularly preferred embodiments, the first or second biological molecule may be CD4 or gp120. In other preferred embodiments, the first biological molecule may be a protein wherein the second biological molecule is a receptor for that protein, a nucleic acid, either DNA or RNA, that binds to that protein or a polysaccharide or the first biological molecule is an enzyme wherein the second biological molecule is a substrate for that enzyme.

Systems that comprise both the first and second biological molecules may be either in vitro or in vivo, wherein the first and second biological molecules are situated such that they are capable of binding to one another. For in vivo applications, the lead of interest may be administered on its own or in pharmaceutically acceptable media, for example normal saline, PBS, etc. The additives may include bactericidal agents, stabilizers, buffers, or the like. In order to enhance the half-life of the drug lead compounds in vivo, the compounds may be encapsulated, introduced into the lumen of liposomes, prepared as colloids, or another conventional technique may be employed that provides for an extended lifetime thereof.

The drug lead compounds may be administered as a combination therapy with other pharmacologically active agents or may physically linked to such agents or other carriers. Various methods for administration may be employed. The drug lead compounds may be given orally, or may be injected intravascularly, subcutaneously, peritoneally, etc. A "binding inhibitory amount" of the drug lead compounds will vary widely, depending upon the nature of the first and second biological molecules, the frequency of administration, the manner of administration, the clearance of the compound from the host, and the like. Appropriate binding inhibitory amounts may be determined empirically by those skilled in the art in a routine manner. candidate cross-linked target binding fragments II. Definitions and Preferred Embodiments In its broadest embodiment, the method of this invention comprises: assembling a library of candidate target binding fragments; screening the library of candidate target binding fragments for those that bind to a target molecule; cross-linking target binding fragments to produce a library of candidate cross-linked target binding fragments; screening the library of candidate cross-linked target binding fragments for those that bind to the target molecule. The product of this method is referred to as a lead pharmaceutical or drug candidate.

Figure 9:
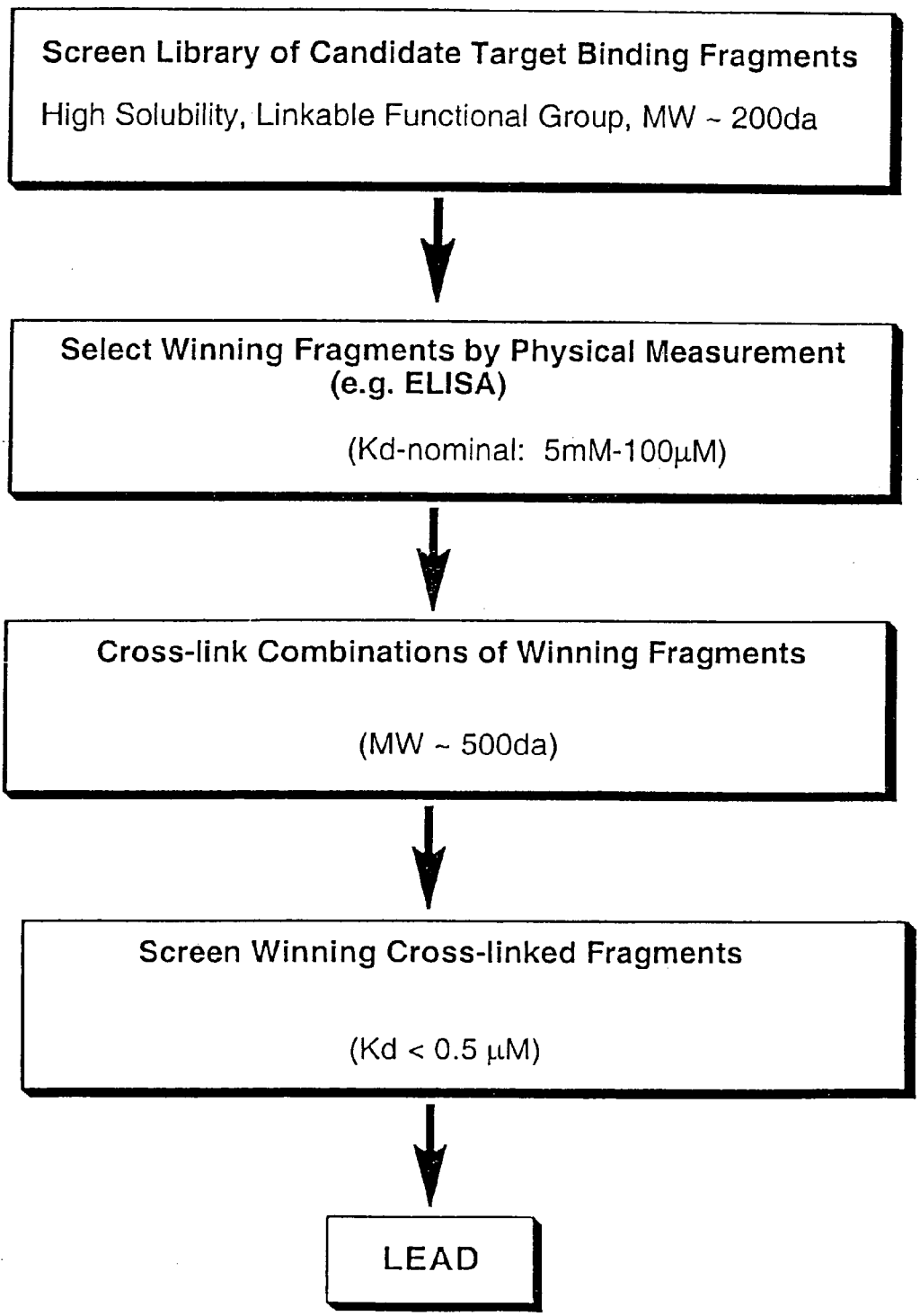
FIG. 9 shows a flow diagram for the fragment assembly sequence resulting in the production of a drug lead compound of the present invention.

More specifically (see FIG. 9), the method of this invention is used to identify lead pharmaceutical drug candidates and optionally involves the following simple steps (a–h).

(a) Assembling a library of candidate target binding fragments each fragment having a linkable (or linkage) functional group (LFG) or the blocked form thereof (BLFG), the blocked form containing linking group (LG);

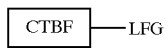

Assembling a library as used herein means any method of selecting two or more molecules to form a library for use in the method of this invention. Preferably the library will be large, greater than 50 members, and contain a diverse array of target interactive groups capable of forming non-covalent bonds, e.g. hydrogen, Van der Waals, electrostatic, hydrophobic and the like with the target molecule. Such interactive groups may include functional groups found on naturally occurring amino acid sidechains, carbohydrates, lipids, nucleic acids and their metabolites and derivatives thereof, or groups found on known pharmaceuticals. Optionally, a library may be customized to contain interactive groups known or suspected to interact with binding sites on the biological target molecule or its biological ligand.

Candidate target binding fragments (CTBF) are small water soluble organic molecules having a molecular weight of about 200 da (including the LFG) capable of forming a non-covalent complex with a target biological molecule (TBM). This complex may be of low affinity having a Kd as low as about 5 mM. The CTBF's are commercially available or may be synthesized by known procedures.

Linkable (or linkage) functional groups (LFG) include any functional groups capable of reacting with a chemically cross-reactive functional group (CFG) on a cross-linker (XL) thereby forming a stable covalent bond with the cross-linker. This covalent bond is referred to simply as a linking group (LG). When the linked molecule contains more than one linking group an integer following LG is used to indicate the number of the LG in the molecule. The LFG includes blocked, protected or otherwise transformed groups that may or may not react directly with the CFG on the cross-linker. This blocked form of the linkable functional group (BLFG) is often the preferred form of the CTBF because it may be less likely to form covalent linkages with the target biological molecule in the contacting step below.

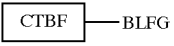

In the case where the BLFG is to be used in the contacting step, the de-protected or re-transformed form of the CTBF that it is capable or reacting with the CFG on the cross-linker is the form used in the cross-linking step below. By way of illustration, a CTBF may contain an aldehyde as a LFG or this aldehyde may be protected or transformed by reacting it with an O-amino alcohol to form an oxime (BLFG) as shown below.

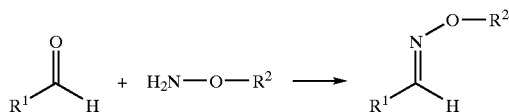

In this case the oxime would be considered the BLFG. It will be appreciated that more than one reaction or transformation to an LFG may be made. By way of further illustration an aldehyde may be reacted with an amine to form a Schiff base, which in turn may be reduced to a secondary amine. This may be still further reacted to form an amide, sulfonamide, urea, carbamate etc. All these transformations of the initial aldehyde are also considered BLFG's.

In the case where the CTBF (including the LFG) is first transformed or protected, the initial CTBF is sometimes referred to as a "precursor" while the transformed or protected form that is contacted with the TBM is referred to as a "monomer". Thus in the reaction illustrated above, the aldehyde may be called a precursor while the oxime is referred to as a monomer. In this case the oxime covalent bond (=N—O—) is referred to as the linking group (LG). It is often preferred that the monomer contain the same linking group (LG) as is present in the cross-linked form, described below, because some of the binding energy with the target may come from LG.

Examples of linkage or linkable functional groups include; aldehyde, ketone, primary amine, secondary amine, epoxide, carboxylic acid, sulfonic acid, alcohol (hydroxyl), isicyanate, isothiocyanate, halide and sulfonate. These functional groups may act as precursors of the blocked linkage functional groups.

Examples of CTBF's having blocked linkage or linkable functional groups are molecules containing Linkage Groups selected from; oxime, hydrazone, N-acyl hydrazone, secondary amine, tertiary amine, acetal, ketal, 1,2 amino alcohols, amide, N,N-disubstituted amides, thioamide, ureido, thioureido, carbamate, thiocarbamate, thiothiocarbamate, sulfonamide, carbamate, guanidino, amidino, thioester, ester, ether, 2-hydroxyether, 2-hydroxythioether, thioether, disulfide, alkane (alkylene), alkene (alkenylene) and alkyne (alkynylene). Preferred monomers will contain the above functional groups as LG's.

Steps b–d below may be combined into a single screening step that may be referred to as a first screening step, a pre-selection step or a pre-screening step.

(b) Contacting the candidate target binding fragments with a target biological molecule (TBM).

Contacting of the TBM with one or more members of the library may be conducted either individually or multiply. Preferably each candidate target binding fragment is contacted individually with the TBM. For example, this may conveniently be done in a 96 well format plate so that the formation of a complex with each member of the library can be conveniently evaluated without requiring any deconvolution step. The contacting step is often conducted at relatively high concentrations of the CTBF, so that Kd's as low as about 5 mM can be measured (see below).

The Target Biological Molecule (TBM) may be any biological molecule preferably of mammalian and most preferably of human origin. Optionally preferred TBM's may be human pathogen proteins such as viral proteins from viruses that infect human cells. Preferred TBM's are proteins most preferably secreted proteins. Preferred secreted proteins include; enzymes, cytokines, hormones, growth factors and their receptors. The TBM's may be isolated from natural sources or made recombinately in a host cell. Normally the atoms of the TBM will contain the natural abundance isotopes, but in some circumstances may be enriched. When the target is a receptor or a cell surface bound molecule, the TBM may conveniently be the extracellular domain or a derivative thereof.

In a preferred embodiment of the method, the Target Biological Molecule is not a single biological molecule; rather it is two or more molecules. For example, preferred TBM's may be protein-protein, protein-DNA/RNA, protein-substrate pairs. By way of illustration, a ligand-receptor pair may be the actual target when an ELISA or other biological assay requiring two or more biological molecules is used to measure a physical association (see below) such as binding or activity. The binding constant, IC50 or other measurement may result from the CTBF binding with either the Ligand, receptor or both. Similarly, when selected fragments are cross-linked (see below) and re-screened against the ligand-receptor pair, the recombined fragments may bind with the ligand, receptor or both.

(c) Measuring a change in a first physical association (PA-1) of the target biological molecule.

Measuring a change as used herein means any method capable of quantifying a physical association, including binding, of the CTBF with the TBM. A physical association (PA-1) of the target molecule includes a biological property such as binding with another biological molecule, signal transduction or catalysis of a reaction. It may also include any measurable physical chemical property such as a spectroscopic or magnetic property. Preferably the physical association will be suitable for rapid high throughput screening. The most preferred physical association measurement will be a biological one such as measuring binding or catalysis. An example of binding measurement would be an ELISA assay where protein-protein antagonism is measured.

(d) Selecting target binding fragments (TBF) based on (c).

Selecting target binding fragments (TBF) is based on the physical association measurement step. Selected TBF's will include those that bind relatively weakly with the TBM. Thus, for example in a binding assay such as ELISA, fragments that bind with no greater than a 5 mM affinity may be selected for. Most commonly the first selected CTBF's will bind to the target with an affinity of from 2 mM to 100 $\mu$M. TBF's or monomers that bind with a higher affinity e.g. Kd<50 $\mu$M are preferred, however such relatively high binding affinities are not necessary for selection for the cross-linking step.

(e) Reacting target binding fragments with a cross-linker, having chemically compatible cross-reactive group(s) with the LFG, under conditions suitable for forming a library of candidate cross-linked target binding fragments (CXL-TBF).

The selected target binding fragments, which individually normally bind to the target with relatively low affinity, are then cross-linked, normally in all combinations and permutations, to produce a library of candidate cross-linked target binding fragments (CXL-TBF). By way or illustration, If $TBF_m$ and $TBF_n$ are selected from the first screen, these molecules are then reacted with a suitable cross-linker such as a bifunctional linker (BFL) to form candidate cross-linked target binding fragments (CXL-TBF) for the second screening step according to the general equation:

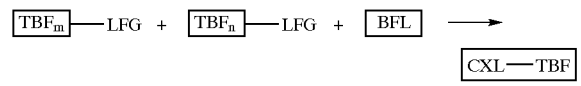

The BFL above will normally have two cross-reactive groups that are compatible with both LFG's, that is they will form stable covalent bond(s) (LG) with the LFG's under selected reaction conditions.

Each TBF may consist of two (or three) parts or moieties when LFG contains an atom capable of forming two (or three) bonds other than the linking group (LG) bond formed with the cross-linker. For example, when LFG is the carbonyl of a ketone, the carbonyl carbon may be bonded to two alkyl, aryl etc parts or moieties (part A and part B or part C and part D). This case may be represented generally by the diagram below where, for example, two ketones are cross-linked with an O,O'-diamino-alkanediol cross-linker to form a di-oxime:

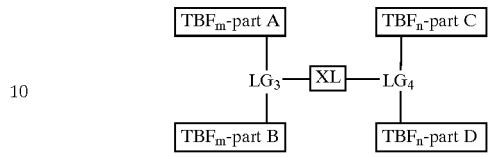

Here each of the two alkyl, aryl etc parts or moieties from the ketone are bonded to a nitrogen atom in the linking group (LG, =N—O—).

The CXL-TBF's are sometimes referred to as "dimers", however, they are truly only dimers when the cross-linking moiety (XL) is only a chemical bond. In the most general case these "dimers" will contain a linking moiety, such as an alkane, alkene, arylene, alkyl ether and the like bonded through one or more linking groups (LG) to the corresponding TMF's.

Reacting means chemically reacting so that a stable covalent bond or linking group LG is formed as the reaction product between the linkable functional group on the target binding fragment(s) and a chemically cross-reactive functional group (CFG) n the cross-linker. This step may be referred to as a cross-linking step or sometimes a combination" or "recombination" step.

Compatible functional group herein means capable of reacting with to form a stable LG.

The cross-linker is a small organic molecule having at least one cross-reactive functional group capable of reacting with the linkable functional group of at least one of the target binding fragments. Commonly, the cross-linker will have 2–4 such cross-reactive functional groups and most commonly 2 such groups. In this case the cross-linker is referred to as a bifunctional linker (BFL), either homo-bifunctional or hetero-bifunctional depending on whether the compatible functional groups are the same or different from one another.

In the case where the cross-linker has a single cross-reactive functional group, the candidate cross-linked target binding fragment, CXL-TBF, is simply the reaction product of these two molecules:

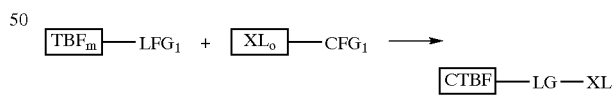

A simple example of such a reaction would be the product of an aldehyde and an amine. In this exemplary case R1 is a TBF and R2 Is XL where LFG-1 is an aldehyde and CFG-1 is a primary amine:

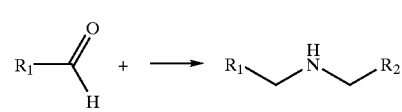

In this case LG is the resulting secondary amine, —(NH)—.

In the case where the cross-linker is a bifunctional linker, BFL, the linker has two cross-reactive linking groups and may be represented generally as:

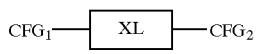

In this case, reacting two target binding fragments from the first screen above, each with its own linking functional group with the above BFL may be represented:

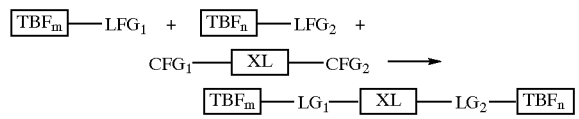

In the most general case of the above reaction, the two target binding fragments will have different linkable functional groups and will be linked by a hetero-bifunctional linker (het-BFL). In the most common case, both TBF will have the same CFG and will be linked by a homo-bifunctional linker (homo-BFL). In some cases, target binding fragments having different linkable functional groups may be linked with a homo-BFL and target binding fragments having the same linkable functional groups may be linked with a het-BFL.

Higher order linking groups such as tri- and tetra-functional linkers may also be employed in the method of this invention. By way of illustration a trifunctional linker such as that shown below may be used:

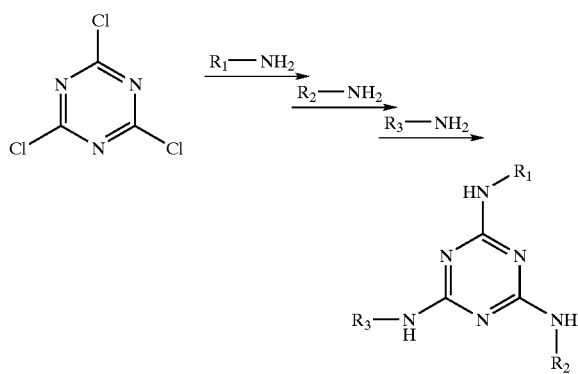

In each of the above cases, the product of the cross-linking reaction produces a candidate cross-linked target binding fragment(s) (CXL-TBF). These candidate molecules, typically with a molecular weight of 400–600 daltons, are then screened a second time against the target biological molecule.

Steps f–h below may be combined into a single screening step that may be referred to as a second screening step, a selection step or a final screening step.

(f) Contacting the candidate cross-linked target binding fragments with the target biological molecule.

Contacting of the TBM and one or more members of the library of candidate cross-linked target binding fragments (CXL-TBF) may be conducted either individually or multiply as before. Preferably each candidate cross-linked target binding fragment is contacted individually with the TBM.

The contacting step is usually conducted at lower concentrations of the CXL-TBF compared to CTBF's in the first screening step, so that Kd's in the micromolar or nanomolar range can be measured. The contacting format may be the same or different from that in the first or pre-screening step. Thus for example the two contacting steps may both be part of a binding assay (e.g. ELISA) or, for example, the second contacting step may be a functional activity assay or cell based binding assay.

(g) measuring a change in a second physical association (PA-2) of the target biological molecule.

The second physical association (PA-2) measurement for the CXL-TBF's may be the same as that used for the CTBF's or may be a different physical measurement. Preferably the second physical association measurement will be a biological measurement rather than a physical chemical measurement such as spectroscopic or the like.

(h) selecting cross-linked target binding fragments (XL-TBF) based of (g).

The cross-linked target binding fragments (XL-TBF) selected will typically have a Kd, IC-50 or the equivalent of 500 nM or better. These XL-TBF's are useful as drug lead pharmaceutical candidate molecules.

III Specific Chemistry

Many chemistries may be employed to produce linkable functional groups or to block or derivitize them. Similarly a wide array or linking chemistries are possible. Described below are a number of chemistries suitable for rapid high throughput screening. This description is meant to be illustrative and not limiting. In the description below the term "CTBF" is equivalent to "CTBF-part A" plus "CTBF-part B" defined above. Similarly, Linkable functional group is used interchangeably with linkage functional group.

The term "alkyl" means a cyclic, branched or unbranched saturated or unsaturated hydrocarbon radical having the number of carbons specified, or if no number is specified, up to 12 carbon atoms.

The term "aryl" means a homocyclic aromatic hydrocarbon radical having from 6–14 carbon atoms. Examples include phenyl, napthyl, biphenyl, phenanthrenyl, napthacenyl and the like.

The term "heteroaryl" means a heterocyclic aromatic radical having from 4–13 carbon atoms and from 1–6 heteroatoms selected from N, O, S and P.

The term "heterocycle" means a saturated or partially unsaturated cyclic radical having from 3–13 carbon atoms and from 1–6 heteroatoms selected from O, S, N and P.

The term "alkoxy" means an alkyl radical, as defined above, substituted with an oxo radical (—O—).

The term "acyl" means alkanoyl or alkylcarbonyl having from 1–12 carbon atoms.

The term "carboxy ester" means acyloxy or alkanoyloxy having from 1–12 carbon atoms.

The term "carboxamide" means alkylcarbonylamino having from 1–12 carbon atoms.

GENERAL NOTE: When CTBFs are employed with BLFGs, they may be prepared as described below from CTBFs containing the corresponding LFGs. Alternatively, it may be practical to purchase, otherwise acquire, or prepare by known methods the CTBFs with BLFGs using alternative chemistry.

Candidate Target Binding Fragments or Molecules (CTBFs)

1. Aldehyde and Ketone as the Linkage Functional Groups and the Corresponding Blocked Linkage Functional Groups (a). The linkage functional group is the carbonyl group present in an aldehyde or a ketone. These CTBFs may be available commercially, or may be prepared by a variety of known methods to those practiced in the art.

Aldehyde CTBFs are represented as follows.

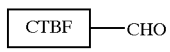

Ketone CTBFs are represented with two different parts (A and B) of the CTBF attached to ketone carbonyl as shown below.

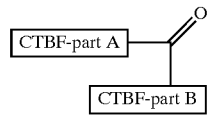

(b). Alternatively, the library is assembled with the oxime group as the blocked linkage functional group (BLFG). These CTBF's are prepared by condensation of aldehydes or ketones LFG's with an O-substituted hydroxylamine. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, heterocycle, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

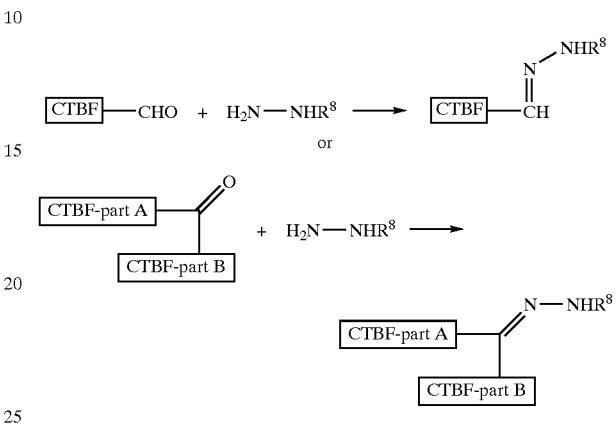

(d). Alternatively, the library is assembled with the N-acylhydrazone group as the BLFG. These CTBF's are prepared by condensation of aldehydes or ketone LFG's and an N-acyl hydrazine. Many reaction conditions are known to those practiced in the art (e.g., [March et al. supra, pp. 905–906] and [Li et al. *Chem. Biol.*, 1:37 (1994)]). X may be nothing, O, S, NH or $NR^9$. $R^8$ or $R^9$ may be H, or a straight chain or branched alkyl group of length 1 to 10, which may incorporate from 1 to 10 heteroatoms (N, O, P, S) within the chain. $R^8$ or $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ or $R^9$ may also be an aryl or heteroaryl group that is optionally substituted (alkyl, aryl, heteroaryl, carboxy ester, carboxamide, amino, N-acylamino, alkoxy, hydroxy, mercapto, phosphono).

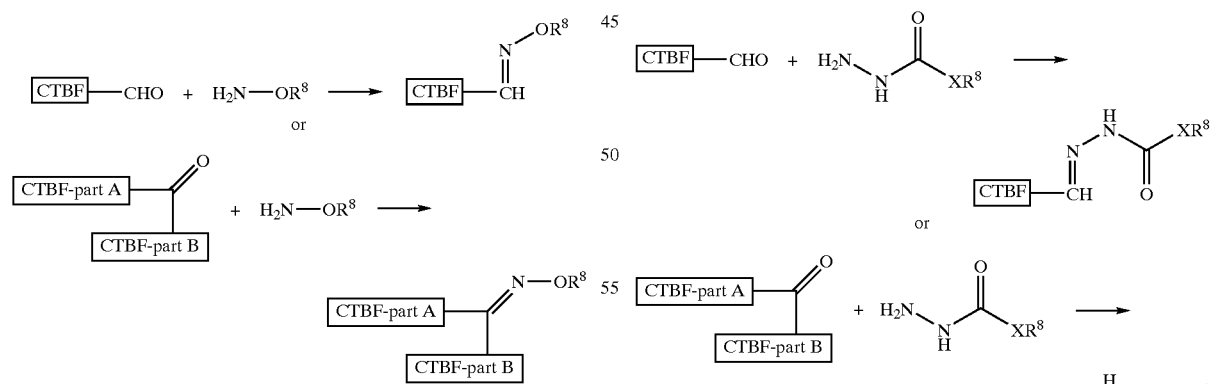

(c). Alternatively, the library is assembled with the hydrazone group as the BLFG. These CTBFs are prepared by condensation of aldehydes or ketones LFGs with an N-substituted hydrazine (March, *Advanced Organic Chemistry*, John Wiley & Sons, New York, 4th edition, 1992, pp. 904–906). $R^8$ may be H, or a straight chain or branched alkyl group of length 1 to 10, which may incorporate from 1 to 10

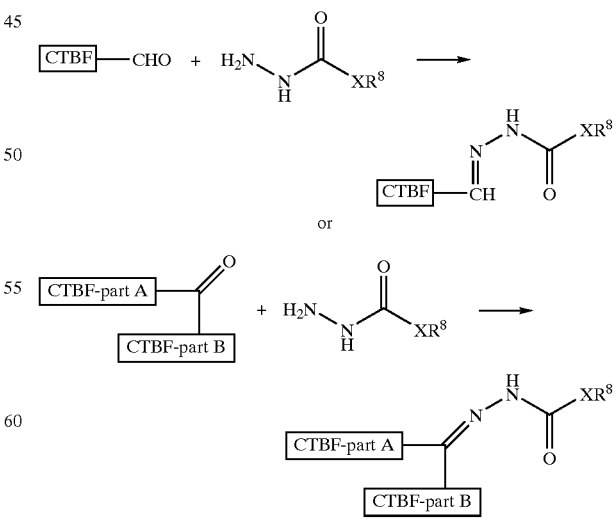

(e). Alternatively, the library is assembled with an amine group as the BLFG. These CTBF's are prepared by reductive amination of aldehydes or ketone LFGs. A large number of reducing agents could be employed that are known to those practiced in the art (March, et al. supra, pp. 898–900). $R^8$ or $R^9$ may be H, or a straight chain or branched alkyl group of length 1 to 10, which may incorporate from 1 to 10 heteroatoms (N, O, P, S) within the chain. $R^8$ or $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ or $R^9$ may also be an aryl or heteroaryl group that is optionally substituted (alkyl, aryl, heteroaryl, carboxy ester, carboxamide, amino, N-acylamino, alkoxy, hydroxy, mercapto, phosphono).

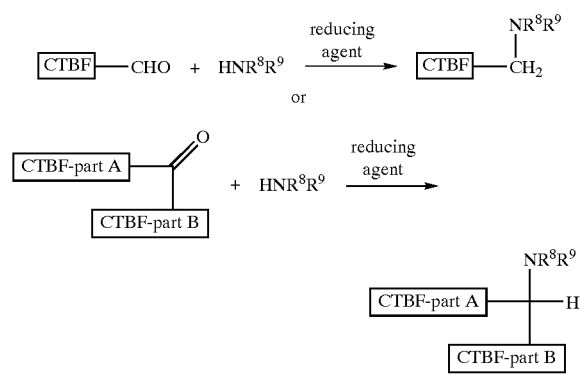

(f). Alternatively, the library is assembled with an acetal or ketal group as the BLFG. These CTBF's are prepared by condensing the aldehyde or ketone LFG's with a diol. Conditions for the preparation of acetals or ketals are known to those practiced in the art (March, et al. supra, pp. 889–891). $R^8$ may be a straight chain or branched alkyl group of length 2 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono). $R^8$ may be a straight chain or branched alkyl group of length 2 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

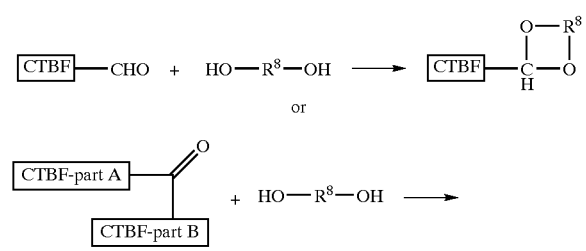

-continued

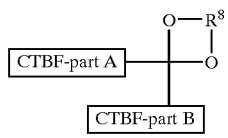

(g). Alternatively, the library BLFG's may be prepared by condensing the aldehyde or ketone LFGS with an amino alcohol or an amino thiol. Methods to prepare the product oxazolidines and thiazolidines are known to those practiced in the art (e.g., oxazolidines: Ede, et al. Tetrahedron Letters, 38: 7119–7122 (1997), and thiazolidines: Patek et al. Tetrahedron Letters, 36:2227–2230 (1995)). $R^8$ or may be a straight chain or branched alkyl group of length 2 to 10, which may incorporate from 1 to 10 heteroatoms (N, O, P, S) within the chain. $R^8$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono). $R^9$ may be H, or a straight chain or branched alkyl group of length 1 to 10, which may incorporate from 1 to 10 heteroatoms (N, O, P, S) within the chain. $R^9$ may also be appended with up to five $R^{11}$ groups ($R^{11}$ is alkyl, aryl, heteroaryl, carboxy ester, carboxamide, amino, N-acylamino, alkoxy, hydroxy, mercapto, phosphono, sulphono). $R^9$ may also be an aryl or heteroaryl group that is optionally substituted (alkyl, aryl, heteroaryl, carboxy ester, carboxamide, amino, N-acylamino, alkoxy, hydroxy, mercapto, phosphono).

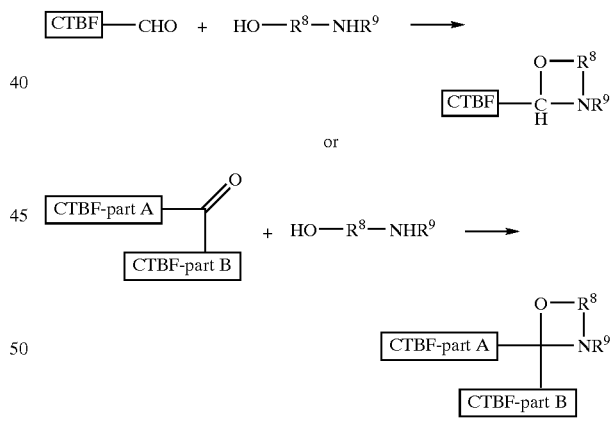

(h). Alternatively, the library is assembled with the alkene group as the blocked linkage functional group (BLFG). These CTBF's are prepared by condensation of aldehydes or ketone LFG's with phosphorous ylides (Maryanoff et al. *Chemical Reviews*, 89, 863–927 (1989). $R^8$ and $R^9$ may be H or a straight chain or branched alkyl group of length 2 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be an aryl or heteroaryl group that is optionally substituted (alkyl, aryl, heteroaryl, carboxamide, amino N-acylamino, alkoxy, hydroxy, mercapto, phosphono, sulphono). $R^8$ and $R^9$ may also be halogens and heteroatoms.

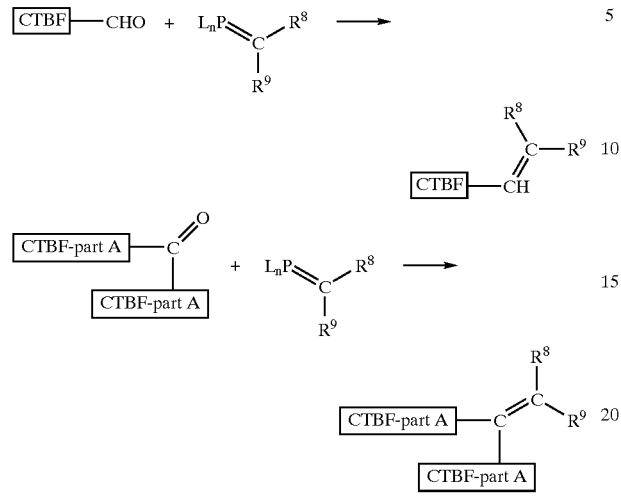

(i). Alternatively, carbanions, usually stabilized carbanions, may also be added into the carbonyl. Either the alcohol product A is obtained, or the hydroxyl group is eliminated to provide an alkene B. Numerous methods are available for performing this transformation (March et al., supra, 937–950).). $R^8$ and $R^9$ may be H or a straight chain or branched alkyl group of length 2 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be an aryl or heteroaryl group that is optionally substituted (alkyl, aryl, heteroaryl, carboxy ester, carboxamide, amino N-acylamino, alkoxy, hydroxy, mercapto, phosphono, sulphono). $R^8$ and $R^9$ may also be halogens and heteroatoms.

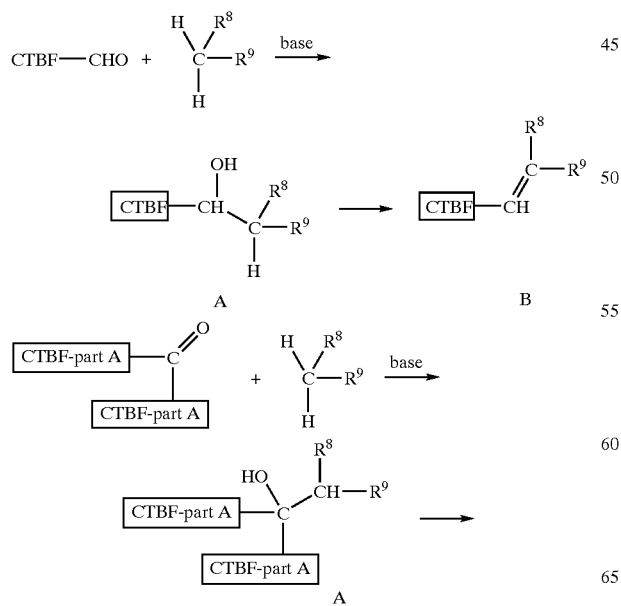

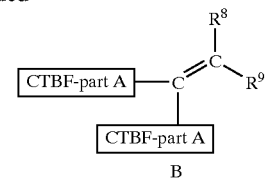

2. Primary and Secondary Amines as the Linkage Functional Groups and the Corresponding Blocked Linkage Functional Groups.

(a). The linkage functional group is the basic nitrogen of primary or secondary amines. These CTBF's may be available commercially, or may be prepared by a variety of known methods to those practiced in the art. CTBF's that have a primary amine LFG's are represented as follows.

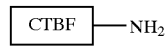

CTBF's that have a secondary amine LFG's are represented with two different parts (A and B) of the CTBF attached to the amine group as shown below.

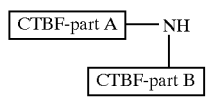

(b). Alternatively, the library may be assembled as secondary or tertiary amine BLFGs.

(i). CTBF's with secondary or tertiary amine BLFG's may be prepared by reductive amination of primary amine or secondary amine LFG's, respectively, with aldehydes and ketones. A large number of reducing agents could be employed that are known to those practiced in the art (March, et al. supra, pp. 898–900). $R^8$ or $R^9$ may be H, or a straight chain or branched alkyl group of length 1 to 10, which may incorporate from 1 to 10 heteroatoms (N, O, P, S) within the chain. $R^8$ or $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ or $R^9$ may also be an aryl or heteroaryl group that is optionally substituted -(alkyl, aryl, heteroaryl, carboxy ester, carboxamide, amino, N-acylamino, alkoxy, hydroxy, mercapto, phosphono). Numerous reductive amination methods may be used that are known to those practiced in the art.

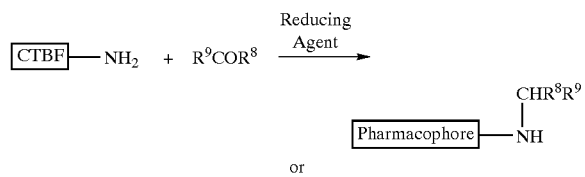

or

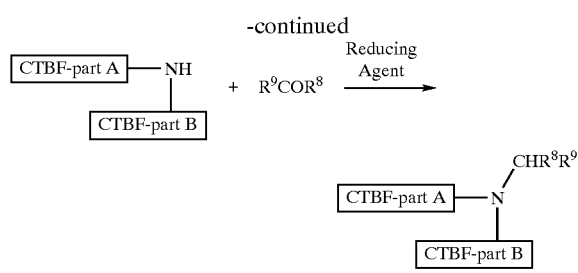

(ii). Alternatively, CTBF's with secondary or tertiary amine BLFG's may be prepared by reaction of primary or secondary amine LFG's, respectively, with an aryl, heteroaryl or alkyl group substituted with a leaving group X, where X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The halide could be attached to aromatic or heteroaromatic functionality on $R^8$, or it could be attached to an aliphatic group on $R^8$. When X is substituted upon aromatic and heteroaromatic functionality, an $S_NAr$ reaction or a palladium-mediated (or related transition metal mediated) amine coupling reaction would be performed [e.g., March, et al. supra, pp. 656–657; Wagaw et al., *J. Am. Chem. Soc.*, 119: 8451–8458 (1997) and references therein; and Ahman et al. *Tetrahedron Letters*, 38: 6363–6366 (1997)]. Where X is substituted upon alkyl functionality, an $S_N2$ or $S_N1$ reaction would be performed (March, et al., supra, pp. 411–413). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

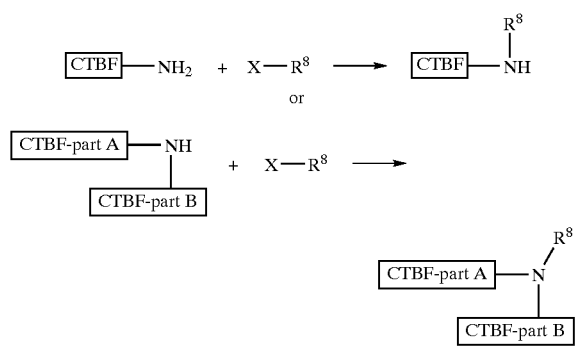

(iii). Alternatively, CTBF's with secondary or tertiary amine BLFG's may be prepared by reaction of primary or secondary amine LFG's, respectively, with a substituted epoxide (March, et al., supra, p. 416). Many epoxides are available commercially. Alternatively they can be prepared by a number of known methods to those practiced in the art, most preferably by epoxidation of an alkene. $R^8$ to $R^{11}$ may be H, or a straight chain or branched alkyl group of length 1 to 10, which may incorporate from 1 to 10 heteroatoms (N, O, P, S) within the chain. $R^8$ to $R^{11}$ may also be appended with up to five $R^{12}$ groups ($R^{12}$ is alkyl, aryl, halide, heteroaryl, carboxy ester, carboxamide, amino, N-acylamino, alkoxy, hydroxy, mercapto, phosphono, sulphono). $R^8$ to $R^{11}$ may also be an aryl or heteroaryl group that is optionally substituted (alkyl, aryl, halide, heteroaryl, carboxy ester, carboxamide, amino, N-acylamino, alkoxy, hydroxy, mercapto, phosphono).

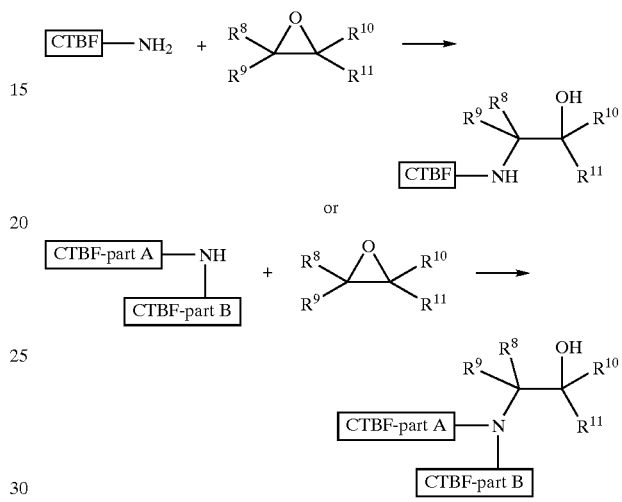

(c). Alternatively, the library may be assembled as amide or thioamide BLFG's. These CTBF's may be prepared by coupling primary and secondary amine LFG's with carboxylic acids (X=H), carboxylic acid derivatives (X=OR, SR, halide), or the corressponding thiocarboxylic acid derivatives (X=OR, SR, halide). Numerous methods are also available for coupling carboxylic acids and carboxylic acid derivatives with amines and are known to those practiced in the art [e.g., March, et al., supra, pp. 417–425; and Fields et al. *Int. J. Peptide Protein Res.* 35:181–187 (1990)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is halide, alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (halide, alkyl, aryl, halide, heteroaryl, carboxy ester, carboxamide, amino, N-acylamino, alkoxy, hydroxy, mercapto, phosphono).

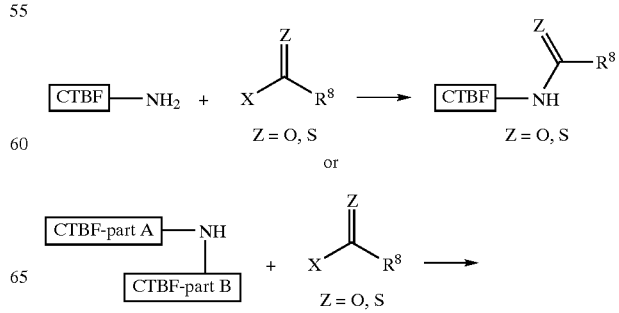

-continued

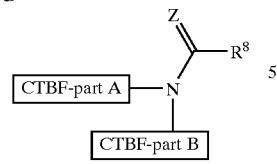

(d). Alternatively, the library may be assembled as urea or thiourea BLFG's.

(i). These CTBF's may be prepared by condensation of primary or secondary amine LFGs and isocyanates or isothiocyanates. The direct coupling of isocyanates and isothiocyanates with amines is known to those practiced in the art (March, et al., supra, p. 903). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono).

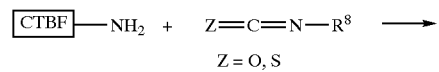

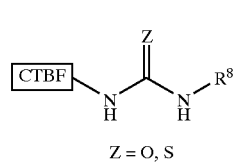

or

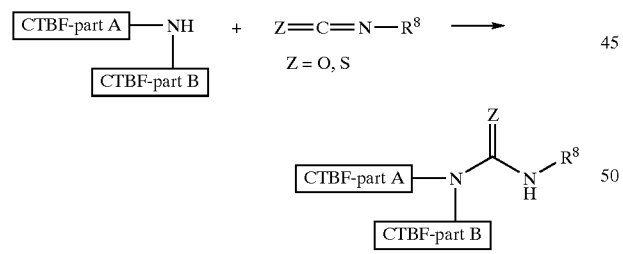

(ii). Alternatively, these CTBF's may be prepared by a two step process. In the first step, the primary or secondary amine LFG's is converted to carbamate (thiocarbamates) or related derivatives where X and Y are alkoxy groups, mercaptyl groups, halides, or other suitable leaving groups. In the second step a primary or secondary amine is added (e.g., Hutchins, *Tetrahedron Letters*, 35: 4055– 4058, (1994) and references therein). $R^8$ and $R^9$ may be H, or a straight chain or branched alkyl groups of length 1 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be aryl or heteroaryl groups that is optionally substituted (alkyl, aryl, heteroaryl, carboxy ester, carboxamide, amino N-acylamino, alkoxy, hydroxy, mercapto, phosphono).

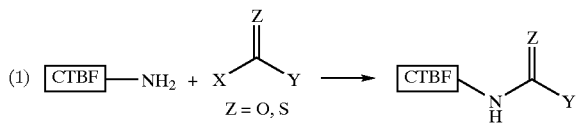

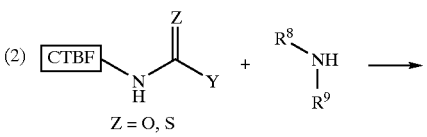

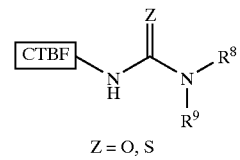

or

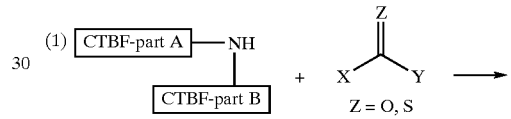

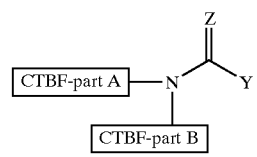

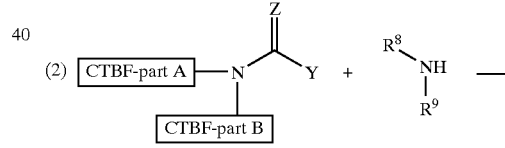

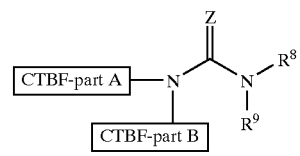

(iii). These CTBF's may also be prepared by condensation of primary or secondary amine LFG's and carbamates, thiocarbamates, or related derivatives where X is an alkoxy group, a mercaptyl group, or a halide (e.g., Hutchins, *Tetrahedron Letters*, 35: 4055–4058, (1994) and references therein). $R^8$ and $R^9$ may be H, or a straight chain or branched alkyl group of length 1 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be aryl or heteroaryl groups that are optionally substituted (alkyl, aryl, heteroaryl, carboxy ester, carboxamide, amino N-acylamino, alkoxy, hydroxy, mercapto, phosphono).

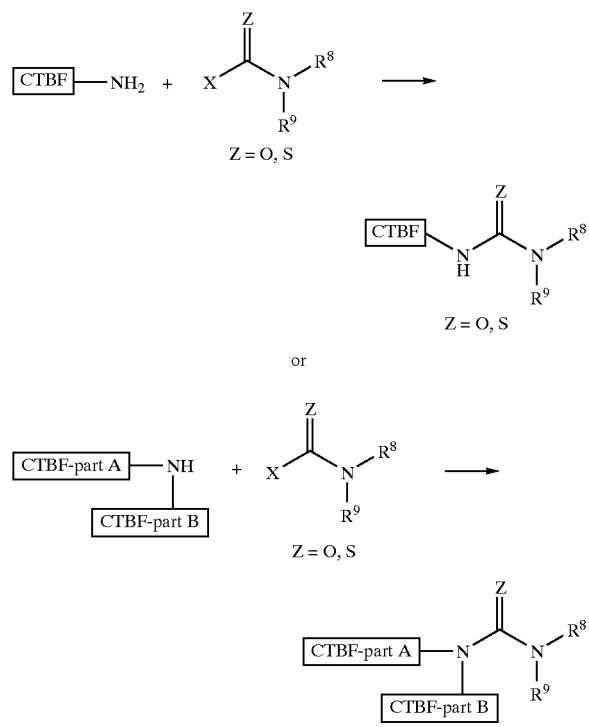

(d). Alternatively, the library may be assembled as sulfonamide BLFG's. These CTBF's may be prepared by coupling primary and secondary amine LFG's with sulfonic acids (X=H) or sulfonic acid derivatives (X=OR, SR, halide). Numerous methods are available for coupling sulfonic acids and sulfonic acid derivatives with amines and are known to those practiced in the art (e.g., March, et al., supra, p. 499, Greene, et al. *Protective Groups in Organic Synthesis*, John Wiley & Sons, New York, $2^{nd}$ edition, 1991, pp. 379–385). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is halide, alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (halide, alkyl, aryl, halide, heteroaryl, carboxy ester, carboxamide, amino, N-acylamino, alkoxy, hydroxy, mercapto, phosphono).

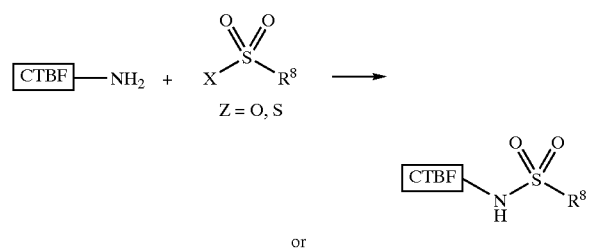

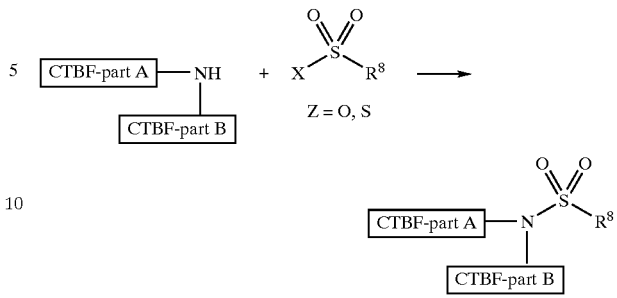

(e). Alternatively, the library may be assembled as carbamate, thiocarbamate or related BLFG's. These CTBF's may be prepared by condensation of primary and secondary amine pharmacophores with carbonyl derivatives (X=halide, OR, SR; Y=S, O; Z=S, O). Numerous methods are known to those practiced in the art (e.g., March, et al., supra, p. 418; and Greene, et al., supra, pp. 315–348). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono, sulfono).

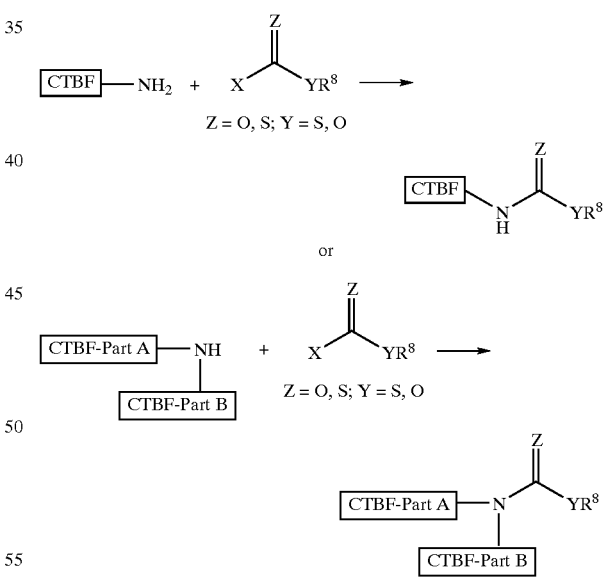

(f). Alternatively, the library may be assembled as guanidine BLFGs. These CTBFs may be prepared by condensation of primary and secondary amine pharmacophores with carbonyl derivatives (X=halide, OSO2R, OR, SR) [Roskamp, et al. *Tetrahedron*, 53:6697–6705 (1997)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono, sulfono).

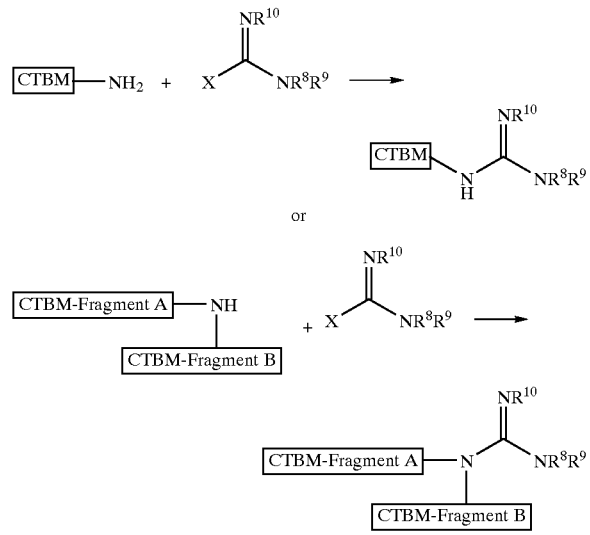

3. Epoxides as the Linkage Functional Groups and the Corresponding Blocked Linkage Functional Groups.

(a). The linkage functional group is the epoxide group. These CTBFs may be available commercially, or may be prepared by a variety of known methods to those practiced in the art.

Epoxide CTBFs are represented with four parts (A through D) of the CTBF attached to the epoxide group as shown below. Each fragment may be H, or functionality whereby a carbon atom is directly attached to the epoxide functionality.

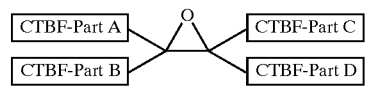

(b). Alternatively, the library may be assembled as 1,2-amino alcohol BLFGs. These CTBFs may be prepared by coupling epoxide LFGs with primary or secondary amines employing known methods to those practiced in the art (March, et al., supra, p. 416). $R^8$ or $R^9$ may be H, or a straight chain or branched alkyl group of length 1 to 10, which may incorporate from 1 to 10 heteroatoms (N, O, P, S) within the chain. $R^8$ or $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ or $R^9$ may also be an aryl or heteroaryl group that is optionally substituted (alkyl, aryl, heteroaryl, carboxy ester, carboxamide, amino, N-acylamino, alkoxy, hydroxy, mercapto, phosphono).

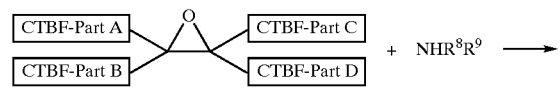

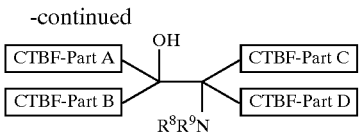

(c). Alternatively, the library may be assembled as, 2-hydroxy thioether BLFGs. These CTBFs may be prepared by coupling epoxide LFGs with thiols employing known methods to those practiced in the art (Wardell, in Patai The Chemistry of the Thiol Group, pt. 1; Wiley, New York, 1974, pp. 246–251). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono). The 2-hydroxy thioether BLFGs may also be readily oxidized to more water soluble 2-hydroxy sulfoxide or sulfone BLFGs (March, et al., supra, pp. 1201–1203).

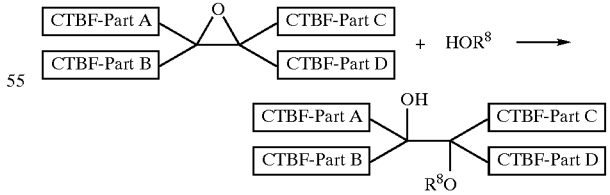

(d). Alternatively, the library may be assembled as,2-hydroxy ether BLFGs. These CTBFs may be prepared by coupling epoxide LFGs with alcohols employing known methods to those practiced in the art(March, et al., supra, p. 391). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

4. Carboxylic Acids as the Linkage Functional Groups and the Corresponding Blocked Linkage Functional Groups (a). The linkage functional group is the carboxylic acid. These CTBFs may be available commercially, or may be prepared by a variety of known methods to those practiced in the art.

Carboxylic acid CTBFs are represented as follows.

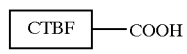

(b). Alternatively, the library may be assembled as amide BLFGs. These CTBFs may be prepared by coupling carboxylic acid LFGs (X=OH), or derivatives of carboxylic acid LFGs (X=OR, SR, halide) with primary or secondary amines. Numerous known methods are available for coupling carboxylic acids and carboxylic acid derivatives with amines to those practiced in the art [e.g., March, et al., supra, pp. 417–425; and Fields et al. *Int. J. Peptide Protein Res.* 35:181–187 (1990)]. $R^8$ and $R^9$ may be H, or a straight chain or branched alkyl group of length 1 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be an aryl or heteroaryl group that is optionally substituted (alkyl, aryl, halide, heteroaryl, carboxy ester, carboxamide, amino, N-acylamino, alkoxy, hydroxy, mercapto, phosphono).

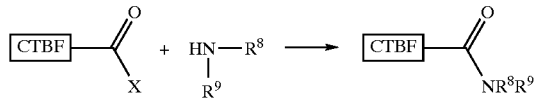

(c). Alternatively, amine BLFGs could be prepared by reduction of amide BLFGs prepared as described above in step 4b from the corresponding carboxylic acid LFGs. A number of reducing agents could be employed that are known to those practiced in the art (e.g., March, et al., supra, pp. 1212–1213). $R^8$ or $R^9$ may be H, or a straight chain or branched alkyl group of length 1 to 10, which may incorporate from 1 to 10 heteroatoms (N, O, P, S) within the chain. $R^8$ or $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ or $R^9$ may also be an aryl or heteroaryl group that is optionally substituted (alkyl, aryl, heteroaryl, carboxy ester, carboxamide, amino, N-acylamino, alkoxy, hydroxy, mercapto, phosphono).

(d). Alternatively, the library may be assembled as ester BLFGs.
(i). These CTBFs may be prepared by coupling carboxylic acid LFGs (X=OH), or derivatives of carboxylic acid LFGs (X=OR, SR, halide) with alcohols. Carboxylic acids and carboxylic acid derivatives may be coupled with alcohols employing numerous known methods to those practiced in the art [e.g., (March, et al., supra, pp. 392–398) and (e.g., Greene, et al., supra, pp. 227–228), and (Hughes et al. (Paquette, Series Editor in Chief), *Organic Reactions*, John Wiley & Sons, New York, 1992, vol. 42, pp. 343–347)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, halide, heteroaryl, carboxy ester, carboxamnide, amino, N-acylamino, alkoxy, hydroxy, mercapto, phosphono).

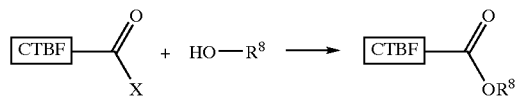

(ii). These CTBFs may be prepared by reacting carboxylic acid LFGs with an aryl, heteroaryl or alkyl group substituted with a leaving group X, where X may be a halide or a sulfonate group ($OSO_2R$ where R is substituted or unsubstituted alkyl or aryl, e.g. CH, $CF_3$, phenyl-$CH_3$ and phenyl-$NO_2$). The halide could be attached to aromatic or heteroaromatic functionality on $R^8$, or it could be attached to an aliphatic group on $R^8$. When X is substituted upon aromatic and heteroaromatic functionality, an $S_NAr$ reaction or a palladium-mediated, copper-mediated or related transition metal mediated coupling reaction would be performed. Where X is substituted upon alkyl functionality, an $S_N2$ or $S_N1$ reaction would be performed. Methods for these transformations are known to those practiced in the art [e.g., (March, et al., supra, pp. 398–399) and (e.g., Greene, et al., supra, pp. 228–229)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

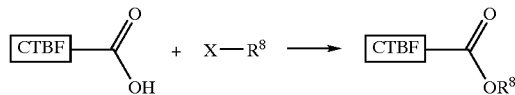

(e). Alternatively the library may be assembled as thioester BLFGs.
(i). These CTBFs may be prepared by condensation of carboxylic acid LFGs (X=OH), or carboxylic acid derivatives (X=OR, SR, halide) and thiols. Carboxylic acids and carboxylic acid derivatives may be coupled with thiols employing known methods to those practiced in the art (e.g., March, et al., supra, p. 409). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, halide, heteroaryl, carboxy ester, carboxamide, amino, N-acylamino, alkoxy, hydroxy, mercapto, phosphono).

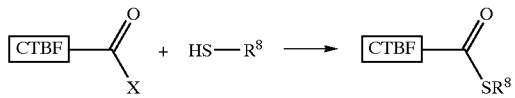

5. Sulfonic Acids as the Linkage Functional Groups and the Corresponding Blocked Linkage Functional Groups (a). The linkage functional group is the sulfonic acid. These CTBFs may be available commercially, or may be prepared by a variety of known methods to those practiced in the art.

Sulfonic acid CTBFs are represented as follows.

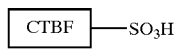

(b). Alternatively, the library may be assembled as sulfonamide BLFGs. These CTBFs may be prepared by reacting sulfonic acid LFGs (X=OH) or derivatives of sulfonic acids (X=halide, alkoxyl, mercaptyl) with amines (e.g., March, et al., supra, p. 499, Greene, et al. supra, pp. 379–385). $R^8$ and $R^9$ may be H, or a straight chain or branched alkyl group of length 1 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be an aryl or heteroaryl group that is optionally substituted (alkyl, aryl, heteroaryl, carboxy ester, carboxamide, amino N-acylamino, alkoxy, hydroxy, mercapto, phosphono).

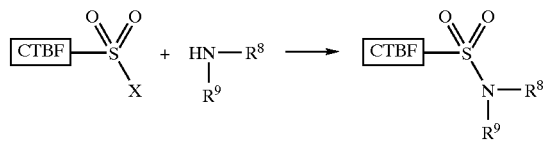

6. The Hydroxyl Group as the Linkage Functional Group and the Corresponding Blocked Linkage Functional Groups (a). The linkage functional group is the hydroxyl group. These CTBFs may be available commercially, or may be prepared by a variety of known methods to those practiced in the art.

Alcohol CTBFs are represented as follows.

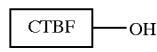

(b). Alternatively the library may be assembled as ether BLFGs.
(i). The ether may be prepared by reaction of an alcohol LFG with an aryl, heteroaryl or alkyl group substituted with a leaving group X, where X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The halide could be attached to aromatic or heteroaromatic functionality on $R^8$, or it could be attached to an aliphatic group on $R^8$. When X is substituted upon aromatic and heteroaromatic functionality, an $S_NAr$ reaction or a palladium-mediated, copper-mediated or related transition metal mediated coupling reaction would be performed [(e.g., March, et al., supra, pp. 654–655) and Hartwig et al., supra, pp. 8005–8008). Where X is substituted upon alkyl functionality, an $S_N2$ or $S_N1$ reaction would be performed. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

(ii). The ether may be prepared by the Mitsunobu reaction between alcohol LFGs and another alcohol where the second alcohol is acidic (pKa≦12), for example, phenols and oximes (Hughes et al.(Paquette, Series Editor in Chief), *Organic Reactions*, John Wiley & Sons, New York, 1992, vol. 42, pp. 335–636). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono). The key requirement on $R^8$ is that the alcohol has a pKa≦12,

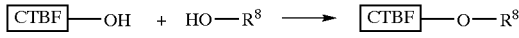

(iii). The ether may also be prepared by the Mitsunobu reaction between alcohol LFGs and another alcohol, where the alcohol LFGs are acidic ($pK_a<12$), for example, phenols or oximes (Hughes et al.(Paquette, Series Editor in Chief), *Organic Reactions*, John Wiley & Sons, New York, 1992, vol. 42, pp. 335–636). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). The key requirement on the pharmacophore substituted alcohol is that it has a $pK_a<12$,

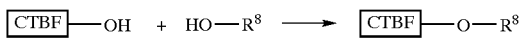

(c). Alternatively the library may be assembled as ester (Z=O) or thioester (Z=S) BLFGs. Alcohol LFGs may be coupled with carboxylic acids (Z=O, X=OH), carboxylic acid derivatives (Z=O, X=OR, SR, halide), or the corresponding thio-substituted derivatives (Z=S, X=OH, OR, SR halide). Carboxylic acids and carboxylic acid derivatives may be coupled with alcohols employing a variety of known methods to those practiced in the art [e.g., (March, et al., supra, pp. 392–398) and (e.g., Greene, et al., supra, pp. 227–228), and (Hughes et al. (Paquette, Series Editor in Chief), *Organic Reactions*, John Wiley & Sons, New York, 1992, vol. 42, pp. 343–347)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is halide, alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (halide, alkyl, aryl, halide, heteroaryl, carboxy ester, carboxamide, amino, N-acylamino, alkoxy, hydroxy, mercapto, phosphono).

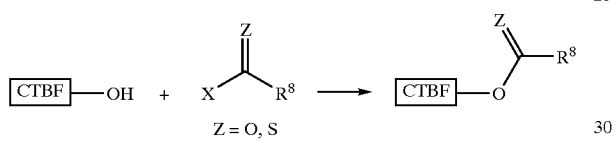

(d). Alternatively the library may be assembled from thioether BLFGs. The thioethers may be prepared by the Mitsunobu reaction between alcohol LFGs and a thiol (Hughes et al. (Paquette, Series Editor in Chief), *Organic Reactions*, John Wiley & Sons, New York, 1992, vol. 42, pp. 365–366, 381–382). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester,. carboxamide, amino, N-acylamino, alkoxy, hydroxy, mercapto, phosphono). The thioether BLFGs may also, be readily oxidized to more water soluble sulfoxide or sulfone BLFGs.

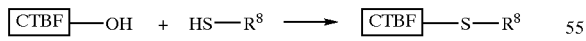

(e). Alternatively the library may be assembled as carbamate (Z=O) or thiocarbamate (Z=S) BLFGs.
  (i). These CTBFs may be prepared by condensation of alcohol LFGs and isocyanates or isothiocyanates. The direct coupling of isocyanates and isothiocyanates with alcohols is straightforward and obvious to those practiced in the art (March, et al., supra, pp. 891–892). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono).

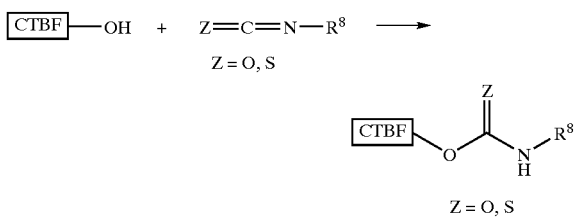

(ii). These CTBFs may be prepared by condensation of alcohol LFGs and carbamates, thiocarbamates, or related derivatives where X is an alkoxy group, a mercaptyl group, or a halide. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono).

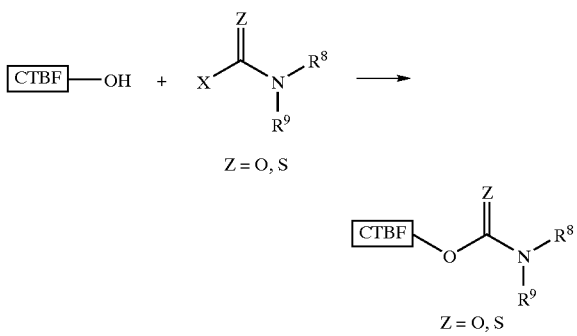

(iii). These CTBFs may be prepared in a two step process (e.g., March, et al., supra, p. 418; and Greene, et al., supra, pp. 315–348). In the first step, the alcohol LFGs are converted to carbonate (Z=O) or thiocarbonate (Z=S) or related derivatives where X and Y are alkoxy groups, mercaptyl groups, halides, or other suitable leaving groups. In the second step an amine is added to displace the leaving group Y. $R^8$ and $R^9$ may be H, or a straight chain or branched alkyl groups of length 1 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be an aryl or heteroaryl group that is optionally substituted (alkyl, aryl, heteroaryl, carboxy ester, carboxamide, amino N-acylamino, alkoxy, hydroxy, mercapto, phosphono).

(1) 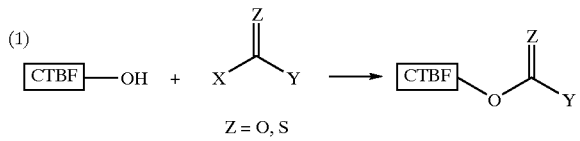

Z = O, S (2) 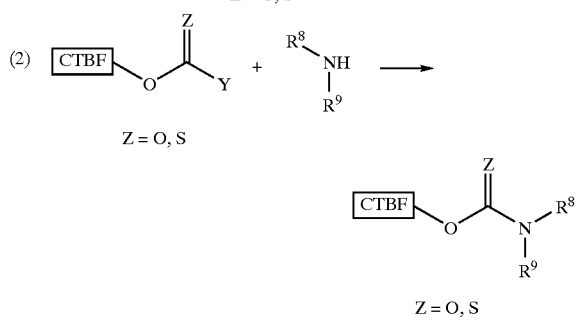

Z = O, S

Z = O, S (f). Alternatively the library may be assembled with thioester BLFGs. The thioesters may be prepared by the Mitsunobu reaction between alcohol LFGs and a thiol acid (Hughes et al.(Paquette, Series Editor in Chief), *Organic Reactions*, John Wiley & Sons, New York, 1992, vol. 42, pp. 343–347). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

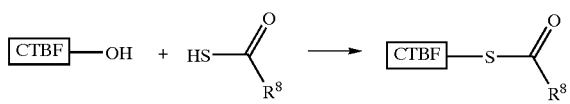

(g). Alternatively the library may be assembled with amide, thioamide., urea, thiourea, sulfonamide, carbamate, thiocarbamate (Z=$SO_2$, CO, CS, $CO_2$, COS, CSO, $CONR^{11}$, $CSNR^{11}$.) BLFGs. Substitution of the hydroxyl LFGs are accomplished using the Mitsunobu reaction [ e.g., (Hughes et al.(Paquette, Series Editor in Chief), *Organic Reactions*, John Wiley & Sons, New York, 1992, vol. 42, pp. 335–636) and (Fukuyama, et al., *Tetrahedron Letters*, 38: 5831–5834 (1997) and references therein)]. An aliphatic hydroxyl group is prefered. $R^8$ and $R^9$ may be H, or a straight chain or branched alkyl group of length 1 to 10, which may incorporate from 1 to 10 heteroatoms (N, O, P, S) within the chain. $R^8$ and $R^9$ may also be appended with up to five $R^{10}$ groups (RIO is alkyl, aryl, halide, heteroaryl, carboxy ester, carboxamide, amino, N-acylamino, alkoxy, hydroxy, mercapto, phosphono, sulphono). $R^8$ and $R^9$ may also be an aryl or heteroaryl group that is optionally substituted (alkyl, aryl, halide, heteroaryl, carboxy ester, carboxamide, amino, N-acylamino, alkoxy, hydroxy, mercapto, phosphono).

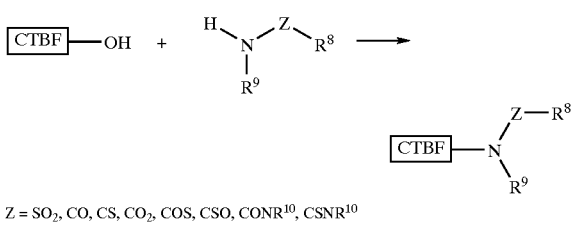

Z = $SO_2$, CO, CS, $CO_2$, COS, CSO, $CONR^{10}$, $CSNR^{10}$ (h). Alternatively, the library man be assembled with amine BLFGs. The amine BLFGs will be prepared from the BLFGs described in 6 g. The acyl or sulfonyl functionality may be removed by methods known to those practiced in the art (such as, acidic or basic hydrolysis, or dissolving metal reactions for sulfonamides Greene et al., supra, 349–357 and 379–385). Milder conditions may be applied to more specialized groups, e.g., trifluoroacetamides may be cleaved by mild basic hydrolysis (Greene et al., supra, 353–354), and nitrosubstituted benzenesulfonamides may be cleaved by thiolate addition) to provide secondary amines (Fukuyama, et al., *Tetrahedron Letters*, 38: 5831–5834 (1997) and references therein). Alternatively for some derivatives, reduction will provide tertiary amines (e.g., March, et al., supra, pp. 1212–1213).

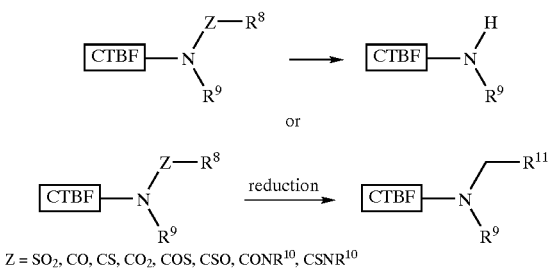

Z = $SO_2$, CO, CS, $CO_2$, COS, CSO, $CONR^{10}$, $CSNR^{10}$

7. The Thiol Group as the Linkage Functional Group and the Corresponding Blocked Linkage Functional Groups (a). The linkage functional group is the thiol group. These CTBFs may be available commercially, or may be prepared by a variety of known methods to those practiced in the art. Thiol CTBFs are represented as follows.

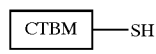

(b). Alternatively the library may be assembled as thioether BLFGs.

(i). The thioether may be prepared by reaction of a thiol LFG with an aryl, heteroaryl or alkyl group substituted with a leaving group X, where X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The halide could be attached to aromatic or heteroaromatic functionality on $R^8$, or it could be attached to an aliphatic group on $R^8$. When X is substituted upon aromatic and heteroaromatic functionality, an $S_NAr$ reaction or a palladium-mediated, copper-mediated or related transition metal mediated coupling reaction would be performed. Where X is substituted upon alkyl functionality, an $S_N2$ or $S_N1$ reaction would be performed. These methods are known to those practiced in the art [(March et al., supra, pp.407–409) and (Peach in Patai *The Chemistry of the Thiol Group, pt.* 1, John Wiley & Sons, New York, 1974, pp. 721–735)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono). The thioether BLFGs may also b oxidized to more water soluble sulfoxide and sulfone BLFGs (March, et al., supra, pp. 1201–1203).

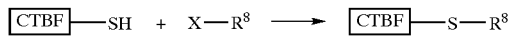

(ii). The thioether may also be prepared by the Mitsunobu reaction between alcohol LFGs and a thiol (e.g., (Hughes et al. (Paquette, Series Editor in Chief), *Organic Reactions*, John Wiley & Sons, New York, 1992, vol. 42, pp. 335–636). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, mercapto, phosphono, sulphono). The thioether BLFGs may also b oxidized to more water soluble sulfoxide and sulfone BLFGs (March, et al., supra, pp. 1201–1203).

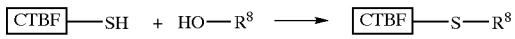

(c). Alternatively the library may be assembled with BLFGs whereby the thiol LFGs are acylated (March et al., supra, p. 409). Thiol LFGs may be coupled with carboxylic acids (Z=O, X=H), carboxylic acid derivatives (Z=O, X=OR, SR, halide), or the corresponding thio-substituted derivatives (Z=S, X=H, OR, SR halide). Carboxylic acids and carboxylic acid derivatives may be coupled with thiols employing known methods to those practiced in the art. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is halide, alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (halide, alkyl, aryl, halide, heteroaryl, carboxy ester, carboxamide, amino, N-acylamino, alkoxy, hydroxy, mercapto, phosphono).

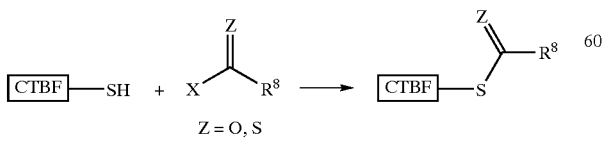

(d). Alternatively the library may be assembled as thio-carbamate (Z=O) or thiocarbamate (Z=S) BLFGs.

(i). These CTBFs may be prepared by condensation of thiol LFGs and isocyanates or isothiocyanates. The direct coupling of isocyanates and isothiocyanates with thiols is straighforward and obvious to those practiced in the art (Greene et al. supra, p. 301). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono).

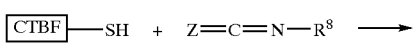
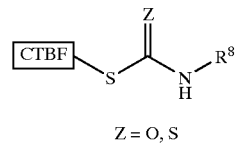

(ii). These CTBFs may be prepared by condensation of thiol LFGs and carbamates, thiocarbamates, or related derivatives where X is an alkoxy group, a mercaptyl group, or a halide. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulpheno). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono).

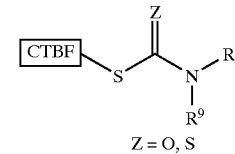

(iii). These CTBFs may be prepared in a two step process. In the first step, the thiol LFGs are converted to carbonate (Z=O) or thiocarbonate (Z=S) or related derivatives where X and Y are alkoxy groups, mercaptyl groups, halides, or other suitable leaving groups (Greene et al. supra, pp. 299–301). In the second step an amine is added to displace the leaving group Y. $R^8$ and $R^9$ may be H, or a straight chain or branched alkyl groups of length 1 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be an aryl or heteroaryl group that is optionally substituted (alkyl, aryl, heteroaryl, carboxy ester, carboxamide, amino N-acylamino, alkoxy, hydroxy, mercapto, phosphono).

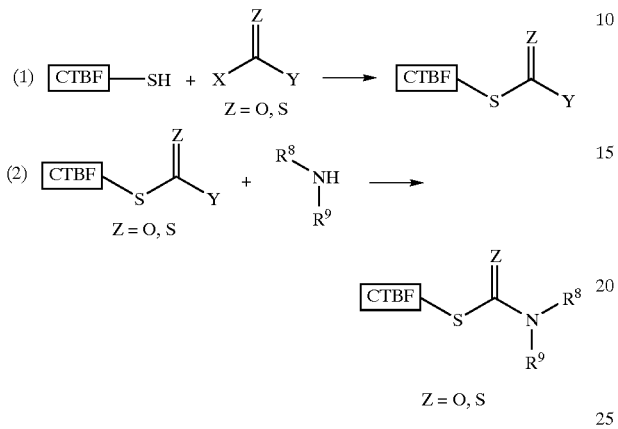

(e). Alternatively the library may be assembled as disulfide BLFGs. The disulfides may be prepared by reacting the thiol LFGs with thiols (X=H) or activated thiols (X=mercaptyl, halide, sulfonyl) employing known methods to those practiced in the art (e.g., Greene et al., supra, pp. 302–303). $R^8$ may be H, or a straight chin or branched alkyl group of length 1 to 10, which may incorporate from 1 to 10 heteroatoms (N, O, P, S) within the chain. $R^8$ may also be appended with up to five $R^9$ groups ($R^9$ is halide, alkyl, aryl, heteroaryl, carboxy ester, carboxamide, amino. N-acylamino, alkoxy, hydroxy, mercapto, phosphono, sulphono). $R^8$ may also be an aryl or heteroaryl group that is optionally substituted (halide, alkyl, aryl, halide, heteroaryl, carboxy ester, carboxamide, amino, N-acylamino, alkoxy, hydroxy, mercapto, phosphono).

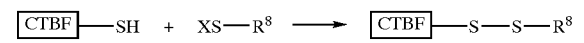

8. The Isocyanate or Isothiocyanate Group as the Linkage Functional Group and the Corresponding Blocked Linkage Functional Groups (a). The linkage functional group is the isocyanate (Z=O) or isothiocyanate (Z=S) group. These CTBFs may be available commercially, or may be prepared by a variety of known methods to those practiced in the art.

Isocyanate (Z=O) or isothiocyanate (Z=S) CTBFs are represented as follows:

(b). Alternatively the library may be assembled with urea or thiourea BLFGs by reaction of the isocyanate (Z=O) or isothiocyanate (Z=S) LFGs with amines (March et al., supra, p. 903). The direct coupling of isocyanates with amines is straighforward and known to those practiced in the art. $R^8$ and $R^9$ may be H, or a straight chain or branched alkyl groups of length 1 to 10, which may incorporate from 1 to 10 heteroatoms (N, O, P, S) within the chain. $R^8$ and $R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$ and $R^9$ may also be an aryl or heteroaryl group that is optionally substituted (alkyl, aryl, heteroaryl, carboxy ester, carboxamide, amino N-acylamino, alkoxy, hydroxy, mercapto, phosphono).

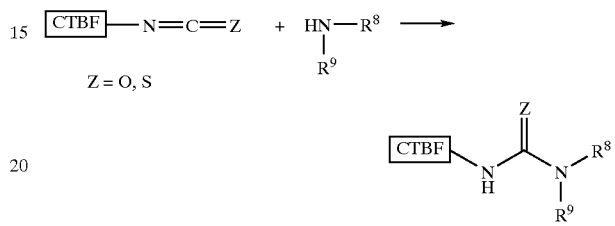

(c). Alternatively the library may be assembled as BLFGs by reaction of the isocyanate (Z=O) or isothiocyanate (Z=S) LFGs with thiols (Green et al., supra, p. 301). $R^8$ may be H, or a straight chain or branched alkyl groups of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono).

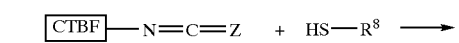

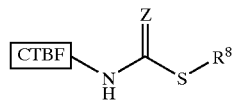

(d). Alternatively the library may be assembled as BLFGs by reaction of the isocyanate (Z=O) or isothiocyanate (Z=S) LFGs with alcohols (March et al, supra, pp. 891–892). $R^8$ may be H, or a straight chain or branched alkyl groups of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino N-acylamino, alkoxy, hydroxy, mercapto, phosphono).

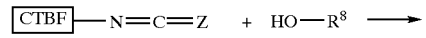

-continued

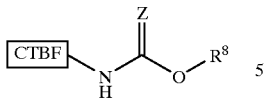

9. The Halide or Related Sulfonate Group as the Linkage Functional Group and the Corresponding Blocked Linkage Functional Groups (a). The linkage functional group is the halide leaving group or a similarly reactive sulfonate (X=OSO$_2$R where R is substituted or unsubstituted alkyl or aryl, e.g. CH$_3$, CF$_3$, phenyl-CH$_3$ and phenyl-NO$_2$) leaving group. These CTBFs may be available commercially, or may be prepared by a variety of known methods to those practiced in the art.

The halide and sulfonate (X=OSO$_2$R where R is substituted or unsubstituted alkyl or aryl, e.g. CH$_3$, CF$_3$, phenyl-CH$_3$ and phenyl-NO$_2$) CTBFs may be represented as follows.

(b). Alternatively the library may be assembled with amine BLFGs.

(i). The amine BLFGs may be prepared by substitution of the leaving group (X=halide or OSO$_2$R where R is substituted or unsubstituted alkyl or aryl, e.g. CH$_3$, CF$_3$, phenyl-CH$_3$ and phenyl-NO$_2$) with amines The leaving group may be attached to aromatic or heteroaromatic functionality, alkenyl functionality, or it could be attached to aliphatic functionality. A number of methods are known to those practiced in the art [e.g, March, et al. supra, pp. 656–657 and 411–413; Wagaw et al., *J. Am. Chem. Soc.*, 119: 8451–8458 (1997) and references therein; and Ahman et al. *Tetrahedron Letters*, 38: 6363–6366 (1997)]. When X is substituted upon aromatic and heteroaromatic functionality, an S$_N$Ar reaction may be performed. If the leaving group X is substituted upon aromatic, heteroaromatic or alkenyl functionality, a palladium-mediated (or related transition metal mediated) amine coupling reaction may be performed . Where X is substituted upon alkyl functionality, an SN2 or S$_N$1 reaction may be performed. R$^8$ or R$^9$ may be H, or a straight chain or branched alkyl group of length 1 to 10, which may incorporate from 1 to 10 heteroatoms (N, O, P, S) within the chain. R$^8$ or R$^9$ may also be appended with up to five R$^{10}$ groups (R$^{10}$ is alkyl, aryl, heteroaryl, carboxy ester, carboxamide, amino, N-acylamino, alkoxy, hydroxy, mercapto, phosphono, sulphono). R$^8$ or R$^9$ may also be an aryl or heteroaryl group that is optionally substituted (alkyl, aryl, heteroaryl, carboxy ester, carboxamide, amino, N-acylamino, alkoxy, hydroxy, mercapto, phosphono).

(ii). The amine BLFGs may also be prepared by a two step process. In the first step, substitution of the leaving group X with an amide, thioamide, urea, thiourea sulfonamide, carbamate, thiocarbamate (Z=SO$_2$, CO, CS, CO$_2$, COS, CSO, CONR$^{11}$, CSNR$^{11}$) is performed (see 0-0 below). X may be a halide or OSO$_2$R where R is substituted or unsubstituted alkyl or aryl, e.g. CH$_3$, CF$_3$, phenyl-CH$_3$ and phenyl-NO$_2$. The leaving group may be attached to aromatic or heteroaromatic functionality, alkenyl functionality, or it may be attached to aliphatic functionality. When X is substituted upon aromatic or heteroaromatic functionality, an S$_N$Ar reaction may be performed. When X is substituted upon aromatic, heteroaromatic, allylic or alkenyl a palladium-mediated (or related transition metal mediated) amine coupling reaction may be performed. Where X is substituted upon alkyl functionality, an S$_N$2 or S$_N$1 reaction may be performed. Methods are known to those practiced in the art (March et al., supra, pp.425–427). In the second step, the acyl or sulfonyl functionality may be removed by methods known to those practiced in the art (such as, acidic or basic hydrolysis, or dissolving metal reactions for sulfonamides (Greene et al., supra, 349–357 and 379–385). Milder conditions may be applied to more specialized groups, e.g., trifluoroacetamides may be cleaved by mild basic hydrolysis (Greene et al., supra, 353–354), and nitrosubstituted benzenesulfonamides may be cleaved by thiolate addition) to provide secondary amines (Fukuyama, et al., *Tetrahedron Letters*, 38: 5831–5834 (1997) and references therein). Alternatively for some derivatives, reduction will provide tertiary amines (e.g., March, et al., supra, pp. 1212–1213). R$^8$ to R$^{11}$ may be H, or a straight chain or branched alkyl group of length 1 to 10, which may incorporate from 1 to 10 heteroatoms (N, O, P, S) within the chain. R$^8$ to R$^{11}$ may also be appended with up to five R$^{12}$ groups (R$^{12}$ is alkyl, aryl, halide, heteroaryl, carboxy ester, carboxamide, amino, N-acylamino, alkoxy, hydroxy, mercapto, phosphono, sulphono). R$^8$ to R$^{11}$ may also be an aryl or heteroaryl group that is optionally substituted (alkyl, aryl, halide, heteroaryl, carboxy ester, carboxamide, amino, N-acylamino, alkoxy, hydroxy, mercapto, phosphono).

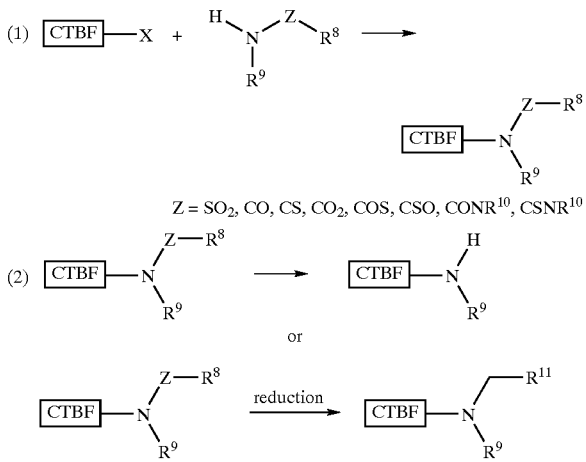

(c). Alternatively the library may be assembled with ether BLFGs. The ether BLFGs may be prepared by displacement of leaving group LFGs with an alcohol. X may be a halide or a sulfonate group (OSO$_2$R where R is substituted or unsubstituted alkyl or aryl, e.g. CH$_3$, CF$_3$, phenyl-CH$_3$ and phenyl-NO$_2$). The halide could be attached to aromatic or heteroaromatic functionality, alkenyl functionality, or it could be attached to an aliphatic functionality. When X is substituted upon aromatic or heteroaromatic functionality an $S_NAr$ reaction may be performed. When X is substituted on aromatic, heteroaromatic, allylic, or alkenyl functionality a palladium-mediated, Cu mediated, or related transtion metal mediated coupling reaction may be performed performed [(e.g., March, et al., supra, pp. 654–655) and Hartwig et al. Tetrahedron Lett., 38: pp. 8005–8008). Where X is substituted upon alkyl functionality, an $S_N2$ or $S_N1$ reaction may be performed (e.g., March, et al., supra, pp. 386–387 and 388–389). $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

heteroaromatic functionality, alkenyl functionality, or it could be attached to an aliphatic functionality. When X is substituted upon aromatic or heteroaromatic functionality an $S_NAr$ reaction may be performed. When X is substituted on aromatic, heteroaromatic, allylic, or alkenyl functionality a palladium-mediated, Cu mediated, or related transtion metal mediated coupling reaction may be performed. Where X is substituted upon alkyl functionality, an SN2 or $S_N1$ reaction may be performed. Methods for these transformations are known to those practiced in the art [e.g., (March, et al., supra, pp. 398–399) and (e.g., Greene, et al., supra, pp. 228–229)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

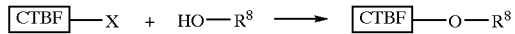

(d). Alternatively the library may be assembled with thioether BLFGs. The thioether BLFGs may be prepared by displacement of leaving group LFGs with an thiol. X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The halide could be attached to aromatic or heteroaromatic functionality, alkenyl functionality, or it could be attached to an aliphatic functionality. When X is substituted upon aromatic or heteroaromatic functionality an $S_NAr$ reaction may be performed. When X is substituted on aromatic, heteroaromatic, allylic, or alkenyl functionality a palladium-mediated, Cu mediated, or related transtion metal mediated coupling reaction may be performed. Where X is substituted upon alkyl functionality, an $S_N2$ or $S_N1$ reaction may be performed. These methods are known to those practiced in the art [(March et al., supra, 407–409) and (Peach in Patai *The Chemistry of the Thiol Group, pt.* 1, John Wiley & Sons, New York, 1974, pp. 721–735)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono). The thioether may also be oxidized to the more water soluble sulfoxide or sulfone BLFGs (March et al., supra, pp. 1201–1203).

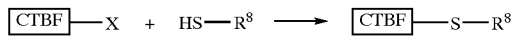

(e). Alternatively the library may be assembled with ester BLFGs. The ester BLFGs may be prepared by displacement of leaving group LFGs with a carboxylate. X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The halide could be attached to aromatic or

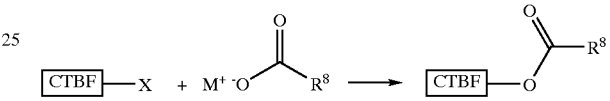

(f). Alternatively the library may be assembled with thiolester BLFGs. The ester BLFGs may be prepared by displacement of leaving group LFGs with a thiolacid. X may be a halide or a sulfonate group ($OSO_2R$ where R is substituted or unsubstituted alkyl or aryl, e.g. $CF_3$, $CF_3$, phenyl-$CH_3$ and phenyl-$NO_2$). The halide could be attached to aromatic or heteroaromatic functionality, alkenyl functionality, or it could be attached to an aliphatic functionality. When X is substituted upon aromatic or heteroaromatic functionality an $S_NAr$ reaction may be performed. When X is substituted on aromatic, heteroaromatic, allylic, or alkenyl functionality a palladium-mediated, Cu mediated, or related transtion metal mediated coupling reaction may be performed. Where X is substituted upon alkyl functionality, an $S_N2$ or $S_N1$ reaction may be performed. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

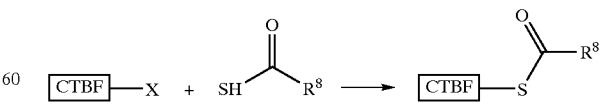

(g). Alternatively the library may be assembled with urea or thiourea BLFGs. These BLFGs may be prepared by displacement of leaving group LFGs with a primary or secondary ureas (Z=O) or thioureas (Z=S). X may be a halide or a sulfonate group ($OSO_2R$ where R is substituted or unsubstituted alkyl or aryl, e.g. $CH_3$, $CF_3$, phenyl-$CF_3$ and phenyl-$NO_2$). The halide could be attached to aromatic or heteroaromatic functionality, alkenyl functionality, or it could be attached to an aliphatic functionality. When X is substituted upon aromatic or heteroaromatic functionality an $S_NAr$ reaction may be performed. When X is substituted on aromatic, heteroaromatic, allylic or alkenyl functionality a palladium-mediated, Cu mediated, or related transtion metal mediated coupling reaction may be performed. Where X is substituted upon alkyl functionality, an $S_N2$ or $S_N1$ reaction may be performed. $R^8$ to $R^{10}$ may be H, or a straight chain or branched alkyl group of length 1 to 10, which may incorporate from 1 to 10 heteroatoms (N, O, P, S) within the chain. $R^8$ to $R^{10}$ may also be appended with up to five $R^{11}$ groups ($R^{11}$ is alkyl, aryl, heteroaryl, carboxy ester, carboxamide, amino, N-acylamino, alkoxy, hydroxy, mercapto, phosphono, sulphono). $R^8$ to $R^{10}$ may also be an aryl or heteroaryl group that is optionally substituted (alkyl, aryl, heteroaryl, carboxy ester, carboxamide, amino, N-acylamino, alkoxy, hydroxy, mercapto, phosphono).

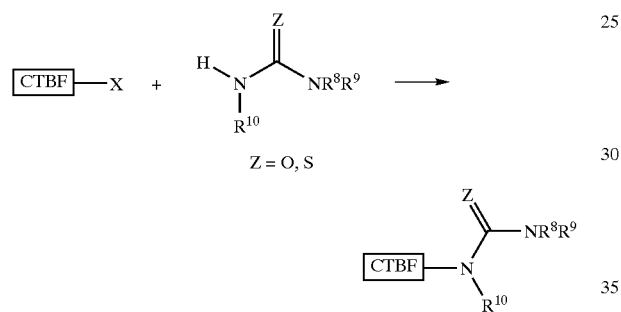

(h). Alternatively the library may be assembled with sulfonamide BLFGs. The sulfonamide BLFGs may be prepared by displacement of leaving group LFGs with a sulfonamide. X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The halide could be attached to aromatic or heteroaromatic functionality, alkenyl functionality, or it could be attached to an aliphatic functionality. When X is substituted upon aromatic or heteroaromatic functionality an $S_NAr$ reaction may be performed. When X is substituted on aromatic, heteroaromatic, allylic or alkenyl functionality a palladium-mediated, Cu mediated, or related transtion metal mediated coupling reaction may be performed. Where X is substituted upon alkyl functionality, an $S_N2$ or $S_N1$ reaction may be performed. These methods are known to those practiced in the art [(March et al., supra, pp.425–427) and (Fukuyama et al., *Tetrahedron Letters*, 38:5831–5834 (1997)]. $R^8$ may be a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

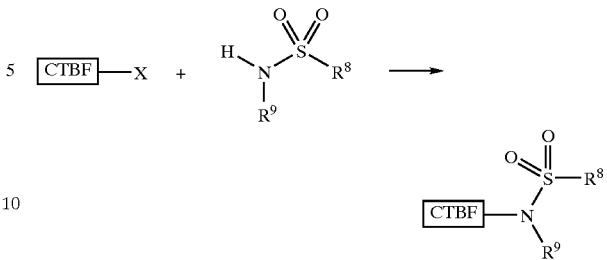

(i). Alternatively the library may be assembled with carbamate, thiocarbamate, or related BLFGs. These BLFGs may be prepared by displacement of leaving group with the corresponding carbamate, thiocarbamate, or related BLFGs. X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The halide could be attached to aromatic or heteroaromatic functionality, alkenyl functionality, or it could be attached to an aliphatic functionality. When X is substituted upon aromatic or heteroaromatic functionality an $S_NAr$ reaction may be performed. When X is substituted on aromatic, heteroaromatic, allylic or alkenyl functionality a palladium-mediated, Cu mediated, or related transtion metal mediated coupling reaction may be performed. Where X is substituted upon alkyl functionality, an $S_N2$ or $S_N1$ reaction may be performed. $R^8$ to $R^9$ may be H, or a straight chain or branched alkyl group of length 1 to 10, which may incorporate from 1 to 10 heteroatoms (N, O, P, S) within the chain. $R^8$ to $R^9$ may also be appended with up to five $R^{11}$ groups ($R^{10}$ is alkyl, aryl, heteroaryl, carboxy ester, carboxamide, amino, N-acylamino, alkoxy, hydroxy, mercapto, phosphono, sulphono). $R^8$ to $R^{10}$ may also be an aryl or heteroaryl group that is-optionally substituted (alkyl, aryl, heteroaryl, carboxy ester, carboxamide, amino, N-acylamino, alkoxy, hydroxy, mercapto, phosphono.

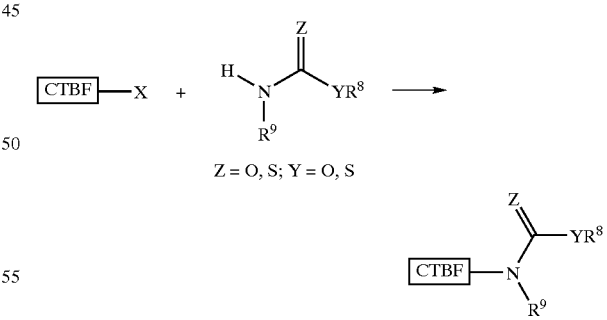

(j). Alternatively the library may be assembled by BLFGs where the leaving group is replaced with carbon-based functionality.
(i). X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The metal (M) may be any metal, but the prefered metals are $BL_n$, $SnL_n$, $ZnL_n$, $ZrL_n$, $CuL_n$, $SiL_n$, Ti $L_n$, Al $L_n$, and $L_n$ where L corresponds to metal ligands (e.g., halide, alkoxide, alkyl, aryl, alkenyl, heteroaryl, phosphine sulfide, amido) many of which are acceptable and are known to those practiced in the art. The halide could be attached to aromatic or heteroaromatic functionality, alkenyl functionality, or it could be attached to an aliphatic functionality. Addition can occur directly, or can be catalyzed by transition metals. Numerous methods are known to those practiced in the art [e.g. (Hegedus, L. S. (1994) in *Transition Metals in the Synthesis of Complex Organic Molecules* pp. 65–129, University Science Books, Mill Valley), (Knochel et al. *Chemical Reviews* 93:2117–2188 (1993)), (Miyaura et al. *Chemical Reviews* 95: 2457–2483 (1995)), and (Farina et al.(Paquette, Series Editor in Chief), *Organic Reactions*, John Wiley & Sons, New York, 1997, vol. 50, pp. 1–653)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

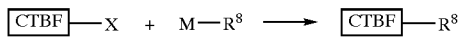

(ii). X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The BLFGs may be prepared in a two step process. In the first step, an organometallic reagent is prepared where the metal (M) may be any metal, but the prefered metals are $BL_n$, $SnL_n$, $ZnL_n$, $ZrL_n$, $CuL_n$, $SiL_n$, Ti $L_n$, Al $L_n$, and $L_n$ where L corresponds to metal ligands (e.g., halide, alkoxide, alkyl, aryl, alkenyl, heteroaryl, phosphine sulfide, amido) many of which are acceptable and are known to those practiced in the art. In the second step, carbon-carbon bond formation is performed to generate the BLFGs. Numerous methods for this two step process are known to those practiced in the art [e.g. (Hegedus, L. S. (1994) in *Transition Metals in the Synthesis of Complex Organic Molecules* pp. 65–129, University Science Books, Mill Valley), (Knochel et al. *Chemical Reviews* 93:2117–2188 (1993)), (Miyaura et al. *Chemical Reviews* 95: 2457–2483 (1995)), and (Farina et al.(Paquette, Series Editor in Chief), *Organic Reactions*, John Wiley & Sons, New York, 1997, vol. 50, pp. 1–653)]. $R^8$ may be H, or a straight chain or branched alkyl group of length 1 to 10, which may incorporate from 1 to 10 heteroatoms (N, O, P, S) within the chain. $R^8$ may also be appended with up to five $R^9$ groups ($R^9$ is alkyl, aryl, heteroaryl, carboxy ester, carboxamide, amino, N-acylamino, alkoxy, hydroxy, mercapto, phosphono, sulphono). $R^8$ may also be an aryl or heteroaryl group that is optionally substituted (alkyl, aryl, heteroaryl, carboxy ester, carboxamide, amino, N-acylamino, alkoxy, hydroxy, mercapto, phosphono).

(1) $\boxed{CTBF} - X \longrightarrow \boxed{CTBF} - M$

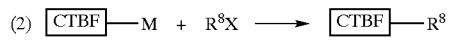

(iii). X may be a halide or a sulfonate group ($OSO_2R$ where R is substituted or unsubstituted alkyl or aryl, e.g. $CH_3$, $CF_3$, phenyl-$CH_3$ and phenyl-$NO_2$). The halide would preferably be attached to aromatic, heteroaromatic functionality, or alkenyl functionality. A palladium-mediated Heck reaction or related transtion metal mediated coupling reaction would be performed [e.g., (de Meijere, A. et al., *Angew. Chem. Int. Ed. Engl.*, 33:2379–2411 (1994) and references therein) and Heck, *Palladium Reagents in Organic Synthesis*, Academic Press, London 1985)]. For the alkene, $R^8$–$R^9$ may be straight chain or branched alkyl groups of length 1 to 10, which may incorporate from 1 to 10 heteroatoms (N, O, P, S) within the chain. $R^8$–$R^9$ may also be appended with up to five $R^{10}$ groups ($R^{10}$ is alkyl, aryl, heteroaryl, carboxy ester, carboxamide, amino, N-acylamino, alkoxy, hydroxy, mercapto, phosphono, sulphono). $R^8$–$R^9$ may also be aryl or heteroaryl groups that are optionally substituted (alkyl, aryl, heteroaryl, carboxy ester, carboxamide, amino, N-acylamino, alkoxy, hydroxy, mercapto, phosphono).

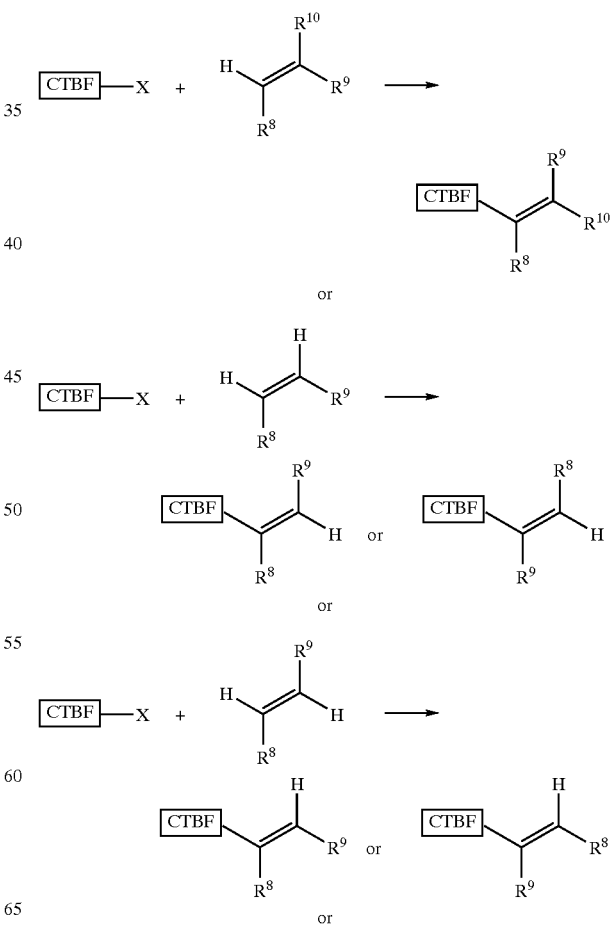

-continued

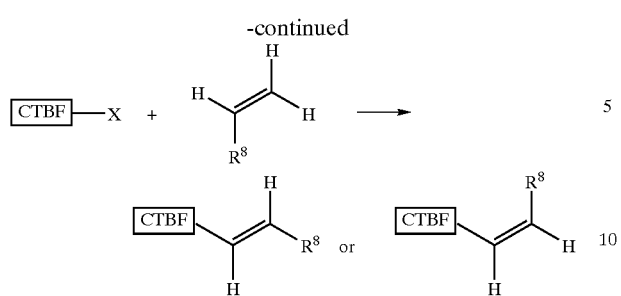

(iv). X may be a halide or a sulfonate group (OSO$_2$R where R is substituted or unsubstituted alkyl or aryl, e.g. CF$_3$, CF$_3$, phenyl-CH$_3$ and phenyl-NO$_2$). The halide would preferably be attached to aromatic, heteroaromatic functionality, or alkenyl functionality. A copper-mediated, palladium-mediated reaction, or related transtion metal mediated coupling reaction would be performed. Numerous methods are known to those practiced in the art [e.g., (March et al., supra, p. 481), (Sonagashira, K. in Comprehensive Organic Synthesis; Trost, B. M., Fleming, I., Eds.; Pergamon Press: New York, 1991, vol. 3 pp. 521–549), and (Rossi et al., Org. Prep. Proced. Int. 27:129–160 (1995)]. For the alkyne, R$^8$ may be H, straight chain or branched alkyl groups of length 1 to 10, which may incorporate from 1 to 10 heteroatoms (N, O, P, S) within the chain. R$^8$ may also be appended with up to five R$^9$ groups (R$^9$ is alkyl, aryl, heteroaryl, carboxy ester, carboxamide, amino, N-acylamino, alkoxy, hydroxy, mercapto, phosphono, sulphono). R$^8$ may also be a aryl or heteroaryl group that is optionally substituted (alkyl, aryl, heteroaryl, carboxy ester, carboxamide, amino, N-acylamino, alkoxy, hydroxy, mercapto, phosphono).

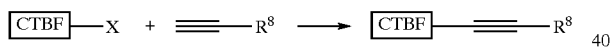

10. The Alkenyl Group as the Linkage Functional Group and the Corresponding Blocked Linkage Functional Groups (a). The linkage functional group is the alkenyl group. These CTBFs may be available commercially, or may be prepared by a variety of known methods to those practiced in the art.

CTBFs may be represented as follows, where as many as four CTBF fragments (A through D) may be present on the alkene functionality.

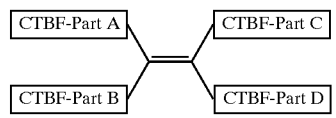

(b). Alternatively the library may be assembled with modified alkene BLFGs.

(i). The alkene BLFGs may be prepared by performing a transition metal-mediated (typically Pd) catalyzed Heck reaction or related reactions on trisubstituted, disubstituted or the vinyl functionalized CTBFs [e.g., (de Meijere, A. et al., Angew. Chem. Int. Ed. Engl., 33:2379–2411 (1994) and references therein) and Heck, Palladium Reagents in Organic Synthesis, Academic Press, London 1985)]. R$^8$ may be a straight chain or branched alkyl group of length 1 to 10, which may incorporate from 1 to 10 heteroatoms (N, O, P, S) within the chain. R$^8$ may also be appended with up to five R$^9$ groups (R$^9$ is alkyl, aryl, heteroaryl, carboxy ester, carboxamide, amino, N-acylamino, alkoxy, hydroxy, mercapto, phosphono, sulphono). R$^8$ may also be a aryl or heteroaryl group that is optionally substituted (alkyl, aryl, heteroaryl, carboxy ester, carboxamide, amino, N-acylamino, alkoxy, hydroxy, mercapto, phosphono). X may be a halide or a sulfonate group (OSO$_2$R where R is substituted or unsubstituted alkyl or aryl, e.g. CH$_3$, CF$_3$, phenyl-CH$_3$ and phenyl-NO$_2$).

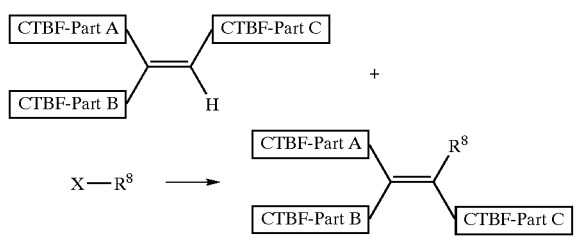

(ii). The alkene BLFGs may be prepared by performing a transition metal (typically Ru or Mo) catalyzed olefin metathesis reaction [e.g., (Grubbs et al. Accounts of Chemical Research 28:446–452 (1995)) and (Schuster et al. Angewandte Chemie-International Edition in English 36:2037–2056 (1997))]R$^8$–R$^{14}$ may be straight chain or branched alkyl groups of length 1 to 10, which may incorporate from 1 to 10 heteroatoms (N, O, P, S) within the chain. R$^8$–R$^{14}$ may also be appended with up to five R$^{10}$ groups (R$^{10}$ is alkyl, aryl, heteroaryl, carboxy ester, carboxamide, amino, N-acylamino, alkoxy, hydroxy, mercapto, phosphono, sulphono). R$^8$–R$^{14}$ may also be aryl or heteroaryl groups that are optionally substituted (alkyl, aryl, heteroaryl, carboxy ester, carboxamide, amino, N-acylamino, alkoxy, hydroxy, mercapto, phosphono).

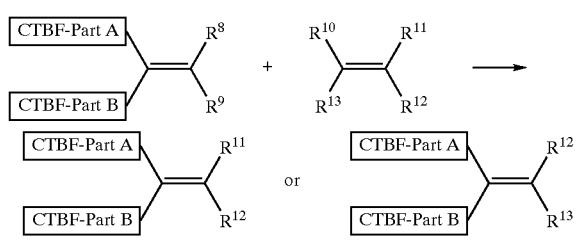

11. Methods to Covalently Bond TBFs using the LFG with a Bifunctional Linker (BFL) to Produce Candidate Crosslinked Target Binding Molecules (CXL-TBFs).

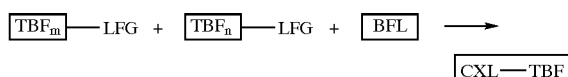

Upon identification of the TBFs, cross-linking is accomplished with a BFL. All of the chemistry described for preparation of the BLFGs could be employed in the crosslinking step. One method would be to crosslink TBFs that have the same LFGs and employing the same crosslinking chemistry. A second method would be to crosslink TBFs that have the same LFGs, but employing different crosslinking chemistry. A third method would be to crosslink TBFs that have different LFGs which is most but not all cases would require different crosslinking chemistry. Each of these strategies use known methods to those practiced in the art. Examples of the three methods are provided below.

Method 1. For example, two TBFs with aldehyde LFGs could be crosslinked employing a BFL that incorporates two O-substituted hydroxylamines.

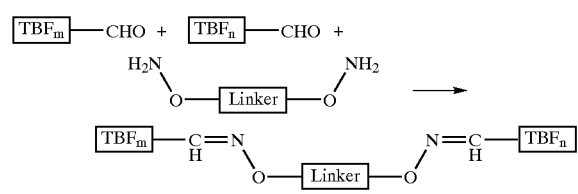

Method 2. For example, two TBFs with aldehyde LFGs could be crosslinked employing a BFL that incorporates one O-substituted hydroxylamine and one acyl hydrazide.

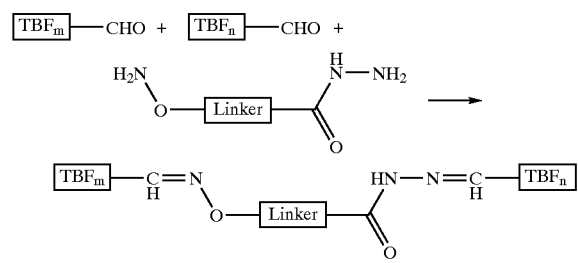

Method 3. For example, one TBF with an aldehyde LFG and one TBF with an amine LFG could be crosslinked employing a BFL that incorporates one O-substituted hydroxylamine and one carboxylic acid.

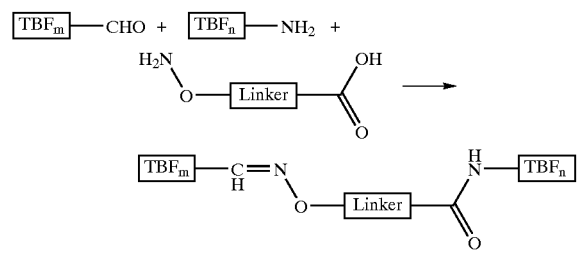

A hypothetical example for the preparation of heterolinkers would be to employ amino acids as heterolinkers. As shown below, the amino acid heterolinker serves to link TBFs with carboxylic acid LFGs to TBFs with amine LFGs. The amine LFG could be a primary amine or a secondary amine (not shown). Many methods that are known to those practiced in the art could be used to prepare the CXL-TBFs using amino acid heterolinkers. One of the methods is described below.

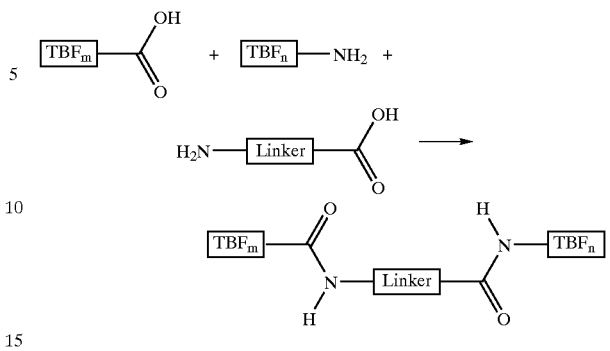

For this sample method, the amino acid BFL is protected as the N-tert-butoxycarbonyl (Boc) derivative. Many N-Boc amino acids are commercially available, e.g., Novabiochem (San Diego, Calif.) and Neosystems (Strosbourg, France). N-Boc protected amino acids can also be prepared by known methods to those practiced in the art (Bodansky et al., *The Practice of Peptide Synthesis*, Springer-Verlag, Berlin, 1984, 18–20).

The sample method is illustrated in Scheme 1. Sample experimental procedures are provided below.

Step 1 (Desai, et al., *Tetrahedron Letters*, 34, 7685–7688, (1993))

To a suspension of polymer-bound carbodimide (1.5 mmol) in chloroform (10 mL) is added the N-Boc protected amino acid 2 (0.55 mmol) and the amine-substituted TBF 1 (0.50 mmol). After the reaction mixture is shaken overnight at room temperature, the mixture is filtered. The resin is washed with chloroform (3×7.5 mL) and the combined filtrate is evaporated in vacuo to yield 3.

Step 2

To compound 3 (0.5 mmol) is added 5 mL of a solution of 4.0 M hydrochloric acid in dioxane (Aldrich, Milwaukee, Wis.). The solution is stirred for one hour at room temperature and then evaporated to remove the solvent and excess hydrochloric acid. The product is diluted with 5 mL of methanol and concentration is repeated to provide 4.

Step 3 (Desai, et al., *Tetrahedron Letters*, 34, 7685–7688, (1993))

To a suspension of polymer-bound carbodiimide (1.5 mmol) in chloroform (10 mL) is added intermediate 4 (0.50 mmol) and the carboxylic acid-substituted TBF 5 (0.55 mmol). After the reaction mixture is shaken overnight at room temperature the mixture is filtered. The resin is washed with chloroform (3×7.5 mL) and the combined filtrate is evaporated in vacuo to yield product 6, which is the desired CXL-TBF.

Scheme 1

Step 1:

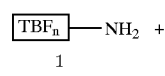

1

-continued

Step 2:

BocHN—Linker—C(=O)OH + [sphere]—N=C=N—Et →

BocHN—Linker—C(=O)—N(H)—TBF$_n$
3

BocHN—Linker—C(=O)—N(H)—TBF$_n$  —4M HCl in dioxane→
3

ClH$_3$N—Linker—C(=O)—N(H)—TBF$_n$
4

Step 3:

ClH$_3$N—Linker—C(=O)—N(H)—TBF$_n$   +
4

TBF$_m$—C(=O)OH + [sphere]—N=C=N—Et →
5

TBF$_m$—C(=O)—N(H)—Linker—C(=O)—N(H)—TBF$_n$
6

EXPERIMENTAL

Unless otherwise noted, materials were obtained from commercial suppliers and used without further purifications. Aldehydes were purchased from Aldrich Chemical Company, Inc. (Milwaukee, Wis.). Anhydrous dimethylsulfoxide (DMSO) and acetic acid were purchased from Fischer (Pittsburg, Pa.). Soluble CD4 (sCD4) was purchased from Intracel Corporation (Issaquah, Wash.), gp120 and anti-gp120 antibody were purchased from DuPont (Wilmington, Del.) and o-phenylenediamine peroxidase substrate tablet sets were purchased from Sigma Chemical Co. (St. Louis, Mo.). Reactions were carried out in commercially available Beckman 2 ml deep-well microtiter plates.

EXAMPLE 1

Pharmacophore Recombination for the Identification of Compounds Capable of Inhibiting the Interaction Between gp120 and CD4

To demonstrate the principle of pharmacophore recombination, we established a biochemical screen for the inhibition of gp120-CD4 binding. This assay measures the ability of small molecules to inhibit the binding of gp120 to sCD4 that is immobilized on a microtiter plate. Binding of sCD4 was quantified with an anti-gp120 antibody conjugated to horseradish peroxidase.

General Procedure for the Synthesis of an Oxime Compound Library

For several reasons, we chose to initially employ O-methyl oximes, rather than aldehydes, for the initial compound building block library. First, O-methyl oximes best model the pharmacophore units in the final oxime coupled dimers. Second, O-methyl oximes are more soluble in aqueous solution than their more hydrophobic aldehyde precursors. Also, the oxime functionality is clearly not inherently toxic and does not interfere with good pharmacokinetics or cell permeability since oximes are present in many drugs. Finally, the O-methyl oximes are easily prepared in a single step condensation of aldehydes with O-methyl hydroxylamine, without requiring purification of the resultant product. The chemical condensation of an aldehyde with O-methyl hydroxylamine to provide an oxime compound is shown in FIG. 1.

In the first step of the method, the initial oxime library was synthesized by separately condensing O-methyl hydroxylamine with 252 different aldehydes in a DMSO solution. The oxime library was prepared in a spatially separate fashion in a microtiter plate format such that each well contained a single oxime compound. More specifically, in each well of a microtiter plate, a DMSO solution of an unique aldehyde (0.188 ml, 0.15 M, 0.028 mmol) was added. To this solution, a DMSO solution of O-methyl hydroxylamine (0.083 ml, 0.5 M, 0.042 mmol) was then added followed by addition of a DMSO solution of acetic acid (0.023 ml, 0.5 M, 0.011 mmol). The plates were allowed to sit at room temperature overnight during which time condensation occurred, thereby providing the 252 member library of oxime compounds.

Assay to Determine which Oxime Compounds are Capable of Inhibiting the Interaction Between gp120 and CD4

The 252 member oxime compound library prepared as described above was then screened for the presence of compounds capable of inhibiting the interaction between gp120 and CD4 in a standard ELISA assay. For the gp120-CD4 ELISA assay, an Immulon-2 microtiter plate was incubated overnight at 4° C. with 70 ng of sCD4 in 100 µl of carbonate buffer. The solution was removed from the plate and washed three times with phosphate buffered saline (PBS) at pH 7.4, The plate was blocked with 150 µl PBS-Tween-BSA (0.5% BSA, 0.05% Tween-20) for 1 h at room temperature and then washed again. gp120 (1 ng) in 50 µl of PBS and 50 µl of test organic oxime compound (3 mM), 40 µl PBS, 10 µl were added and incubated for 1 h at room temperature. The plate was then washed and 100 µl of anti-gp120 conjugated horseradish peroxidase was added and incubated for 1 h at room temperature. The bound gp120 was then quantitated with o-phenylenediamine as a substrate.

Figure 2:
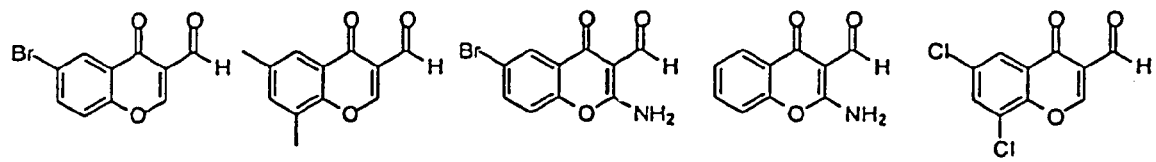
FIG. 2 shows a variety of organic aldehyde pharmacophore molecules which after conversion to methyl oximes were identified as being capable of inhibiting the interaction between CD4 and gp120.
Figure 2:
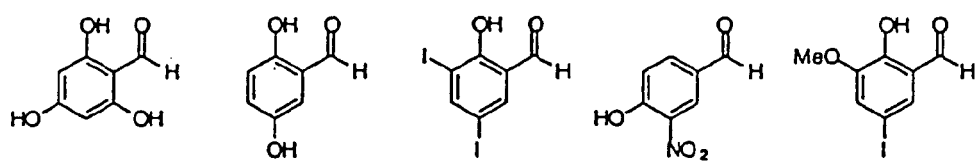
Figure 2:
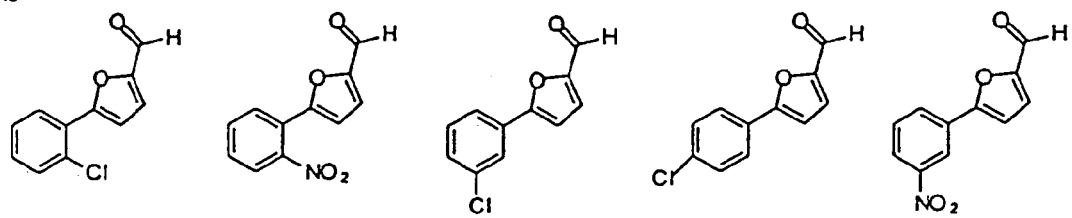
Figure 2:
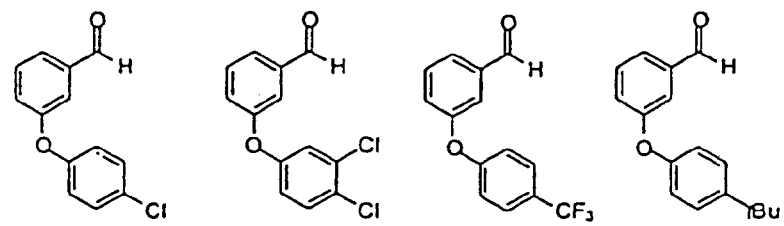
Figure 2:
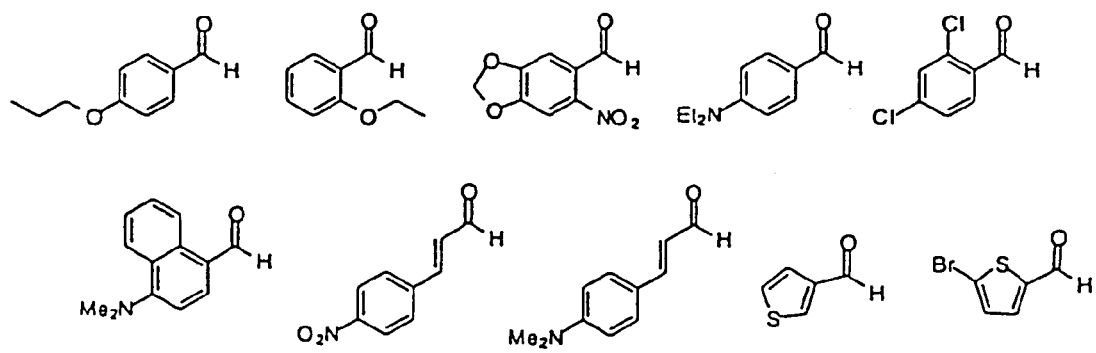
Figure 3:
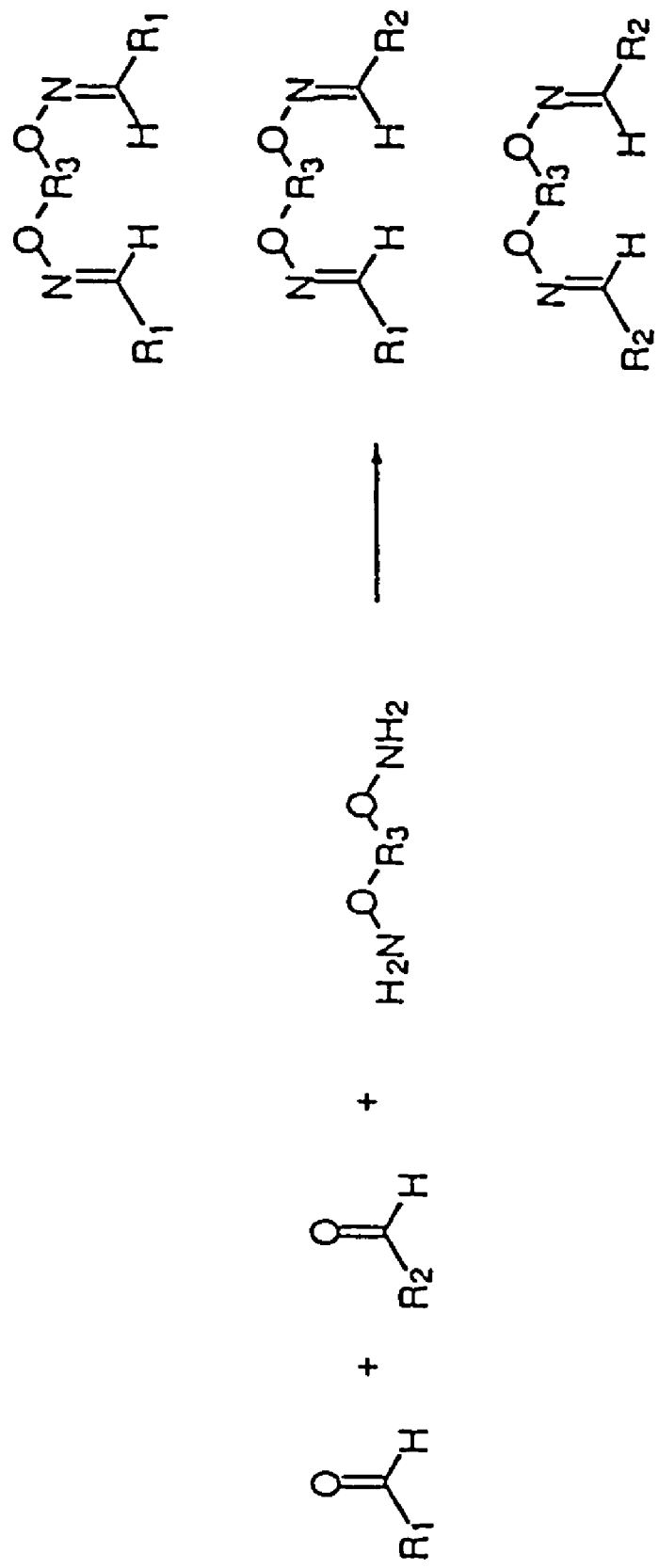
FIG. 3 shows chemistry useful for chemically coupling two aldehydes via an O,O'-diamino-alkanediol linker to produce both heterodimeric and homodimeric oxime compounds.
Figure 4:
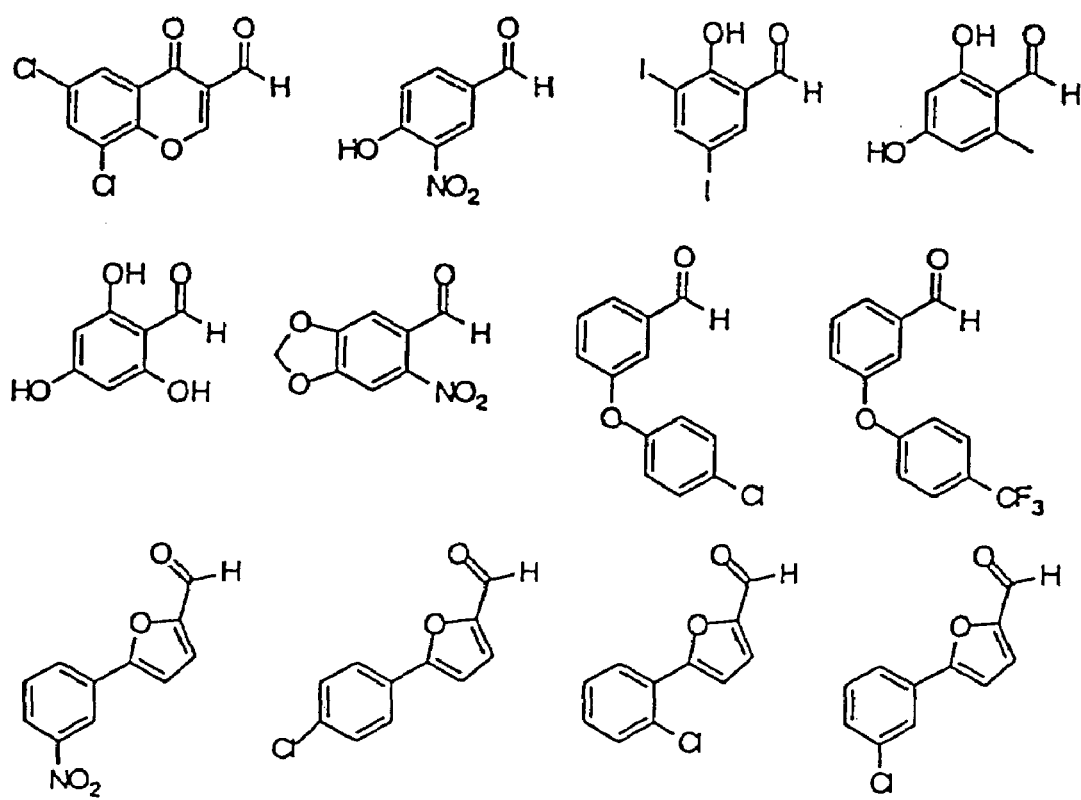
FIG. 4 shows a variety of aldehyde pharmacophores found to be highly efficient in dimeric form for inhibiting the interaction between CD4 and gp120.

The results of these assays demonstrated that 30 of the 252 oxime compounds were capable of inhibiting the interaction between gp120 and CD4, wherein the approximate $EC_{50}$ values ranged from about 20 µM to 500 µM. The structurally related aldehyde analogs of 30 of these oximes showed diverse structural motifs including chromones, phenols and furans (see FIG. 2).

Cross-Linking of the Top 30 Structurally Related Aldehyde Analogs to Produce a Library of Candidate Compounds and Screening of those Candidate Compounds for the Ability to Inhibit the Interaction Between gp120 and CD4

Each of the 30 structurally related aldehydes analogs corresponding to the 30 oxime compounds identified above as being capable of inhibiting the interaction between gp120 and CD4 were individually coupled to each of the other 29 aldehydes with a variety of linkers to produce a library of candidate compounds for binding to the target molecule. Each of the 30 individual aldehydes was linked with another aldehyde through an O,O'-diamino-alkanediol linker to obtain the library of cross-linked candidate compounds. Each aldehyde combination was kept spatially separate, but an equimolar mixture of five different O,O'-diamino-alkanediol linkers were used in each coupling reaction to provide a 450-member library of cross-linked candidate compounds. The chemistry used for preparation of the compounds is shown in FIG. 3 showing the synthesis of both homodimers and heterodimers.

The five linkers employed each consisted of two hydroxylamine groups tethered to an aliphatic chain having either two, three, four, five or six frethylene units. This allowed us to evaluate any distance dependency the two pharmacophores may have in the binding site. Linkers were prepared as follows. To a round-bottomed flask was added alkyl dibromide (20.2 mmol), N-hydroxyphthalimide (36.8 mmol, ~1.8 equiv) and dimethylformamide (90 ml). The flask was cooled to 0° C. and 1,8-diazabicyclo[5.4.0]undec-7-ene (40.5 mmol) was added dropwise with stirring. The reaction was allowed to warm to room temperature and was then stirred overnight. The reaction mixture was then poured into 1M HCl (500 ml). The resulting white solid precipitate was washed with water (3×50 ml) and methanol (3×50 ml) and sent onto the next step without further purification.

13.9 mmol of the crude bis-N-alkoxyphthalimide was then added to a round-bottomed flask in combination with dimethoxyethylene glycol (150 ml). To another flask was added hydrazine monohydrate (41.8 mmol, 3 equiv.) and dimethoxyethylene glycol (100 ml). The suspension of bis-N-alkoxyphthalimide was added slowly with stirring to the hydrazine solution. The flask was refluxed for 3 h, allowed to cool to room temperature and the resulting precipitate was filtered away. The remaining supernatant solution was concentrated and the resulting yellowish-oil was purified by Kugelrohr distillation (0.01 mm Hg, 60–70 ° C.) and column chromatography (89:9:2 $CHCl_3$/MeOH/$NH_4OH$).

For O,O'-diamino-1,4-butanediol), the general synthesis procedure described above was followed. IR (film from $CH_2Cl_2$): 3412.8, 3310.0, 2942.7, 2866.3 $cm^1$. $^1H$ NMR (400 MHz, $CDCl_3$): δ 5.31 (br s, 4H), 3.65 (m, 4H), 1.57 (m, 4H). $^{13}C$ NMR (400 MHz, $CDCl_3$): δ 75.5, 24.8, Anal. Calcd for $C_4H_{12}O_2N_2$: C, 39.99; H, 10.07; N, 23.32, Found: C, 40.17; H, 9.90; N, 23.12.

Once the five linkers were obtained, the 450 linked aldehyde combinations were prepared as follows. In each well, a DMSO solution of each of two different aldehydes (0.045 ml, 0.15 M, 0.007 mmol each) was added. To this solution, a DMSO solution of an equimolar mixture of the five linkers (0.025 ml, 0.3 M of each linker, 0.007 mmol) was added followed by a DMSO solution of acetic acid (0.005 ml, 0.5 M, 0.003 mmol). The plates were allowed to sit at room temperature overnight to allow for potential ligand formation.

Each of the 450 members of the potential ligand library was then tested at a concentration of 100 μM each (i.e., a concentration that is 10-fold more dilute than the concentration employed in the initial oxime monomer screen) for the ability to inhibit the interaction between gp120 and CD4 using the ELISA assay described above. The results from these assays demonstrated that more than 300 of the 450 members of the potential ligand library showed greater than 50% inhibition activity at the concentration employed. When the 450 members of the potential ligand library were tested at a concentration of 1 μM each for the ability to inhibit the interaction between gp120 and CD4, 17 of the ligands showed greater than 50% inhibitory activity at that concentration. The chemical structures of 12 of the 17 most active aldehyde precursors are shown in FIG. 4.

Evaluation of Linker Length Dependence on Activity

The 17 linked aldehyde combinations with the greatest activity were then resynthesized as described above with a unique linker per well (85 separate wells) so as to evaluate any linker-length dependency on binding. Screening each of the 85 ligand compounds at 1 μM each showed that ligands that incorporated pharmacophore 1 (see FIG. 5) were more potent than the other ligands and that there indeed was a dependence upon linker length. Specifically, ligands with linkers having either 4 or 5 methylene units were much more active than ligands with linkers having 6 methylene units, whereas ligands with linkers having either 2 or 3 methylene units were only slightly more active than ligands with linkers having either 4 or 5 methylene units.

Biological and Analytical Characterization of Representative Ligands

One of the ligands that exhibited strong activity for inhibiting the interaction between gp120 and CD4 (as shown in FIG. 6) was resynthesized with each of the five different linkers on a large scale and was then purified by column chromatography. Column chromatography purification enabled isolation of the heterodimer from the homodimer.

Large scale synthesis of organic oxime compounds was performed as follows. To a flame-dried round-bottomed flask was added aldehyde (0.82 mmol) and DMSO (8 ml). A 0.9 M O-methyl hydroxylamine (1.4 ml) was then added and the reaction mixture was allowed to stir at room temperature overnight. The reaction was poured into methylene chloride (50 ml), washed with $H_2O$ (3×20 ml), dried and concentrated. Silica gel chromatography provided the pure organic oxime compounds.

The oxime compounds made by this method were characterized as follows.

(1) O-methyl oxime of 6-nitropiperonal

Reaction of 6-nitropiperonal with O-methyl hydroxylamine provided predominantly one oxime isomer which was purified by silica gel chromatography (10:90, EtOAc/hexanes). $^1H$ NMR (400 MHz, $CDCl_3$): δ 8.61 (s, 1H), 7.53 (s, 1H), 7.37 (s, 1H), 6.15 (s, 2H), 4.00 (s, 3H). Anal. Calcd for $C_9H_8O_5N_2$: C, 48.22; H, 3.60; N, 12.50, Found: C, 48:40; H, 3.75; N, 12.56.

(2) O-methyl oxime of 6,8-dichloro-3-formylchromone

Reaction of 6,8-dichloro-3-formylchromone provided 1:1 cis/trans isomers which were isolated by silica gel chromatography (20:80, $CH_2Cl_2$/hexanes).

Isomer 1: $^1H$ NMR (400 MHz, $CDCl_3$): δ 8.48 (s, 1H), 8.24 (s, 1H), 8.12 (d, 1H, J=2.5), 7.75 (d, 1H, J=2.5), 3.97 (s, 3H). Anal. Calcd for $C_{11}H_7O_3NCl_2$: C, 48.56; H, 2.59; N, 5.15, Found: C, 48.44; H, 2.47; N, 5.03.

Isomer 2: $^1H$ NMR (400 MHz, $CDCl_3$): δ 9.45 (s, 1H), 8.12 (d, 1H, J=2.5), 7.75 (d, 2H, J=2.5), 4.07 (3H). Anal. Calcd for $C_{11}H_7O_3NCl_2$: C, 48.56; H, 2.59; N, 5.15, Found: C, 48.45; H, 2.49; N, 5.11.

Large scale synthesis of oxime ligands was performed as follows. To a flame-dried round-bottom flask was added 10 ml of DMSO and 1.03 mmol of each of the two aldehydes to be incorporated into the ligand. After all solids were dissolved, a solution of the appropriate linker (1.24 mmol) in 1 ml of DMSO was added dropwise, followed by the addition of acetic acid (0.72 mmol). The reaction mixture was allowed to stir at room temperature overnight. The reaction was then poured into methylene chloride (50 ml), washed with $H_2O$ (3×20 ml), dried and concentrated. Silica gel chromatography provided the isolated homo/heterodimers. Cis/trans isomers, when present, were not separated and were purified as mixtures of isomers. The oxime dimers made by this method were characterized below.

(1) Oxime heterodimer of 6,8-dichloro-3-formyl-chromone and 6-nitropiperonal, linker containing 4 methylene units The heterodimer was separated from the homodimers by silica gel chromatography (20:80, EtOAc/hexanes). The heterodimer was isolated and characterized as a 1:1 mixture of cis/trans isomers. Anal. Calcd for $C_{22}H_{17}O_8N_3Cl_2$: C, 50.59; H, 3.28; N, 8.05, Found: C, 50.70; H, 3.40; N, 7.89.

Isomer 1: $^1$H NMR (400 MHz, $CDCl_3$): δ 9.42 (s, 1H), 8.55 (s, 1H), 8.00 (s, 1H), 7.67 (m, 2H), 7.39 (s, 1H), 7.27 (s, 1H), 6.09 (s, 2H), 4.22 (m, 4H), 1.84 (m, 4H).

Isomer 2: $^1$H NMR (400 MHz, $CDCl_3$): δ 8.54 (s, 1H), 8.41 (s, 1H), 8.16 (s, 1H), 7.99 (s, 1H), 7.67 (s, 1H), 7.40 (s, 1H), 7.24 (s, 1H), 6.08 (s, 2H), 4.22 (m, 4H), 1.83 (m, 4H).

(2) Oxime heterodimer of 6.8-dichloro-3-formyl-chromone and 6-nitropiperonal, linker containing 5 methylene units The heterodimer was separated from the homodimers by silica gel chromatography (20:80, EtOAc/hexanes). The heterodimer was isolated and characterized as a 1.5:1 mixture of cis/trans isomers. Anal. Calcd for $C_{23}H_{19}O_8N_3Cl_2$: C, 51.51; H, 3.57; N, 7.83, Found: C, 51.68; H, 3.70; N, 7.66.

Isomer 1: $^1$H NMR (400 MHz, $CDCl_3$): δ 8.62 (s, 1H), 8.47 (s, 1H), 8.24 (s, 1H), 8.10 (s, 1H), 7.74 (s, 1H), 7.73 (s, 1H), 7.37 (s, 1H), 6.14 (s, 2H), 4.20 (m, 4H), 1.8 (m, 4H), 1.53 (m, 2H).

Isomer 2: $^1$H NMR (400 MHz, $CDCl_3$): δ 9.47 (s, 1H), 8.61 (s, 1H), 8.11 (s, 1H), 7.75 (s, 2H), 7.48 (s, 1H), 7.33 (s, 1H), 6.14 (s, 2H), 4.30 (t, 2H, J=6.6), 4.20 (m, 2H), 1.80 (m, 4H), 1.53 (m, 2H).

Figure 5:
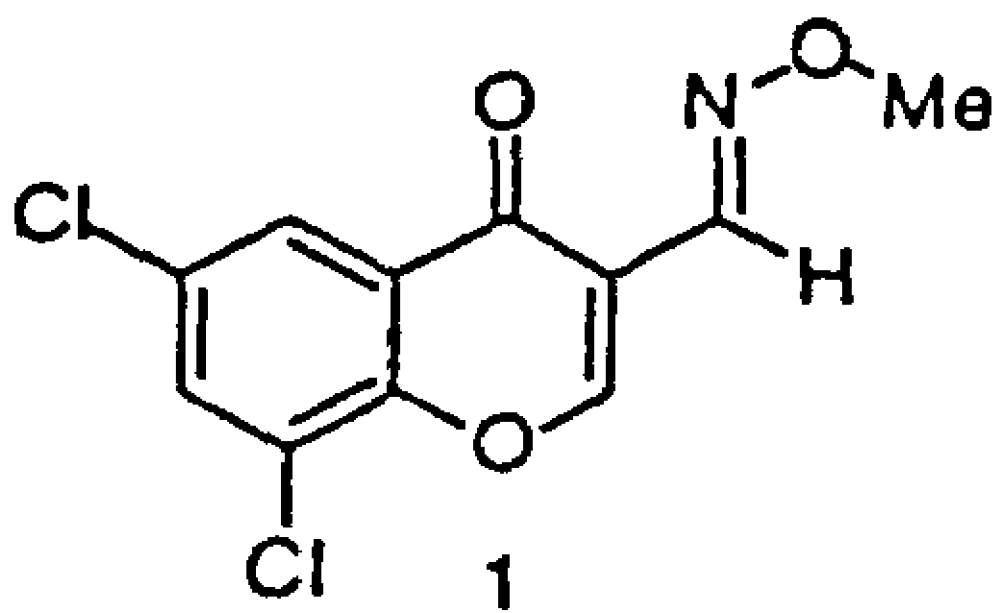
FIG. 5 shows an O-methyl oxime compound found to be particularly effective in dimeric form for inhibiting the interaction between CD4 and gp120.
Figure 6:
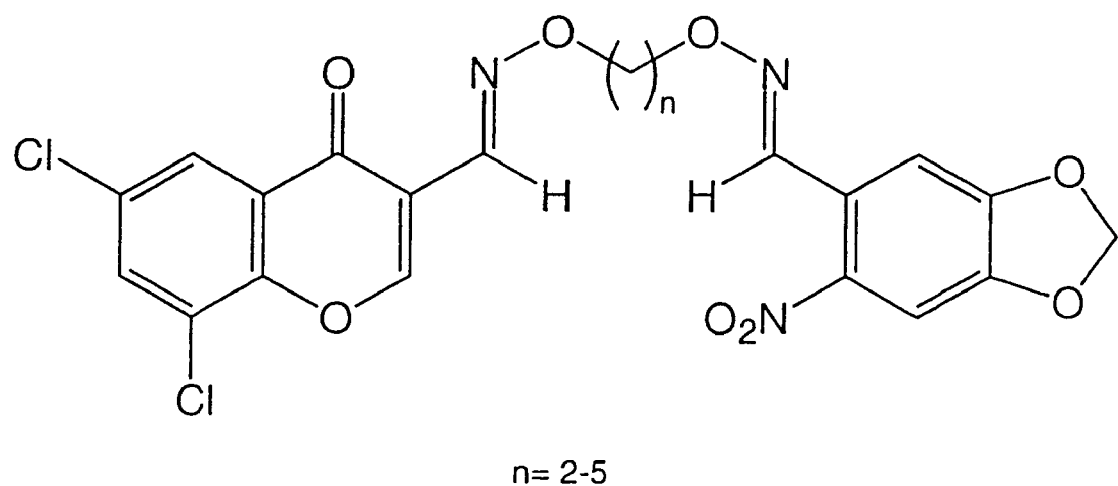
FIG. 6 shows a specific ligand having particularly high activity for inhibiting the interaction between CD4 and gp120.

These purified heterodimers and homodimers were then tested as described above for the ability to inhibit the interaction between gp120 and CD4, The results of these assays demonstrated that heterodimers shown in FIG. 6 having a linker containing from 2 to 5 methylene units exhibited $EC_{50}$'s ranging from 0.6 to 1.5 μM and showing 10- to 20-fold enhancement in inhibitory activity over the compound shown in FIG. 5 ($EC_{50}$ in the range of about 10–15 μM). The other compound that was incorporated into the heterodimer had an $EC_{50}$ of greater than 50 μM.

The heterodimers shown in FIG. 6 having linkers containing from 2 to 5 methylene units are of comparable potency to the most potent compounds that have been identified to date that block the CD4/gp120 interaction (Tanaka et al., *J. Antibiotics* 50:58 (1997), Sun et al., *J. Antibiotics* 49:689 (1997), Jarvest et al., *Bio. Med. Chem. Lett.* 3:2851 (1993) and Chen et al., *Proc. Natl. Acad. Sci. USA* 89:5872 (1992)). In addition, these ligand heterodimers are considerably less complex than previously identified compounds with comparable activity. Further optimization of the optimal building block and linker combinations could presumably be accomplished by evaluating a larger range of linkers with enhanced rigidity or by incorporating analogs of the optimal aldehyde precursors.

EXAMPLE 2

Pharmacophore Recombination Using N,N-Dimethylamines and Other Diamine Linkers

Figure 7:
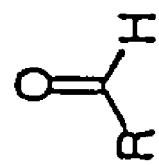
FIG. 7 shows a synthetic reaction wherein an aldehyde is reacted with a dimethylamine in the presence of support-bound triacetoxyborohydride to give rise to an N,N-dimethylamine organic compound.
Figure 7:
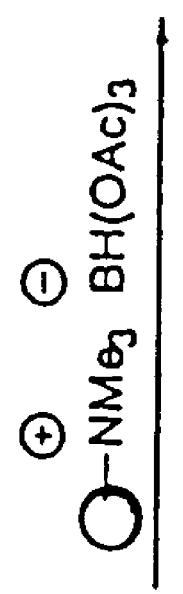
Figure 7:
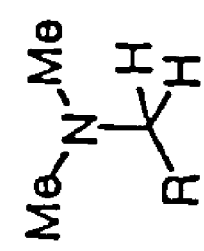

In addition to the use of aldehydes and oximes for the pharmacophore recombination method as described above, additional chemistries also find use. In this example, the organic compound building blocks are N,N-dimethylamine compounds that are prepared by reductive amination of starting aldehydes and dimethylamine using support-bound triacetoxyborohydride (Kaldor et al., *Tetrahedron Lett.* 37:7193–7196 (1996)). The chemistry of these reactions is shown in FIG. 7. Removal of the support-bound reducing agent by filtration followed by concentration to remove the volatile, excess dimethylamine then provides the pure N,N-dimethylamine monomer building blocks. Alternatively, the N,N-dimethylamine building blocks may be obtained by reduction using a sodium borohydride-based reducing agent in solution. The resulting amine product is then isolated from the excess reducing agent or aldehyde by passing down an acidic ion exchange column. The amine product is then obtained by elution from the ion exchange column with a volatile amine such as ammonia followed by concentration.

Figure 8:
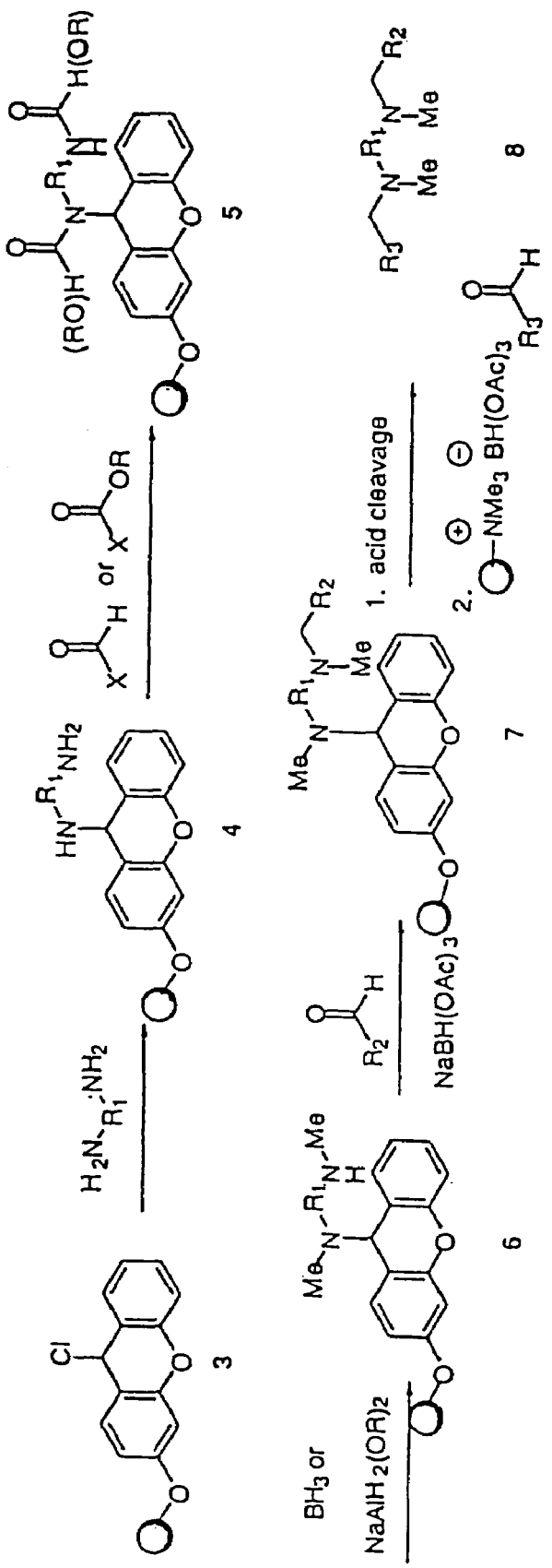
FIG. 8 shows a chemical synthesis sequence resulting in the production of a ligand of the present invention.

Linkage of the N,N-dimethylamine building blocks can be accomplished through the use of diamine linkers of which many are commercially available and many more can be readily prepared using well known methodology. The commercial availability of the diamine linkers allows rapid optimization of linker length, rigidity and orientation. An exemplary synthesis sequence is shown in FIG. 8. Specifically, support-bound chloride (3) (or other support-bound halide) is treated with excess of a diamine to provide an amine-derivatized support (4). Acylation of the amine functionality then provides support-bound formamide or carbamate (5). Reduction then provides support-bound secondary amine (6). Reductive amination then introduces one of the pharmacophore elements (7). Acid treatment then releases a secondary amine from the support, which can then be treated with the second pharmacophore monomer and sodium triacetoxyborohydride to provide the desired pharmacophore heterodimer (either support-bound reagent or alternative scavenging methods may be employed). Initial attachment of the diamine to the support can be accomplished using other support-bound alkyl halides or could be accomplished by reductive amination of a support-bound aldehyde or ketone. Fewer linkers are available that contain two secondary amine groups, but these can also be incorporated. in this case, the acylation step (4 to 5 in FIG. 8) and the subsequent reduction step (5 to 6 in FIG. 8) would be eliminated.

The foregoing description details specific methods which can be employed to practice the present invention. Having detailed such specific methods, those skilled in the art will well enough know how to devise alternative reliable methods at arriving at the same information in using the fruits of the present invention. Thus, however, detailed the foregoing may appear in text, it should not be construed as limiting the overall scope thereof; rather, the ambit of the present invention is to be determined only by the lawful construction of the appended claims. All documents cited herein are expressly incorporated by reference.

What is claimed:

1. A method for screening a library of small organic molecules for one or more candidate target binding fragments (CTBF's) that bind to a target biological molecule (TBM), each CTBF having a linkable functional group (LFG) or blocked form thereof (BLFG), wherein the LFG or BLFG contains a disulfide linking group (LG), the method comprising:
   (a) contacting the TBM with individual members of a library of the CTBF;
   (b) detecting or determining which CTBF's bind to the TBM; and
   (c) selecting CTBF's that bind to the TBM;
wherein the library is represented by the formula:

wherein $R^8$ is
   a straight chain or branched alkyl of 1 to 10 carbon atoms that is optionally substituted with up to five groups selected from the group consisting of halide, alkyl, aryl, heteroaryl, carboxy ester, carboxamide, amino, n-acylamino, alkoxy, hydroxy, mercapto, phosphono and sulphono; or
   an aryl or heteroaryl that is optionally substituted with halide, alkyl, aryl, halide, heteroaryl, carboxy ester, carboxamide, amino, n-acylamino, alkoxy, hydroxy, mercapto or phosphono;
   and wherein each CTBF of the library further comprises at least a second LG selected from the group consisting of amide, secondary amine, ureido, thiourea, carbamate and sulfonamide.

2. The method of claim 1, wherein (b) comprises quantifying the binding association of the CTBF's with the TBM.

3. The method of claim 2, wherein a quantitative spectroscopic property is used to determine the binding association of the CTBF's with the TBM.

4. The method of claim 1, wherein (b) is accomplished by an in vitro biological assay.

5. The method of claim 4, wherein (b) comprises an ELISA assay.

6. The method of claim 1, wherein X-ray crystallography is used to determine the binding association of the CTBF's with the TBM.

7. The method of claim 1, further comprising subjecting the bound CTBF's and TBM to X-ray crystallography.

8. The method of claim 1, further comprising linking at least two of the selected CTBF's or analogs thereof.

9. The method of claim 1, further comprising converting the selected CTBF's to structurally related analogs thereof.

10. The method of claim 1, further comprising linking the selected CTBF's to a second compound.

11. The method according to claim 1, wherein the TBM is a protein.

12. The method according to claim 11, wherein the protein is a hormone, cytokine, chemokine or receptor.

13. The method according to claim 1, wherein the TBM is an enzyme.

14. The method according to claim 13, wherein the enzyme is a protease, phosphatase (dephosphorylase) or kinase.

15. The method according to claim 1, wherein the library of CTBF's comprises small organic molecules with molecular weights of less than about 1000 Daltons.

16. The method according to claim 15, wherein the library of CTBF's comprises small organic molecules with molecular weights of less than about 500 Daltons.

17. The method of claim 16, wherein the library of CTBF's for binding to a TBM comprises at least about 100 different CTBF's.

18. The method of claim 1, wherein $R^8$ is a straight chain alkyl of 1 to 10 carbon atoms optionally substituted with amino or hydroxy.

19. The method of claim 1, wherein the second LG is an amide.

20. The method of claim 1, wherein the second LG is a sulfonamide.

21. The method of claim 1, wherein $R^8$ is a straight chain alkyl of 1 to 10 carbon atoms substituted with amino.

22. The method of claim 1, wherein $R^8$ is a straight chain alkyl of 1 to 10 carbon atoms substituted with hydroxy.

* * * * *